United States Patent [19]
Kirschbaum et al.

[11] Patent Number: 5,942,429
[45] Date of Patent: Aug. 24, 1999

[54] DEAH-BOX PROTEINS

[75] Inventors: Bernd Kirschbaum, Mainz; Stefan Muellner, Hochheim; Robert Bartlett, Darmstadt, all of Germany

[73] Assignee: Aventis Research & Technologies GmbH & Co KG., Frankfurt am Main, Germany

[21] Appl. No.: 08/760,075

[22] Filed: Dec. 4, 1996

[30] Foreign Application Priority Data

Dec. 4, 1995 [DE] Germany ............................ 195 45 126

[51] Int. Cl.⁶ .............................. C12N 9/16; C07H 21/04
[52] U.S. Cl. .................... 435/196; 435/199; 435/252.33; 435/325; 435/320.1; 536/23.1; 536/23.2; 536/23.5
[58] Field of Search ..................................... 435/195, 196, 435/199, 252.3, 252.33, 320.1, 325; 536/23.1, 23.2, 23.5

[56] References Cited

U.S. PATENT DOCUMENTS 5,466,576  11/1995  Schulz et al. ................................ 435/6

FOREIGN PATENT DOCUMENTS

WO 94 23059  10/1994  WIPO.
WO 94 28157  12/1994  WIPO.

OTHER PUBLICATIONS

Hillier et al. "ye39a10.r1 Homo sapiens cDNA clone 120090 5' Similar to SP:Ko3H1.2, Accession #T95243 CEO1027 RNA Helicase", Abstract No. XP–002061645 (Apr. 1995).
Nomura "Human mRNA for KIAA0224 Gene Complete cds.", Accession #D86977 Abstract No. XP002061646 (Aug. 25, 1996).
Nagase et al. "Prediction of the Coding Sequences of Unidentified Human Genes . . . "DNA Research 3:321–329 (1996).
Inoue et al. Nucleotide sequence of a fission yeast gene encoding the DEAH–box RNA helicase. Nucl. Acid Res. 20 (21), 5841, 1992.
Iggo et al., "Nuclear Protein P68 Is An RNA–Dependent ATPhase", The EMBO Journal, vol. 8, No. 6, (1989) pp. 1827–1831.
Sachs et al., "Translation Initiation and Ribosomal Biogenesis: Involvement of a Putative rRNA Helicase and RPL46", Science, (1990) pp. 1077–1079.
Lavoie et al., "Dbp45A Encodes a Drosophila Dead Box Protein With Similarity to a Putative Yeast Helicase Involved in Ribosome Assembly", Biochemica et Biophysica Acta, vol. 1216, (1993) pp. 140–144.
Naranda et al., "Two Structural Domains of Initiation Factor eIF–4B Are Involved in Binding to RNA", J. Biolog. Chem., vol. 269, No. 20, (1994) pp. 14465–14472.

Nagai et al., "The RNP Domain: A Sequence–Specific RNA–Binding Domain Involved in Processing and Transport of RNA", TIBS, vol. 20, (1995) pp. 235–240.
Sullenger, "Revising Messages Traveling Along the Cellular Information Superhighway", Chemistry & Biology, vol. 2, (1995) pp. 249–253.
McCarthy et al., "Cytoplasmic MRNA–Protein Interactions in Eukaryotic Gene Expression", TIBS, vol. 20, (1995) pp. 191–197.
Berget, "Exon Recognition in Vertebrate Splicing", Biological Chemistry, vol. 270, No. 6, (1995) pp. 2411–2414.
Vidic–Dankovic et al., "Leflunomide Prevents the Development of Experimentally Induced Myasthenia Gravis", Immunopharmac., vol. 17, No. 4, (1995) pp. 2273–2281.
Xiao et al., "Leflunomide Controls Rejections in Hamster to Rat Cardiac Xenografts", Transplantation, vol. 58, No. 7, (1994) pp. 828–834.
Hirschelmann et al., "Effects of Leflunomide on the Course of Listeriosis in Mice", Drug Research, vol. 45(1), No. 6, (1995) pp. 614–616.
Zielinski et al., "Leflunomide, a Reversible Inhibitor of Pyrimidine Biosynthesis", Inflamm. Res., vol. 44, Suppl. 2, (1995) pp. 207–208.
Curtis et al., "Translation Regulation in Development", Cell, vol. 81, (1995) pp. 171–178.
Keller, "No End Yet to Messenger RNA 3' Processing", Cell, vol. 81, (1995) pp. 829–832.
Simpson et al., "Sense From Nonsense: RNA Editing in Mitochondria of Kinetoplastid Protozoa and Slime Molds", Cell, vol. 81, (1995) pp. 837–840.
Godbout et al., "Amplification of a DEAD Box Protein Gene In Retinoblastoma Cell Lines", Proc. Natl. Acad. Sci., vol. 90, (1993) pp. 7578–7582.
Ripmaster et al., "A Putative ATP–Dependent RNA Helicase Involved in *Saccharomyces Cerevisiae* Ribosome Assembly", Proc. Natl., Acad. Sci, vol. 89, (1992) pp. 11131–11135.
De Valoir et al., "A Second Maternally Expressed Drosophila Gene Encodes a Putative RNA Helicase of the "Dead Box" Family", Proc. Natl. Acad. Sci., vol. 88, (1991) pp. 2113–2117.

(List continued on next page.)

*Primary Examiner*—Robert A Wax
*Assistant Examiner*—Nashaat T. Nashed
*Attorney, Agent, or Firm*—Foley & Lardner

[57] ABSTRACT

The present invention relates to the identification and molecular-biological and biochemical characterization of novel DEAH-box proteins which show structural similarity with other known helicases. The invention also relates to DNA sequences encoding such proteins. It is demonstrated that such proteins bind ATP and nucleic acid and possess helicase and ATPase activities. This invention further relates to processes for preparation of such proteins and their use in pharmacologically relevant test systems and therapeutic applications.

12 Claims, 21 Drawing Sheets

OTHER PUBLICATIONS

Chang et al., "Identification of Five Putative Yeast RNA Helicase Genes", Proc. Natl. Acad. Sci., vol. 87, (1990) pp. 1571–1575.

Linder et al., "Birth of the DEAD Box" Nature, vol. 337, (1989) pp. 121–122.

Hirling et al., "RNA Helicase Activity Associated With the Human p68 Protein", Nature, vol. 339, (1989) pp. 562–564.

Lasko et al., "The Product of the Drosophila Gene vasa is Very Similar to Eukaryotic Initiation Factor–4A", Nature, vol. 335 (1988) pp. 611–617.

Pause et al., "The HRIGRXXR Region of the Dead Box RNA Helicase Eukaryotic Translation Initiation Factor 4A is Required for RNA Binding and ATP Hydrolysis", Mol. & Cell. Bio., vol. 13, No. 11, (1993) pp. 6789–6798.

Jaramillo et al., "RNA Unwinding in Translation: Assembly of Helicase Complex Intermediates Comprising Eukaryotic Initiation Factors eIF–4F and eIF–4B", Mol. & Cell. Bio. vol. 11, No. 12, (1991) pp. 5992–5997.

Rozen et al., "Bidirectional RNA Helicase Activity of Eucaryotic Translation Initiation Factors 4A and 4F", Molecular & Cellular Biol., vol. 11, No. 3, (1990) pp. 1134–1144.

Fuller–Pace, "RNA Helicases: Modulators of RNA Structure", Trends in Cell Biology, vol. 4, (1994) pp. 271–274.

Schmid et al., "Translation Initiation Factor 4A From *Saccharomyces Cerevisiae:* Analysis of Residues Conserved in the DEAD Family of RNA Helicases", Mol. & Cell. Bio. vol. 11, No. 7, (1991) pp. 3463–3471.

Lost et al., "MRNAs Can be Stabilized by DEAD–Box Proteins", Nature, vol. 372, (1994) pp. 193–196.

Pause et al., "Helicases and RNA Unwinding in Translation", Current Opinion in Structural Biology, vol. 3, (1993) pp. 953–959.

Gorbalenya et al., "Two Related Superfamilies of Putative Helicases Involved in Recombination, Repair and Expression of DNA and RNA Genomes", Nucleic Acids Research, vol. 17, No. 12, (1989) pp. 4713–4729.

Koonin et al., "Autogenous Translation Regulation by *Escherichia Coli* A TPase SecA May be Mediated By an Intrinsic RNA Helicase Activity of This Protein", FEBS, vol. 298, No. 1, (1992) pp. 6–8.

Ford et al., "Nuclear Protein With Sequence Homology to Translation Initiation Factor eIF–4A", Nature, vol. 332, (1988) pp. 736–738.

Pai et al., "Refined Crystal Structure of the Triphosphate Conformation of H–ras p21 at 1.35 A Resolution: Implications for the Mechanism of GPT Hydrolysis", EMBO J., vol. 9, (1990) pp. 2351–2359.

Pause et al., "Mutational Analysis of a DEAD Box RNA Helicase: the Mammalian Translation Initiation Factor eIF–4A", EMBO J., vol. 11, (1992) 2643–2654.

Bartlett et al., "Nonsteriodal Anti–Inflammatory Drugs", Mechanisms and Clinical Uses.

Kuchle et al., "Prevention of Kidney and Skin Graft Rejection in Rats by Leflunomide, a New Immunomodulating Agent", Transplant Proc., vol. 23, (1991) p. 1083.

Zielinski et al., "Effects of Leflunomide (HWA 486) on Expression of Lymphocyte Activation Markers", Agents Actions, vol. 38, (1993) pp. C80–82.

Wilson et al., "2.2 Mb of Contiguous Nucleotide Sequence From Chromosome III of *C. Elegans*", Nature, vol. 368, (1994) pp. 32–38.

Ono et al., "Identification of a Putative RNA Helicase (HRH1), a Human Homolog of Yeast Prp22", Molecular and Cellular Biology, vol. 14, (1994) pp. 7611–7620.

Chen et al., "The Yeast PRP2 Protein, a Putative RNA–Dependent ATPase, Shares Extensive Sequence Homology with Two Other Pre–mRNA Splicing Factors", Nucl. Acids Res., vol. 18, (1990) pp. 6447.

Company et al., "Requirement of the RNA Helicase–like Protien PRP22 for Release of Messenger RNA from Spliceosomes", Nature, vol. 349, (1991) pp. 487–493.

Kuroda et al., "The Maleless Protein Associates with the X Chromosome to Regulate Dosage Compensation in Drosophila", Cell, vol. 66, (1991) pp. 935–947.

Zhang et al., "Molecular Cloning of the Gene Encoding Nuclear DNA Helicase II", J. Biol. Chem., vol. 270, (1995) pp. 16422–16427.

|   | cell line | % volume | area mm² | volume counts x mm² | mean value of counts |
|---|-----------|----------|----------|---------------------|----------------------|
| 1 | A20R      | 93.2     | 86.400   | 909378              | 5534                 |
| 2 | A20.2J    | 0.6      | 22.010   | 33267               | 148                  |
| 3 | A20.2J 1h | 1.0      | 22.010   | 27814               | 236                  |
| 4 | A20.2J 8h | 4.0      | 22.010   | 60160               | 937                  |
| 5 | A20.2J 16h| 0.7      | 22.010   | 32797               | 157                  |
| 6 | A20.2J 24h| 0.5      | 22.010   | 27391               | 106                  |

|   | cell line | % volume | area mm² | volume counts x mm² | mean value of counts | standard deviation |
|---|-----------|----------|----------|---------------------|----------------------|--------------------|
| 1 | A20R      | 14.1     | 22.780   | 22913               | 576                  | 334.5              |
| 2 | A20.2J    | 19.3     | 22.780   | 27782               | 790                  | 403.2              |
| 3 | A20.2J 1h | 14.1     | 22.780   | 22902               | 576                  | 302.5              |
| 4 | A20.2J 8h | 26.6     | 22.780   | 34568               | 1088                 | 416.4              |
| 5 | A20.2J 16h| 13.5     | 22.780   | 22332               | 551                  | 278.9              |
| 6 | A20.2J 24h| 12.5     | 22.780   | 21470               | 513                  | 310.2              |

|   | cell line | % volume | area mm² | volume counts x mm² | mean value of counts | standard deviation |
|---|---|---|---|---|---|---|
| 1 | A20R | 29.0 | 62.410 | 361861 | 5559 | 3999.1 |
| 2 | A20R 1d | 23.3 | 44.400 | 289814 | 6289 | 3549.0 |
| 3 | A20R 2d | 11.1 | 36.190 | 141943 | 3683 | 1457.7 |
| 4 | A20R 3d | 17.2 | 34.200 | 214247 | 6026 | 3026.5 |
| 5 | A20R 4d | 5.7 | 21.390 | 73851 | 3214 | 1195.2 |
| 6 | A20R 5d | 6.4 | 17.940 | 81115 | 4283 | 1363.3 |
| 7 | A20R 14d | 5.2 | 17.980 | 66433 | 3456 | 1145.5 |
| 8 | A20R 5months | 1.9 | 15.840 | 27014 | 1467 | 832.5 |

| | cell line | % volume | area mm² | volume counts x mm² | mean value of counts | standard deviation |
|---|---|---|---|---|---|---|
| 1 | A20R | 17.5 | 27.200 | 47005 | 941 | 832.2 |
| 2 | A20R 1d | 12.3 | 27.200 | 38127 | 659 | 646.3 |
| 3 | A20R 2d | 11.6 | 27.200 | 37724 | 625 | 590.2 |
| 4 | A20R 3d | 5.9 | 27.200 | 25075 | 315 | 384.5 |
| 5 | A20R 4d | 12.8 | 27.200 | 38766 | 687 | 635.5 |
| 6 | A20R 5d | 8.8 | 27.200 | 29539 | 474 | 481.5 |
| 7 | A20R 14d | 18.4 | 27.200 | 51164 | 986 | 820.9 |
| 8 | A20R 5months | 12.7 | 27.200 | 37462 | 682 | 605.5 |

|   | cell line | % volume | area mm² | volume counts x mm² | mean value of counts |
|---|---|---|---|---|---|
| 1 | Heart | 21.6 | 21.450 | 50406 | 1937 |
| 2 | Brain | 8.3 | 13.500 | 21494 | 1179 |
| 3 | Placenta | 6.8 | 11.660 | 17871 | 1119 |
| 4 | Lung | 5.9 | 10.920 | 15913 | 1044 |
| 5 | Liver | 12.9 | 15.300 | 31126 | 1621 |
| 6 | Skeletal Muscle | 29.5 | 21.660 | 65581 | 2614 |
| 7 | Kidney | 3.7 | 14.000 | 12950 | 512 |
| 8 | Pancreas | 11.3 | 15.510 | 28051 | 1395 |

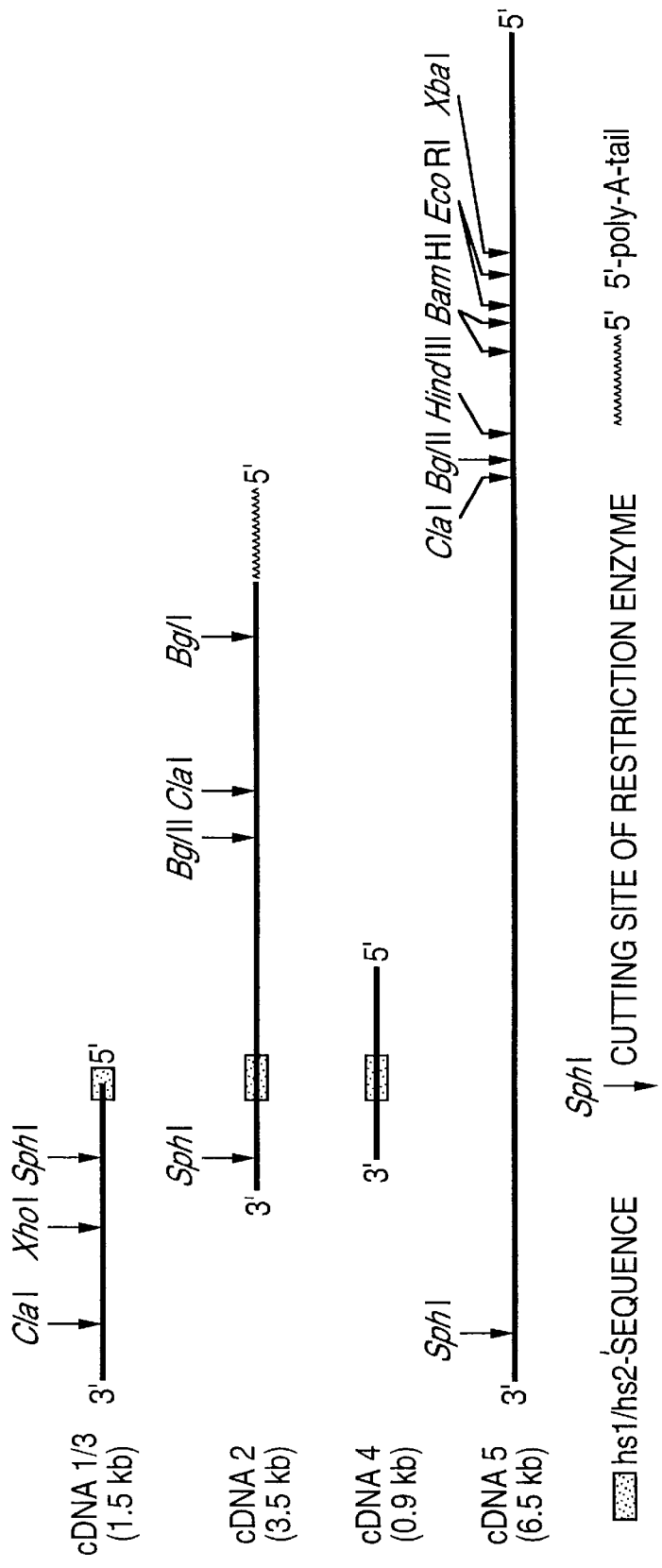
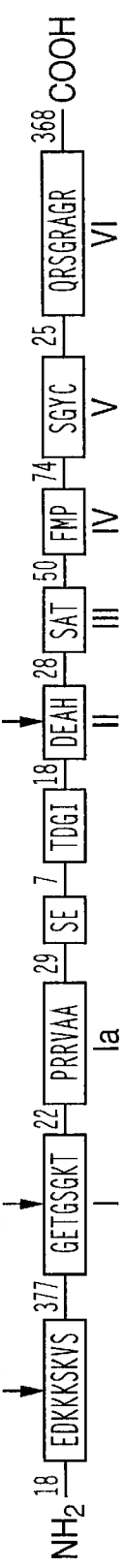
FIG. 6A
FIG. 6B

FIG. 7

|   |   |        |          | M    | G    | V    | K    | K    |     |            |
|---|---|--------|----------|------|------|------|------|------|-----|------------|
|   | 1 | A20-2  | 5'-ATG   | GGN  | GTN  | AAR  | AAR  | GG   |     | SEQ ID NO:7 |

|   |   |        |          | D    | I    | M    | G    | V    |     |            |
|---|---|--------|----------|------|------|------|------|------|-----|------------|
|   | 2 | A20-3  | 5'-GAT   | ATY  | ATS  | GGN  | GTN  | AA   |     | SEQ ID NO:8 |

|   |   |        |          | M    | G    | V    | K    | K    | E   |            |
|---|---|--------|----------|------|------|------|------|------|-----|------------|
|   | 3 | A20-4  | 5'-ATG   | GTN  | GTN  | AAR  | AAR  | GAR  | AC  |            |
|   |   |        |          |      |      |      |      |      |     | SEQ ID NO: 9 |

|   |   |        |          | K    | E    | T    | E    | P    | D   |            |
|---|---|--------|----------|------|------|------|------|------|-----|------------|
|   | 4 | A-20-5 | 5'-AAR   | GAR  | ACN  | GAR  | CCN  | GAY  | AA  |            |
|   |   |        |          |      |      |      |      |      |     | SEQ ID NO: 10 |

|   |   |         |          | (D   | M    | T    | A    | S    | T)  |            |
|---|---|---------|----------|------|------|------|------|------|-----|------------|
|   | 5 | A-20-6a | 5'-RTC   | CAT  | NGT  | NGC  | NGA  | NGT  |     |            |
|   |   |         |          |      |      |      |      |      |     | SEQ ID NO: 11 |

|   |   |         |          | (T   | A    | S    | T    | V    | I)  |            |
|---|---|---------|----------|------|------|------|------|------|-----|------------|
|   | 6 | A-20-6b | 5'-NGT   | AGC  | NGA  | NGT  | NAC  | NAT  |     |            |
|   |   |         |          |      |      |      |      |      |     | SEQ ID NO: 12 |

B

|   | 7 | hs-1 | 5'-TGT | GAT | CTG | CAA | ACA | TCT | GCA | CTG | TCC |             |
|---|---|------|--------|-----|-----|-----|-----|-----|-----|-----|-----|-------------|
|   |   |      |        |     |     |     |     |     |     |     |     | SEQ ID NO:13 |
|   | 8 | hs-2 | 5'-GCC | GGT | GAT | TGC | CAG | TGA | AGG | ATG | CCA |             |
|   |   |      |        |     |     |     |     |     |     |     |     | SEQ ID NO:14 |

FIG. 8A

```
     AAGGAGACGGAGCCGGACAAAGCTATGACAGAAGACGGGAAAGTGGACTACAGGACGGAG
  1  ---------+---------+---------+---------+---------+---------+  60
     TTCCTCTGCCTCGGCCTGTTTCGATACTGTCTTCTGCCCTTTCACCTGATGTCCTGCCTC

1  K  E  T  E  P  D  K  A  M  T  E  D  G  K  V  D  Y  R  T  E   -

CAGAAGTTTGCAGATCACATGAAGGAGAAAAGCGAGGCCAGCAGTGAGTTTGCCAAGAAG
 61  ---------+---------+---------+---------+---------+---------+ 120
     GTCTTCAAACGTCTAGTGTACTTCCTCTTTTCGCTCCGGTCGTCACTCAAACGGTTCTTC

21  Q  K  F  A  D  H  M  K  E  K  S  E  A  S  S  E  F  A  K  K   -

AAGTCGATCCTGGAGCAGAGGCAGTACCTGCCCATCTTTGCCGTGCAGCAGGAGCTCGTC
121  ---------+---------+---------+---------+---------+---------+ 180
     TTCAGCTAGGACCTCGTCTCCGTCATGGACGGGTAGAAACGGCACGTCGTCCTCGAGCAG

41  K  S  I  L  E  Q  R  Q  Y  L  P  I  F  A  V  Q  Q  E  L  V   -

ACCATCATCAGAGACAACAGCATTGTGGTCGTGGTCGGGGAGACAGGGAGTGGCAAGACC
181  ---------+---------+---------+---------+---------+---------+ 240
     TGGTAGTAGTCTCTGTTGTCGTAACACCAGCACCAGCCCCTCTGTCCCTCACCGTTCTGG

61  T  I  I  R  D  N  S  I  V  V  V  V  G  E  T  G  S  G  K  T   -

ACTCAGCTGACCCAGTACTTGCATGAAGATGGTTACACGGACTATGGGATGATCGGGTGT
241  ---------+---------+---------+---------+---------+---------+ 300
     TGAGTCGACTGGGTCATGAACGTACTTCTACCAATGTGCCTGATACCCTACTAGCCCACA

81  T  Q  L  T  Q  Y  L  H  E  D  G  Y  T  D  Y  G  M  I  G  C   -

ACCCAGCCCCGGCGTGTGGCTGCCATGTCAGCGGCCAAGAGAGTCAGTGAAGAGATGGGG
301  ---------+---------+---------+---------+---------+---------+ 360
     TGGGTCGGGGCCGCACACCGACGGTACAGTCGCCGGTTCTCTCAGTCACTTCTCTACCCC

101  T  Q  P  R  R  V  A  A  M  S  A  A  K  R  V  S  E  E  M  G   -

GGCAACCTTGGAGAAGAGGTGGGCTATGCCATCCGCTTTGAGGACTGCACTTCGGAAAAC
361  ---------+---------+---------+---------+---------+---------+ 420
     CCGTTGGAACCTCTTCTCCACCCGATACGGTAGGCGAAACTCCTGACGTGAAGCCTTTTG

```
     AACTTGATCAAGTACATGACGGATGGGATCCTGCTGCGCGAGTCCCTCCGGCAGGCTGAC
421  ------------+---------+---------+---------+---------+---------+  480
     TTGAACTAGTTCATGTACTGCCTACCCTAGGACGACGCGCTCAGGGAGGCCGTCCGACTG

141  N   L   I   K   Y   M   T   D   G   I   L   L   R   E   S   L   R   Q   A   D   -

CTGGACCACTACAGCGCCGTCATCATGGATGAGGCCCACGAGCGCTCCCTCAACACCGAC
481  ------------+---------+---------+---------+---------+---------+  540
     GACCTGGTGATGTCGCGGCAGTAGTACCTACTCCGGGTGCTCGCGAGGGAGTTGTGGCTG

161  L   D   H   Y   S   A   V   I   M   D   E   A   H   E   R   S   L   N   T   D   -

GTGCTTTTTGGGCTGCTCCGGGAGGTTGTGGCTCGAGGCTCAGACCTGAAGCTCATGGTT
541  ------------+---------+---------+---------+---------+---------+  600
     CACGAAAAACCCGACGAGGCCCTCCAACACCGAGCTCCGAGTCTGGACTTCGAGTACCAA

181  V   L   F   G   L   L   R   E   V   V   A   R   G   S   D   L   K   L   M   V   -

ACATCGGCTACT
601  ---------+--  612
     TGTAGCCGATGA

```
        ATGGGGGACACCAGTGAGGATGCCTCGATCCATCGATTGGAAGGCACTGATCTGGACTGT
148     --+---------+---------+---------+---------+---------+------ 207
        TACCCCCTGTGGTCACTCCTACGGAGCTAGGTAGCTAACCTTCCGTGACTAGACCTGACA a       M  G  D  T  S  E  D  A  S  I  H  R  L  E  G  T  D  L  D  C   -

CAGGTTGGTGGTCTTATTTGCAAGTCCAAAAGTGCGGCCAGCGAGCAGCATGTCTTCAAG
208     --+---------+---------+---------+---------+---------+------ 267
        GTCCAACCACCAGAATAAACGTTCAGGTTTTCACGCCGGTCGCTCGTCGTACAGAAGTTC a       Q  V  G  G  L  I  C  K  S  K  S  A  A  S  E  Q  H  V  F  K   -

GCTCCTGCTCCCCGCCCTTCATTACTCGGACTGGACTTGCTGGCTTCCCTGAAACGGAGA
268     --+---------+---------+---------+---------+---------+------ 327
        CGAGGACGAGGGGCGGGAAGTAATGAGCCTGACCTGAACGACCGAAGGGACTTTGCCTCT a       A  P  A  P  R  P  S  L  L  G  L  D  L  L  A  S  L  K  R  R   -

GAGCGAGAGGAGAAGGACGATGGGGAGGACAAGAAGAAGTCCAAAGTCTCCTCCTACAAG
328     --+---------+---------+---------+---------+---------+------ 387
        CTCGCTCTCCTCTTCCTGCTACCCCTCCTGTTCTTCTTCAGGTTTCAGAGGAGGATGTTC a       E  R  E  E  K  D  D  G  E  D  K  K  K  S  K  V  S  S  Y  K   -

GACTGGGAAGAGAGCAAGGATGACCAGAAGGATGCTGAGGAAGAGGGCGGTGACCAGGCT
388     --+---------+---------+---------+---------+---------+------ 447
        CTGACCCTTCTCTCGTTCCTACTGGTCTTCCTACGACTCCTTCTCCCGCCACTGGTCCGA a       D  W  E  E  S  K  D  D  Q  K  D  A  E  E  E  G  G  D  Q  A   -

GGCCAAAATATCCGGAAAGACAGACATTATCGGTCTGCTCGGGTAGAGACTCCATCCCAT
448     --+---------+---------+---------+---------+---------+------ 507
        CCGGTTTTATAGGCCTTTCTGTCTGTAATAGCCAGACGAGCCCATCTCTGAGGTAGGGTA a       G  Q  N  I  R  K  D  R  H  Y  R  S  A  R  V  E  T  P  S  H   -

CCGGGTGGTGTGAGCGAAGAGTTTTGGGAACGCAGTCGGCAGAGAGAGCGGGAGCGGCGG
508     --+---------+---------+---------+---------+---------+------ 567
        GGCCCACCACACTCGCTTCTCAAAACCCTTGCGTCAGCCGTCTCTCTCGCCCTCGCCGCC a       P  G  G  V  S  E  E  F  W  E  R  S  R  Q  R  E  R  E  R  R   -
```

FIG. 9B

```
      GAACATGGTGTCTATGCCTCGTCCAAAGAAGAAAAGGATTGGAAGAAGGAGAAATCGCGG
  568 --+---------+---------+---------+---------+---------+------ 627
      CTTGTACCACAGATACGGAGCAGGTTTCTTCTTTTCCTAACCTTCTTCCTCTTTAGCGCC a       E  H  G  V  Y  A  S  S  K  E  E  K  D  W  K  K  E  K  S  R  -

GATCGAGACTATGACCGCAAGAGGGACAGAGATGAGCGGGATAGAAGTAGGCACAGCAGC
  628 --+---------+---------+---------+---------+---------+------ 687
      CTAGCTCTGATACTGGCGTTCTCCCTGTCTCTACTCGCCCTATCTTCATCCGTGTCGTCG a       D  R  D  Y  D  R  K  R  D  R  D  E  R  D  R  S  R  H  S  S  -

AGATCAGAGCGAGATGGAGGGTCAGAGCGTAGCAGCAGAAGAAATGAACCCGAGAGCCCA
  688 --+---------+---------+---------+---------+---------+------ 747
      TCTAGTCTCGCTCTACCTCCCAGTCTCGCATCGTCGTCTTCTTTACTTGGGCTCTCGGGT a       R  S  E  R  D  G  G  S  E  R  S  S  R  R  N  E  P  E  S  P  -

CGACATCGACCTAAAGATGCAGCCACCCCTTCAAGGTCTACCTGGGAGGAAGAGGACAGT
  748 --+---------+---------+---------+---------+---------+------ 807
      GCTGTAGCTGGATTTCTACGTCGGTGGGGAAGTTCCAGATGGACCCTCCTTCTCCTGTCA a       R  H  R  P  K  D  A  A  T  P  S  R  S  T  W  E  E  D  S  -

GGCTATGGCTCCTCAAGGCGCTCACAGTGGGAATCGCCCTCCCCGACGCCTTCCTATCGG
  808 --+---------+---------+---------+---------+---------+------ 867
      CCGATACCGAGGAGTTCCGCGAGTGTCACCCTTAGCGGGAGGGGCTGCGGAAGGATAGCC a       G  Y  G  S  S  R  R  S  Q  W  E  S  P  S  P  T  P  S  Y  R  -

GATTCTGAGCGGAGCCATCGGCTGTCCACTCGAGATCGAGACAGGTCTGTGAGGGGCAAG
  868 --+---------+---------+---------+---------+---------+------ 927
      CTAAGACTCGCCTCGGTAGCCGACAGGTGAGCTCTAGCTCTGTCCAGACACTCCCCGTTC a       D  S  E  R  S  H  R  L  S  T  R  D  R  D  R  S  V  R  G  K  -

TACTCGGATGACACGCCTCTGCCAACTCCCTCCTACAAATATAACGAGTGGGCCGATGAC
  928 --+---------+---------+---------+---------+---------+------ 987
      ATGAGCCTACTGTGCGGAGACGGTTGAGGGAGGATGTTTATATTGCTCACCCGGCTACTG a       Y  S  D  D  T  P  L  P  T  P  S  Y  K  Y  N  E  W  A  D  D  -
```

FIG. 9C

```
     AGAAGACACTTGGGGTCCACCCCGCGTCTGTCCAGGGGCCGAGGAAGACGTGAGGAGGGC
988  --+---------+---------+---------+---------+---------+------ 1047
     TCTTCTGTGAACCCCAGGTGGGGCGCAGACAGGTCCCCGGCTCCTTCTGCACTCCTCCCG a    R  R  H  L  G  S  T  P  R  L  S  R  G  R  R  E  E  G     -

GAAGAAGGAATTTCATTTGACACGGAGGAGGAGCGGCAGCAGTGGGAAGATGACCAGAGG
1048 --+---------+---------+---------+---------+---------+------ 1107
     CTTCTTCCTTAAAGTAAACTGTGCCTCCTCCTCGCCGTCGTCACCCTTCTACTGGTCTCC a    E  E  G  I  S  F  D  T  E  E  E  R  Q  Q  W  E  D  D  Q  R  -

CAAGCCGATCGGGATTGGTACATGATGGACGAGGGCTATGACGAGTTCCACAACCCGCTG
1108 --+---------+---------+---------+---------+---------+------ 1167
     GTTCGGCTAGCCCTAACCATGTACTACCTGCTCCCGATACTGCTCAAGGTGTTGGGCGAC a    Q  A  D  R  D  W  Y  M  M  D  E  G  Y  D  E  F  H  N  P  L  -

GCCTACTCCTCCGAGGACTACGTGAGGAGGCGGGAGCAGCACCTGCATAAACAGAAGCAG
1168 --+---------+---------+---------+---------+---------+------ 1227
     CGGATGAGGAGGCTCCTGATGCACTCCTCCGCCCTCGTCGTGGACGTATTTGTCTTCGTC a    A  Y  S  S  E  D  Y  V  R  R  R  E  Q  H  L  H  K  Q  K  Q  -

AAGCGCATTTCAGCTCAGCGGAGACAGATCAATGAGGATAACGAGCGCTGGGAGACAAAC
1228 --+---------+---------+---------+---------+---------+------ 1287
     TTCGCGTAAAGTCGAGTCGCCTCTGTCTAGTTACTCCTATTGCTCGCGACCCTCTGTTTG a    K  R  I  S  A  Q  R  R  Q  I  N  E  D  N  E  R  W  E  T  N  -

CGCATGCTCACCAGTGGGGTGGTCCATCGGCTGGAGGTGGATGAGGACTTTGAAGAGGAC
1288 --+---------+---------+---------+---------+---------+------ 1347
     GCGTACGAGTGGTCACCCCACCAGGTAGCCGACCTCCACCTACTCCTGAAACTTCTCCTG a    R  M  L  T  S  G  V  V  H  R  L  E  V  D  E  D  F  E  E  D  -

AACGCGGCCAAGGTGCATCTGATGGTGCACAATCTGGTGCCTCCCTTTCTGGATGGGCGC
1348 --+---------+---------+---------+---------+---------+------ 1407
     TTGCGCCGGTTCCACGTAGACTACCACGTGTTAGACCACGGAGGGAAAGACCTACCCGCG a    N  A  A  K  V  H  L  M  V  H  N  L  V  P  P  F  L  D  G  R  -
```

FIG. 9D

```
       ATTGTCTTCACCAAGCAGCCGGAGCCGGTGATTCCAGTGAAGGATGCTACTTCTGACCTG
  1408 --+---------+---------+---------+---------+---------+------ 1467
       TAACAGAAGTGGTTCGTCGGCCTCGGCCACTAAGGTCACTTCCTACGATGAAGACTGGAC a      I  V  F  T  K  Q  P  E  P  V  I  P  V  K  D  A  T  S  D  L  -

GCCATCATTGCTCGGAAAGGCAGCCAGACAGTGCGGAAGCACAGGGAGCAGAAGGAGCGC
  1468 --+---------+---------+---------+---------+---------+------ 1527
       CGGTAGTAACGAGCCTTTCCGTCGGTCTGTCACGCCTTCGTGTCCCTCGTCTTCCTCGCG a      A  I  I  A  R  K  G  S  Q  T  V  R  K  H  R  E  Q  K  E  R  -

AAGAAGGCTCAGCACAAACACTGGGAACTGGCGGGGACCAAACTGGGAGATATAATGGGC
  1528 --+---------+---------+---------+---------+---------+------ 1587
       TTCTTCCGAGTCGTGTTTGTGACCCTTGACCGCCCCTGGTTTGACCCTCTATATTACCCG a      K  K  A  Q  H  K  H  W  E  L  A  G  T  K  L  G  D  I  M  G  -

GTCAAGAAGGAGGAAGAGCCAGATAAAGCTGTGACGGAGGATGGGAAGGTGGACTACAGG
  1588 --+---------+---------+---------+---------+---------+------ 1647
       CAGTTCTTCCTCCTTCTCGGTCTATTTCGACACTGCCTCCTACCCTTCCACCTGATGTCC a      V  K  K  E  E  E  P  D  K  A  V  T  E  D  G  K  V  D  Y  R  -

ACAGAGCAGAAGTTTGCAGATCACATGAAGAGAAAGAGCGAAGCCAGCAGTGAATTTGCA
  1648 --+---------+---------+---------+---------+---------+------ 1707
       TGTCTCGTCTTCAAACGTCTAGTGTACTTCTCTTTCTCGCTTCGGTCGTCACTTAAACGT a      T  E  Q  K  F  A  D  H  M  K  R  K  S  E  A  S  S  E  F  A  -

AAGAAGAAGTCCATCCTGGAGCAGAGGCAGTACCTGCCCATCTTTGCAGTGCAGCAGGAG
  1708 --+---------+---------+---------+---------+---------+------ 1767
       TTCTTCTTCAGGTAGGACCTCGTCTCCGTCATGGACGGGTAGAAACGTCACGTCGTCCTC a      K  K  K  S  I  L  E  Q  R  Q  Y  L  P  I  F  A  V  Q  Q  E  -

CTGCTCACTATTATCAGAGACAACAGCATCGTGATCGTGGTTGGGGAGACGGGGAGTGGT
  1768 --+---------+---------+---------+---------+---------+------ 1827
       GACGAGTGATAATAGTCTCTGTTGTCGTAGCACTAGCACCAACCCCTCTGCCCCTCACCA a      L  L  T  I  I  R  D  N  S  I  V  I  V  V  G  E  T  G  S  G  -
```

FIG. 9E

```
        AAGACCACTCAGCTGACGCAGTACCTGCATGAAGATGGTTACACGGACTATGGGATGATT
   1828 --+---------+---------+---------+---------+---------+------ 1887
        TTCTGGTGAGTCGACTGCGTCATGGACGTACTTCTACCAATGTGCCTGATACCCTACTAA a       K  T  T  Q  L  T  Q  Y  L  H  E  D  G  Y  T  D  Y  G  M  I  -

GGGTGTACCCAGCCCCGGCGTGTAGCTGCCATGTCAGTGGCCAAGAGAGTCAGTGAAGAG
   1888 --+---------+---------+---------+---------+---------+------ 1947
        CCCACATGGGTCGGGGCCGCACATCGACGGTACAGTCACCGGTTCTCTCAGTCACTTCTC a       G  C  T  Q  P  R  R  V  A  A  M  S  V  A  K  R  V  S  E  E  -

ATGGGGGGAAACCTTGGCGAGGAGGTGGGCTATGCCATCCGCTTTGAAGACTGCACTTCA
   1948 --+---------+---------+---------+---------+---------+------ 2007
        TACCCCCCTTTGGAACCGCTCCTCCACCCGATACGGTAGGCGAAACTTCTGACGTGAAGT a       M  G  G  N  L  G  E  E  V  G  Y  A  I  R  F  E  D  C  T  S  -

GAGAACACCTTGATCAAATACATGACTGACGGGATCCTGCTCCGAGAGTCCCTCCGGGAA
   2008 --+---------+---------+---------+---------+---------+------ 2067
        CTCTTGTGGAACTAGTTTATGTACTGACTGCCCTAGGACGAGGCTCTCAGGGAGGCCCTT a       E  N  T  L  I  K  Y  M  T  D  G  I  L  L  R  E  S  L  R  E  -

GCCGACCTGGATCACTACAGTGCCATCATCATGGACGAGGCCCACGAGCGCTCCCTCAAC
   2068 --+---------+---------+---------+---------+---------+------ 2127
        CGGCTGGACCTAGTGATGTCACGGTAGTAGTACCTGCTCCGGGTGCTCGCGAGGGAGTTG a       A  D  L  D  H  Y  S  A  I  I  M  D  E  A  H  E  R  S  L  N  -

ACTGACGTGCTCTTTGGGCTGCTCCGGGAGGTAGTGGCTCGGCGCTCAGACCTGAAGCTC
   2128 --+---------+---------+---------+---------+---------+------ 2187
        TGACTGCACGAGAAACCCGACGAGGCCCTCCATCACCGAGCCGCGAGTCTGGACTTCGAG a       T  D  V  L  F  G  L  L  R  E  V  V  A  R  R  S  D  L  K  L  -

ATCGTCACATCAGCCACGATGGATGCGGAGAAGTTTGCTGCCTTTTTTGGGAATGTCCCC
   2188 --+---------+---------+---------+---------+---------+------ 2247
        TAGCAGTGTAGTCGGTGCTACCTACGCCTCTTCAAACGACGGAAAAAACCCTTACAGGGG a       I  V  T  S  A  T  M  D  A  E  K  F  A  A  F  F  G  N  V  P  -
```

FIG. 9F

```
         ATCTTCCACATCCCTGGCCGTACCTTCCCTGTTGACATCCTCTTCAGCAAGACCCCACAG
   2248  --+---------+---------+---------+---------+---------+------- 2307
         TAGAAGGTGTAGGGACCGGCATGGAAGGGACAACTGTAGGAGAAGTCGTTCTGGGGTGTC a         I  F  H  I  P  G  R  T  F  P  V  D  I  L  F  S  K  T  P  Q   -

GAGGATTACGTGGAGGCTGCAGTGAAGCAGTCCTTGCAGGTGCACCTGTCGGGGGCCCCT
   2308  --+---------+---------+---------+---------+---------+------- 2367
         CTCCTAATGCACCTCCGACGTCACTTCGTCAGGAACGTCCACGTGGACAGCCCCCGGGGA a         E  D  Y  V  E  A  A  V  K  Q  S  L  Q  V  H  L  S  G  A  P   -

GGAGACATCCTTATCTTCATGCCTGGCCAAGAGGACATTGAGGTGACCTCAGACCAGATT
   2368  --+---------+---------+---------+---------+---------+------- 2427
         CCTCTGTAGGAATAGAAGTACGGACCGGTTCTCCTGTAACTCCACTGGAGTCTGGTCTAA a         G  D  I  L  I  F  M  P  G  Q  E  D  I  E  V  T  S  D  Q  I   -

GTGGAGCATCTGGAGGAACTGGAGAACGCGCCTGCCCTGGCTGTGCTGCCCATCTACTCT
   2428  --+---------+---------+---------+---------+---------+------- 2487
         CACCTCGTAGACCTCCTTGACCTCTTGCGCGGACGGGACCGACACGACGGGTAGATGAGA a         V  E  H  L  E  E  L  E  N  A  P  A  L  A  V  L  P  I  Y  S   -

CAGCTGCCTTCTGACCTCCAGGCCAAAATCTTCCAGAAGGCTCCAGATGGCGTTCGGAAG
   2488  --+---------+---------+---------+---------+---------+------- 2547
         GTCGACGGAAGACTGGAGGTCCGGTTTTAGAAGGTCTTCCGAGGTCTACCGCAAGCCTTC a         Q  L  P  S  D  L  Q  A  K  I  F  Q  K  A  P  D  G  V  R  K   -

TGCATCGTTGCCACCAATATTGCCGAGACGTCTCTCACTGTTGACGGCATCATGTTTGTT
   2548  --+---------+---------+---------+---------+---------+------- 2607
         ACGTAGCAACGGTGGTTATAACGGCTCTGCAGAGAGTGACAACTGCCGTAGTACAAACAA a         C  I  V  A  T  N  I  A  E  T  S  L  T  V  D  G  I  M  F  V   -

ATCGATTCTGGTTATTGCAAATTAAAGGTCTTCAACCCCAGGATTGGCATGGATGCTCTG
   2608  --+---------+---------+---------+---------+---------+------- 2667
         TAGCTAAGACCAATAACGTTTAATTTCCAGAAGTTGGGGTCCTAACCGTACCTACGAGAC a         I  D  S  G  Y  C  K  L  K  V  F  N  P  R  I  G  M  D  A  L   -
```

FIG. 9G

```
          CAGATCTATCCCATTAGCCAGGCCAATGCCAACCAGCGGTCAGGGCGAGCCGGCAGGACG
    2668  --+---------+---------+---------+---------+---------+------- 2727
          GTCTAGATAGGGTAATCGGTCCGGTTACGGTTGGTCGCCAGTCCCGCTCGGCCGTCCTGC a         Q  I  Y  P  I  S  Q  A  N  A  N  Q  R  S  G  R  A  G  R  T   -

GGCCCAGGTCAGTGTTTCAGGCTCTACACCCAGAGCGCCTACAAGAATGAGCTCCTGACC
    2728  --+---------+---------+---------+---------+---------+------- 2787
          CCGGGTCCAGTCACAAAGTCCGAGATGTGGGTCTCGCGGATGTTCTTACTCGAGGACTGG a         G  P  G  Q  C  F  R  L  Y  T  Q  S  A  Y  K  N  E  L  L  T   -

ACCACAGTGCCCGAGATCCAGAGGACTAACCTGGCCAACGTGGTGCTGCTGCTCAAGTCC
    2788  --+---------+---------+---------+---------+---------+------- 2847
          TGGTGTCACGGGCTCTAGGTCTCCTGATTGGACCGGTTGCACCACGACGACGAGTTCAGG a         T  T  V  P  E  I  Q  R  T  N  L  A  N  V  V  L  L  L  K  S   -

CTCGGGGTGCAGGACCTGCTGCAGTTCCACTTCATGGACCCGCCCCCGGAGGACAACATG
    2848  --+---------+---------+---------+---------+---------+-------- 2907
          GAGCCCCACGTCCTGGACGACGTCAAGGTGAAGTACCTGGGCGGGGCCTCCTGTTGTAC a         L  G  V  Q  D  L  L  Q  F  H  F  M  D  P  P  P  E  D  N  M   -

CTCAACTCTATGTATCAGCTCTGGATCCTCGGGGCCCTGGACAACACAGGTGGTCTGACC
    2908  --+---------+---------+---------+---------+---------+------- 2967
          GAGTTGAGATACATAGTCGAGACCTAGGAGCCCCGGGACCTGTTGTGTCCACCAGACTGG a         L  N  S  M  Y  Q  L  W  I  L  G  A  L  D  N  T  G  G  L  T   -

TCTACCGGGCGGCTGATGGTGGAGTTCCCGCTGGACCCTGCCCTGTCCAAGATGCTCATC
    2968  --+---------+---------+---------+---------+---------+------- 3027
          AGATGGCCCGCCGACTACCACCTCAAGGGCGACCTGGGACGGGACAGGTTCTACGAGTAG a         S  T  G  R  L  M  V  E  F  P  L  D  P  A  L  S  K  M  L  I   -

GTGTCCTGTGACATGGGCTGCAGCTCCGAGATCCTGCTCATCGTTTCCATGCTCTCGGTC
    3028  --+---------+---------+---------+---------+---------+------- 3087
          CACAGGACACTGTACCCGACGTCGAGGCTCTAGGACGAGTAGCAAAGGTACGAGAGCCAG a         V  S  C  D  M  G  C  S  S  E  I  L  L  I  V  S  M  L  S  V   -
```

FIG. 9H

```
         CCAGCCATCTTCTACAGGCCCAAGGGTCGAGAGGAGGAGAGTGATCAAATCCGGGAGAAG
    3088 --+---------+---------+---------+---------+---------+------ 3147
         GGTCGGTAGAAGATGTCCGGGTTCCCAGCTCTCCTCCTCTCACTAGTTTAGGCCCTCTTC a        P  A  I  F  Y  R  P  K  G  R  E  E  E  S  D  Q  I  R  E  K   -

TTCGCTGTTCCTGAGAGCGATCATTTGACCTACCTGAATGTTTACCTGCAGTGGAAGAAC
    3148 --+---------+---------+---------+---------+---------+------ 3207
         AAGCGACAAGGACTCTCGCTAGTAAACTGGATGGACTTACAAATGGACGTCACCTTCTTG a        F  A  V  P  E  S  D  H  L  T  Y  L  N  V  Y  L  Q  W  K  N   -

AATAATTACTCCACCATCTGGTGTAACGATCATTTCATCCATGCTAAGGCCATGCGGAAG
    3208 --+---------+---------+---------+---------+---------+------ 3267
         TTATTAATGAGGTGGTAGACCACATTGCTAGTAAAGTAGGTACGATTCCGGTACGCCTTC a        N  N  Y  S  T  I  W  C  N  D  H  F  I  H  A  K  A  M  R  K   -

GTCCGGGAGGTGCGAGCTCAACTCAAGGACATCATGGTGCAGCAGCGGATGAGCCTGGCC
    3268 --+---------+---------+---------+---------+---------+------ 3327
         CAGGCCCTCCACGCTCGAGTTGAGTTCCTGTAGTACCACGTCGTCGCCTACTCGGACCGG a        V  R  E  V  R  A  Q  L  K  D  I  M  V  Q  Q  R  M  S  L  A   -

TCGTGTGGCACTGACTGGGACATCGTCAGGAAGTGCATCTGTGCTGCCTATTTCCACCAA
    3328 --+---------+---------+---------+---------+---------+------ 3387
         AGCACACCGTGACTGACCCTGTAGCAGTCCTTCACGTAGACACGACGGATAAAGGTGGTT a        S  C  G  T  D  W  D  I  V  R  K  C  I  C  A  A  Y  F  H  Q   -

GCAGCCAAGCTCAAGGGAATCGGGGAGTACGTGAACATCCGCACAGGGATGCCCTGCCAC
    3388 --+---------+---------+---------+---------+---------+------ 3447
         CGTCGGTTCGAGTTCCCTTAGCCCCTCATGCACTTGTAGGCGTGTCCCTACGGGACGGTG a        A  A  K  L  K  G  I  G  E  Y  V  N  I  R  T  G  M  P  C  H   -

TTGCACCCCACCAGCTCCCTTTTTGGAATGGGCTACACCCCAGATTACATAGTGTATCAC
    3448 --+---------+---------+---------+---------+---------+------ 3507
         AACGTGGGGTGGTCGAGGGAAAAACCTTACCCGATGTGGGGTCTAATGTATCACATAGTG a        L  H  P  T  S  S  L  F  G  M  G  Y  T  P  D  Y  I  V  Y  H   -
```

FIG. 9I

```
     GAGTTGGTCATGACCACCAAGGAGTATATGCAGTGTGTGACCGCTGTGGACGGGGAGTGG
3508 --+---------+---------+---------+---------+---------+------- 3567
     CTCAACCAGTACTGGTGGTTCCTCATATACGTCACACACTGGCGACACCTGCCCCTCACC a      E  L  V  M  T  T  K  E  Y  M  Q  C  V  T  A  V  D  G  E  W  -

CTGGCGGAGCTGGGCCCCATGTTCTATAGCGTGAAACAGGCGGGCAAGTCACGGCAGGAG
3568 --+---------+---------+---------+---------+---------+------- 3627
     GACCGCCTCGACCCGGGGTACAAGATATCGCACTTTGTCCGCCCGTTCAGTGCCGTCCTC a      L  A  E  L  G  P  M  F  Y  S  V  K  Q  A  G  K  S  R  Q  E  -

AACCGTCGTCGGGCCAAAGAGGAAGCCTCTGCCATGGAGGAGGAGATGGCGCTGGCCGAG
3628 --+---------+---------+---------+---------+---------+------- 3687
     TTGGCAGCAGCCCGGTTTCTCCTTCGGAGACGGTACCTCCTCCTCTACCGCGACCGGCTC a      N  R  R  R  A  K  E  E  A  S  A  M  E  E  E  M  A  L  A  E  -

GAGCAGCTGCGAGCCCGGCGGCAGGAGCAGGAGAAGCGCAGCCCCCTGGGCAGTGTCAGG
3688 --+---------+---------+---------+---------+---------+------- 3747
     CTCGTCGACGCTCGGGCCGCCGTCCTCGTCCTCTTCGCGTCGGGGGACCCGTCACAGTCC a      E  Q  L  R  A  R  R  Q  E  Q  E  K  R  S  P  L  G  S  V  R  -

TCTACGAAGATCTACACTCCAGGCCGGAAAGAGCAAGGGGAGCCCATGACCCCTCGCCGC
3748 --+---------+---------+---------+---------+---------+------- 3807
     AGATGCTTCTAGATGTGAGGTCCGGCCTTTCTCGTTCCCCTCGGGTACTGGGGAGCGGCG a      S  T  K  I  Y  T  P  G  R  K  E  Q  G  E  P  M  T  P  R  R  -

ACGCCAGCCCGCTTTGGTCTGTGA
3808 --+---------+---------+- 3831
     TGCGGTCGGGCGAAACCAGACACT a      T  P  A  R  F  G  L  *
```

FIG. 10

| Protein/sequence | Organism | Corres-pondences | Tasks in the cell | Biochemical properties |
|---|---|---|---|---|
| K03h1.2 | C. elegans | 65 % | Possible ATP-dependent RNA helicase | ? |
| HRH1 | Mensch | 60 % | Human homolog to PRP 22 | ? |
| PRP16 | S. cerevisiae | 51 % | Second step in pre-mRNA splicing; suppressor of mutations in the "branch point" | RNA-dependent ATPase |
| PRP2 | S. cerevisiae | 50 % | First step in pre-mRNA splicing | RNA-dependent ATPase |
| PRP22 | S. cerevisiae | 49 % | Release of spliced mRNA from the spliceosome | ? |
| MLE | D. melanogaster | 43 % | "Dosage compensation" - compensation for the missing X-chromosome in the male | ? |
| NDH II | Rind | 42 % | Unknown | RNA and DNA helicase activity |

SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
          (A) LENGTH: 11 amino acids
          (B) TYPE: amino acid
          (C) STRANDEDNESS: single
          (D) TOPOLOGY: linear (xi) SEQUENCE DESCRIPTION: SEQ ID NO:1:

Lys Leu Gly Asp Ile Met Gly Val Lys Lys Glu
1              5                     10

(2) INFORMATION FOR SEQ ID NO:2:

(i) SEQUENCE CHARACTERISTICS:
          (A) LENGTH: 16 amino acids
          (B) TYPE: amino acid
          (C) STRANDEDNESS: single
          (D) TOPOLOGY: linear (xi) SEQUENCE DESCRIPTION: SEQ ID NO:2:

Lys Leu Gly Asp Ile Met Gly Val Lys Lys Glu Thr Glu Pro Asp Lys
1              5                     10                 15

(2) INFORMATION FOR SEQ ID NO:3:

(i) SEQUENCE CHARACTERISTICS:
          (A) LENGTH: 13 amino acids
          (B) TYPE: amino acid
          (C) STRANDEDNESS: single
          (D) TOPOLOGY: linear (xi) SEQUENCE DESCRIPTION: SEQ ID NO:3:

Lys Leu Ile Val Thr Ser Ala Thr Met Asp Ala Glu Lys
1               5                   10

(2) INFORMATION FOR SEQ ID NO:4:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO:4:

Asp Ala Thr Ser Asp Leu Ala Ile Ile Ala Arg Lys
1               5                   10

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:5:

Lys Ile Phe Gln Lys
1               5

(2) INFORMATION FOR SEQ ID NO:6:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:6:

Thr Pro Gln Glu Asp Tyr Val Glu Ala Ala Val
1               5                   10

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:7:

ATGGGNGTNA ARAARGG                                              17

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:8:

GATATYATSG GNGTNAA                                              17

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single (D) TOPOLOGY: linear (xi) SEQUENCE DESCRIPTION: SEQ ID NO:9:

ATGGTNGTNA ARAARGARAC                                                  20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:10:

AARGARACNG ARCCNGAYAA                                                  20

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:11:

RTCCATNGTN GCNGANGT                                                    18

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:12:

NGTAGCNGAN GTNACNAT                                                    18

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:13:

TGTGATCTGC AAACATCTGC ACTGTCC                                          27

(2) INFORMATION FOR SEQ ID NO:14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:14:

GCCGGTGATT GCCAGTGAAG GATGCCA                                          27

(2) INFORMATION FOR SEQ ID NO:15:

(i) SEQUENCE CHARACTERISTICS:
        (A) LENGTH: 612 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..612

(ix) FEATURE:
        (A) NAME/KEY: mat_peptide
        (B) LOCATION: 1..612

(xi) SEQUENCE DESCRIPTION: SEQ ID NO:15:

```
AAG GAG ACG GAG CCG GAC AAA GCT ATG ACA GAA GAC GGG AAA GTG GAC       48
Lys Glu Thr Glu Pro Asp Lys Ala Met Thr Glu Asp Gly Lys Val Asp
 1               5                  10                  15

TAC AGG ACG GAG CAG AAG TTT GCA GAT CAC ATG AAG GAG AAA AGC GAG       96
Tyr Arg Thr Glu Gln Lys Phe Ala Asp His Met Lys Glu Lys Ser Glu
                20                  25                  30

GCC AGC AGT GAG TTT GCC AAG AAG AAG TCG ATC CTG GAG CAG AGG CAG      144
Ala Ser Ser Glu Phe Ala Lys Lys Lys Ser Ile Leu Glu Gln Arg Gln
            35                  40                  45

TAC CTG CCC ATC TTT GCC GTG CAG CAG GAG CTC GTC ACC ATC ATC AGA      192
Tyr Leu Pro Ile Phe Ala Val Gln Gln Glu Leu Val Thr Ile Ile Arg
50                  55                  60

GAC AAC AGC ATT GTG GTC GTG GTC GGG GAG ACA GGG AGT GGC AAG ACC      240
Asp Asn Ser Ile Val Val Val Val Gly Glu Thr Gly Ser Gly Lys Thr
 65                  70                  75                  80

ACT CAG CTG ACC CAG TAC TTG CAT GAA GAT GGT TAC ACG GAC TAT GGG      288
Thr Gln Leu Thr Gln Tyr Leu His Glu Asp Gly Tyr Thr Asp Tyr Gly
                 85                  90                  95

ATG ATC GGG TGT ACC CAG CCC CGG CGT GTG GCT GCC ATG TCA GCG GCC      336
Met Ile Gly Cys Thr Gln Pro Arg Arg Val Ala Ala Met Ser Ala Ala
            100                 105                 110

AAG AGA GTC AGT GAA GAG ATG GGG GGC AAC CTT GGA GAA GAG GTG GGC      384
Lys Arg Val Ser Glu Glu Met Gly Gly Asn Leu Gly Glu Glu Val Gly
        115                 120                 125

TAT GCC ATC CGC TTT GAG GAC TGC ACT TCG GAA AAC AAC TTG ATC AAG      432
Tyr Ala Ile Arg Phe Glu Asp Cys Thr Ser Glu Asn Asn Leu Ile Lys
    130                 135                 140

TAC ATG ACG GAT GGG ATC CTG CTC CGC GAG TCC CTC CGG CAG GCT GAC      480
Tyr Met Thr Asp Gly Ile Leu Leu Arg Glu Ser Leu Arg Gln Ala Asp
145                 150                 155                 160

CTG GAC CAC TAC AGC GCC GTC ATC ATG GAT GAG GCC CAC GAG CGC TCC      528
Leu Asp His Tyr Ser Ala Val Ile Met Asp Glu Ala His Glu Arg Ser
                165                 170                 175

CTC AAC ACC GAC GTG CTT TTT GGG CTG CTC CGG GAG GTT GTG GCT CGA      576
Leu Asn Thr Asp Val Leu Phe Gly Leu Leu Arg Glu Val Val Ala Arg
            180                 185                 190

GGC TCA GAC CTG AAG CTC ATG GTT ACA TCG GCT ACT                      612
Gly Ser Asp Leu Lys Leu Met Val Thr Ser Ala Thr
        195                 200
```

(2) INFORMATION FOR SEQ ID NO:16:

(i) SEQUENCE CHARACTERISTICS:
        (A) LENGTH: 204 amino acids
        (B) TYPE: amino acid
        (D) TOPOLOGY: linear (ii) MOLECULE TYPE: protein (xi) SEQUENCE DESCRIPTION: SEQ ID NO:16:

```
Lys Glu Thr Glu Pro Asp Lys Ala Met Thr Glu Asp Gly Lys Val Asp
 1               5                  10                  15

Tyr Arg Thr Glu Gln Lys Phe Ala Asp His Met Lys Glu Lys Ser Glu
                20                  25                  30
```

```
Ala Ser Ser Glu Phe Ala Lys Lys Ser Ile Leu Glu Gln Arg Gln
         35                  40                  45

Tyr Leu Pro Ile Phe Ala Val Gln Gln Glu Leu Val Thr Ile Ile Arg
 50                  55                  60

Asp Asn Ser Ile Val Val Val Gly Glu Thr Gly Ser Gly Lys Thr
 65                  70                  75                  80

Thr Gln Leu Thr Gln Tyr Leu His Glu Asp Gly Tyr Thr Asp Tyr Gly
                 85                  90                  95

Met Ile Gly Cys Thr Gln Pro Arg Arg Val Ala Ala Met Ser Ala Ala
                100                 105                 110

Lys Arg Val Ser Glu Glu Met Gly Gly Asn Leu Gly Glu Glu Val Gly
                115                 120                 125

Tyr Ala Ile Arg Phe Glu Asp Cys Thr Ser Glu Asn Asn Leu Ile Lys
                130                 135                 140

Tyr Met Thr Asp Gly Ile Leu Leu Arg Glu Ser Leu Arg Gln Ala Asp
145                 150                 155                 160

Leu Asp His Tyr Ser Ala Val Ile Met Asp Glu Ala His Glu Arg Ser
                165                 170                 175

Leu Asn Thr Asp Val Leu Phe Gly Leu Leu Arg Glu Val Val Ala Arg
                180                 185                 190

Gly Ser Asp Leu Lys Leu Met Val Thr Ser Ala Thr
                195                 200
```

(2) INFORMATION FOR SEQ ID NO:17:

(i) SEQUENCE CHARACTERISTICS:
        (A) LENGTH: 3684 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..3681

(ix) FEATURE:
        (A) NAME/KEY: mat_peptide
        (B) LOCATION: 1..3681

(xi) SEQUENCE DESCRIPTION: SEQ ID NO:17:

```
ATG GGG GAC ACC AGT GAG GAT GCC TCG ATC CAT CGA TTG GAA GGC ACT      48
Met Gly Asp Thr Ser Glu Asp Ala Ser Ile His Arg Leu Glu Gly Thr
 1               5                  10                  15

GAT CTG GAC TGT CAG GTT GGT GGT CTT ATT TGC AAG TCC AAA AGT GCG      96
Asp Leu Asp Cys Gln Val Gly Gly Leu Ile Cys Lys Ser Lys Ser Ala
                 20                  25                  30

GCC AGC GAG CAG CAT GTC TTC AAG GCT CCT GCT CCC CGC CCT TCA TTA     144
Ala Ser Glu Gln His Val Phe Lys Ala Pro Ala Pro Arg Pro Ser Leu
         35                  40                  45

CTC GGA CTG GAC TTG CTG GCT TCC CTG AAA CGG AGA GAG CGA GAG GAG     192
Leu Gly Leu Asp Leu Leu Ala Ser Leu Lys Arg Arg Glu Arg Glu Glu
 50                  55                  60

AAG GAC GAT GGG GAG GAC AAG AAG AAG TCC AAA GTC TCC TCC TAC AAG     240
Lys Asp Asp Gly Glu Asp Lys Lys Lys Ser Lys Val Ser Ser Tyr Lys
 65                  70                  75                  80

GAC TGG GAA GAG AGC AAG GAT GAC CAG AAG GAT GCT GAG GAA GAG GGC     288
Asp Trp Glu Glu Ser Lys Asp Asp Gln Lys Asp Ala Glu Glu Glu Gly
                 85                  90                  95

GGT GAC CAG GCT GGC CAA AAT ATC CGG AAA GAC AGA CAT TAT CGG TCT     336
Gly Asp Gln Ala Gly Gln Asn Ile Arg Lys Asp Arg His Tyr Arg Ser
                100                 105                 110
```

| | | | | | | | | | | | | | | | |
|---|---|---|---|---|---|---|---|---|---|---|---|---|---|---|---|
| GCT | CGG | GTA | GAG | ACT | CCA | TCC | CAT | CCG | GGT | GGT | GTG | AGC | GAA | GAG | TTT | 384
| Ala | Arg | Val | Glu | Thr | Pro | Ser | His | Pro | Gly | Gly | Val | Ser | Glu | Glu | Phe |
| | | 115 | | | | 120 | | | | | 125 | | | | |

```
GCT CGG GTA GAG ACT CCA TCC CAT CCG GGT GGT GTG AGC GAA GAG TTT      384
Ala Arg Val Glu Thr Pro Ser His Pro Gly Gly Val Ser Glu Glu Phe
        115                 120                 125

TGG GAA CGC AGT CGG CAG AGA GAG CGG GAG CGG CGG GAA CAT GGT GTC      432
Trp Glu Arg Ser Arg Gln Arg Glu Arg Glu Arg Arg Glu His Gly Val
130                 135                 140

TAT GCC TCG TCC AAA GAA GAA AAG GAT TGG AAG AAG GAG AAA TCG CGG      480
Tyr Ala Ser Ser Lys Glu Glu Lys Asp Trp Lys Lys Glu Lys Ser Arg
145                 150                 155                 160

GAT CGA GAC TAT GAC CGC AAG AGG GAC AGA GAT GAG CGG GAT AGA AGT      528
Asp Arg Asp Tyr Asp Arg Lys Arg Asp Arg Asp Glu Arg Asp Arg Ser
                    165                 170                 175

AGG CAC AGC AGC AGA TCA GAG CGA GAT GGA GGG TCA GAG CGT AGC AGC      576
Arg His Ser Ser Arg Ser Glu Arg Asp Gly Gly Ser Glu Arg Ser Ser
                180                 185                 190

AGA AGA AAT GAA CCC GAG AGC CCA CGA CAT CGA CCT AAA GAT GCA GCC      624
Arg Arg Asn Glu Pro Glu Ser Pro Arg His Arg Pro Lys Asp Ala Ala
            195                 200                 205

ACC CCT TCA AGG TCT ACC TGG GAG GAA GAG GAC AGT GGC TAT GGC TCC      672
Thr Pro Ser Arg Ser Thr Trp Glu Glu Glu Asp Ser Gly Tyr Gly Ser
        210                 215                 220

TCA AGG CGC TCA CAG TGG GAA TCG CCC TCC CCG ACG CCT TCC TAT CGG      720
Ser Arg Arg Ser Gln Trp Glu Ser Pro Ser Pro Thr Pro Ser Tyr Arg
225                 230                 235                 240

GAT TCT GAG CGG AGC CAT CGG CTG TCC ACT CGA GAT CGA GAC AGG TCT      768
Asp Ser Glu Arg Ser His Arg Leu Ser Thr Arg Asp Arg Asp Arg Ser
                    245                 250                 255

GTG AGG GGC AAG TAC TCG GAT GAC ACG CCT CTG CCA ACT CCC TCC TAC      816
Val Arg Gly Lys Tyr Ser Asp Asp Thr Pro Leu Pro Thr Pro Ser Tyr
                260                 265                 270

AAA TAT AAC GAG TGG GCC GAT GAC AGA AGA CAC TTG GGG TCC ACC CCG      864
Lys Tyr Asn Glu Trp Ala Asp Asp Arg Arg His Leu Gly Ser Thr Pro
            275                 280                 285

CGT CTG TCC AGG GGC CGA GGA AGA CGT GAG GAG GGC GAA GAA GGA ATT      912
Arg Leu Ser Arg Gly Arg Gly Arg Arg Glu Glu Gly Glu Glu Gly Ile
        290                 295                 300

TCA TTT GAC ACG GAG GAG GAG CGG CAG CAG TGG GAA GAT GAC CAG AGG      960
Ser Phe Asp Thr Glu Glu Glu Arg Gln Gln Trp Glu Asp Asp Gln Arg
305                 310                 315                 320

CAA GCC GAT CGG GAT TGG TAC ATG ATG GAC GAG GGC TAT GAC GAG TTC     1008
Gln Ala Asp Arg Asp Trp Tyr Met Met Asp Glu Gly Tyr Asp Glu Phe
                325                 330                 335

CAC AAC CCG CTG GCC TAC TCC TCC GAG GAC TAC GTG AGG AGG CGG GAG     1056
His Asn Pro Leu Ala Tyr Ser Ser Glu Asp Tyr Val Arg Arg Arg Glu
                340                 345                 350

CAG CAC CTG CAT AAA CAG AAG CAG AAG CGC ATT TCA GCT CAG CGG AGA     1104
Gln His Leu His Lys Gln Lys Gln Lys Arg Ile Ser Ala Gln Arg Arg
        355                 360                 365

CAG ATC AAT GAG GAT AAC GAG CGC TGG GAG ACA AAC CGC ATG CTC ACC     1152
Gln Ile Asn Glu Asp Asn Glu Arg Trp Glu Thr Asn Arg Met Leu Thr
370                 375                 380

AGT GGG GTG GTC CAT CGG CTG GAG GTG GAT GAG GAC TTT GAA GAG GAC     1200
Ser Gly Val Val His Arg Leu Glu Val Asp Glu Asp Phe Glu Glu Asp
385                 390                 395                 400

AAC GCG GCC AAG GTG CAT CTG ATG GTG CAC AAT CTG GTG CCT CCC TTT     1248
Asn Ala Ala Lys Val His Leu Met Val His Asn Leu Val Pro Pro Phe
                    405                 410                 415

CTG GAT GGG CGC ATT GTC TTC ACC AAG CAG CCG GAG CCG GTG ATT CCA     1296
Leu Asp Gly Arg Ile Val Phe Thr Lys Gln Pro Glu Pro Val Ile Pro
                420                 425                 430
```

-continued

| | | |
|---|---|---|
| GTG AAG GAT GCT ACT TCT GAC CTG GCC ATC ATT GCT CGG AAA GGC AGC<br>Val Lys Asp Ala Thr Ser Asp Leu Ala Ile Ile Ala Arg Lys Gly Ser<br>435 440 445 | | 1344 |
| CAG ACA GTG CGG AAG CAC AGG GAG CAG AAG GAG CGC AAG AAG GCT CAG<br>Gln Thr Val Arg Lys His Arg Glu Gln Lys Glu Arg Lys Lys Ala Gln<br>450 455 460 | | 1392 |
| CAC AAA CAC TGG GAA CTG GCG GGG ACC AAA CTG GGA GAT ATA ATG GGC<br>His Lys His Trp Glu Leu Ala Gly Thr Lys Leu Gly Asp Ile Met Gly<br>465 470 475 480 | | 1440 |
| GTC AAG AAG GAG GAA GAG CCA GAT AAA GCT GTG ACG GAG GAT GGG AAG<br>Val Lys Lys Glu Glu Glu Pro Asp Lys Ala Val Thr Glu Asp Gly Lys<br>485 490 495 | | 1488 |
| GTG GAC TAC AGG ACA GAG CAG AAG TTT GCA GAT CAC ATG AAG AGA AAG<br>Val Asp Tyr Arg Thr Glu Gln Lys Phe Ala Asp His Met Lys Arg Lys<br>500 505 510 | | 1536 |
| AGC GAA GCC AGC AGT GAA TTT GCA AAG AAG AAG TCC ATC CTG GAG CAG<br>Ser Glu Ala Ser Ser Glu Phe Ala Lys Lys Lys Ser Ile Leu Glu Gln<br>515 520 525 | | 1584 |
| AGG CAG TAC CTG CCC ATC TTT GCA GTG CAG CAG GAG CTG CTC ACT ATT<br>Arg Gln Tyr Leu Pro Ile Phe Ala Val Gln Gln Glu Leu Leu Thr Ile<br>530 535 540 | | 1632 |
| ATC AGA GAC AAC AGC ATC GTG ATC GTG GTT GGG GAG ACG GGG AGT GGT<br>Ile Arg Asp Asn Ser Ile Val Ile Val Val Gly Glu Thr Gly Ser Gly<br>545 550 555 560 | | 1680 |
| AAG ACC ACT CAG CTG ACG CAG TAC CTG CAT GAA GAT GGT TAC ACG GAC<br>Lys Thr Thr Gln Leu Thr Gln Tyr Leu His Glu Asp Gly Tyr Thr Asp<br>565 570 575 | | 1728 |
| TAT GGG ATG ATT GGG TGT ACC CAG CCC CGG CGT GTA GCT GCC ATG TCA<br>Tyr Gly Met Ile Gly Cys Thr Gln Pro Arg Arg Val Ala Ala Met Ser<br>580 585 590 | | 1776 |
| GTG GCC AAG AGA GTC AGT GAA GAG ATG GGG GGA AAC CTT GGC GAG GAG<br>Val Ala Lys Arg Val Ser Glu Glu Met Gly Gly Asn Leu Gly Glu Glu<br>595 600 605 | | 1824 |
| GTG GGC TAT GCC ATC CGC TTT GAA GAC TGC ACT TCA GAG AAC ACC TTG<br>Val Gly Tyr Ala Ile Arg Phe Glu Asp Cys Thr Ser Glu Asn Thr Leu<br>610 615 620 | | 1872 |
| ATC AAA TAC ATG ACT GAC GGG ATC CTG CTC CGA GAG TCC CTC CGG GAA<br>Ile Lys Tyr Met Thr Asp Gly Ile Leu Leu Arg Glu Ser Leu Arg Glu<br>625 630 635 640 | | 1920 |
| GCC GAC CTG GAT CAC TAC AGT GCC ATC ATC ATG GAC GAG GCC CAC GAG<br>Ala Asp Leu Asp His Tyr Ser Ala Ile Ile Met Asp Glu Ala His Glu<br>645 650 655 | | 1968 |
| CGC TCC CTC AAC ACT GAC GTG CTC TTT GGG CTG CTC CGG GAG GTA GTG<br>Arg Ser Leu Asn Thr Asp Val Leu Phe Gly Leu Leu Arg Glu Val Val<br>660 665 670 | | 2016 |
| GCT CGG CGC TCA GAC CTG AAG CTC ATC GTC ACA TCA GCC ACG ATG GAT<br>Ala Arg Arg Ser Asp Leu Lys Leu Ile Val Thr Ser Ala Thr Met Asp<br>675 680 685 | | 2064 |
| GCG GAG AAG TTT GCT GCC TTT TTT GGG AAT GTC CCC ATC TTC CAC ATC<br>Ala Glu Lys Phe Ala Ala Phe Phe Gly Asn Val Pro Ile Phe His Ile<br>690 695 700 | | 2112 |
| CCT GGC CGT ACC TTC CCT GTT GAC ATC CTC TTC AGC AAG ACC CCA CAG<br>Pro Gly Arg Thr Phe Pro Val Asp Ile Leu Phe Ser Lys Thr Pro Gln<br>705 710 715 720 | | 2160 |
| GAG GAT TAC GTG GAG GCT GCA GTG AAG CAG TCC TTG CAG GTG CAC CTG<br>Glu Asp Tyr Val Glu Ala Ala Val Lys Gln Ser Leu Gln Val His Leu<br>725 730 735 | | 2208 |
| TCG GGG GCC CCT GGA GAC ATC CTT ATC TTC ATG CCT GGC CAA GAG GAC<br>Ser Gly Ala Pro Gly Asp Ile Leu Ile Phe Met Pro Gly Gln Glu Asp<br>740 745 750 | | 2256 |

```
ATT GAG GTG ACC TCA GAC CAG ATT GTG GAG CAT CTG GAG GAA CTG GAG      2304
Ile Glu Val Thr Ser Asp Gln Ile Val Glu His Leu Glu Glu Leu Glu
            755                 760                 765

AAC GCG CCT GCC CTG GCT GTG CTG CCC ATC TAC TCT CAG CTG CCT TCT      2352
Asn Ala Pro Ala Leu Ala Val Leu Pro Ile Tyr Ser Gln Leu Pro Ser
        770                 775                 780

GAC CTC CAG GCC AAA ATC TTC CAG AAG GCT CCA GAT GGC GTT CGG AAG      2400
Asp Leu Gln Ala Lys Ile Phe Gln Lys Ala Pro Asp Gly Val Arg Lys
785                 790                 795                 800

TGC ATC GTT GCC ACC AAT ATT GCC GAG ACG TCT CTC ACT GTT GAC GGC      2448
Cys Ile Val Ala Thr Asn Ile Ala Glu Thr Ser Leu Thr Val Asp Gly
                805                 810                 815

ATC ATG TTT GTT ATC GAT TCT GGT TAT TGC AAA TTA AAG GTC TTC AAC      2496
Ile Met Phe Val Ile Asp Ser Gly Tyr Cys Lys Leu Lys Val Phe Asn
            820                 825                 830

CCC AGG ATT GGC ATG GAT GCT CTG CAG ATC TAT CCC ATT AGC CAG GCC      2544
Pro Arg Ile Gly Met Asp Ala Leu Gln Ile Tyr Pro Ile Ser Gln Ala
        835                 840                 845

AAT GCC AAC CAG CGG TCA GGG CGA GCC GGC AGG ACG GGC CCA GGT CAG      2592
Asn Ala Asn Gln Arg Ser Gly Arg Ala Gly Arg Thr Gly Pro Gly Gln
850                 855                 860

TGT TTC AGG CTC TAC ACC CAG AGC GCC TAC AAG AAT GAG CTC CTG ACC      2640
Cys Phe Arg Leu Tyr Thr Gln Ser Ala Tyr Lys Asn Glu Leu Leu Thr
865                 870                 875                 880

ACC ACA GTG CCC GAG ATC CAG AGG ACT AAC CTG GCC AAC GTG GTG CTG      2688
Thr Thr Val Pro Glu Ile Gln Arg Thr Asn Leu Ala Asn Val Val Leu
                885                 890                 895

CTG CTC AAG TCC CTC GGG GTG CAG GAC CTG CTG CAG TTC CAC TTC ATG      2736
Leu Leu Lys Ser Leu Gly Val Gln Asp Leu Leu Gln Phe His Phe Met
            900                 905                 910

GAC CCG CCC CCG GAG GAC AAC ATG CTC AAC TCT ATG TAT CAG CTC TGG      2784
Asp Pro Pro Pro Glu Asp Asn Met Leu Asn Ser Met Tyr Gln Leu Trp
        915                 920                 925

ATC CTC GGG GCC CTG GAC AAC ACA GGT GGT CTG ACC TCT ACC GGG CGG      2832
Ile Leu Gly Ala Leu Asp Asn Thr Gly Gly Leu Thr Ser Thr Gly Arg
930                 935                 940

CTG ATG GTG GAG TTC CCG CTG GAC CCT GCC CTG TCC AAG ATG CTC ATC      2880
Leu Met Val Glu Phe Pro Leu Asp Pro Ala Leu Ser Lys Met Leu Ile
945                 950                 955                 960

GTG TCC TGT GAC ATG GGC TGC AGC TCC GAG ATC CTG CTC ATC GTT TCC      2928
Val Ser Cys Asp Met Gly Cys Ser Ser Glu Ile Leu Leu Ile Val Ser
                965                 970                 975

ATG CTC TCG GTC CCA GCC ATC TTC TAC AGG CCC AAG GGT CGA GAG GAG      2976
Met Leu Ser Val Pro Ala Ile Phe Tyr Arg Pro Lys Gly Arg Glu Glu
            980                 985                 990

GAG AGT GAT CAA ATC CGG GAG AAG TTC GCT GTT CCT GAG AGC GAT CAT      3024
Glu Ser Asp Gln Ile Arg Glu Lys Phe Ala Val Pro Glu Ser Asp His
        995                 1000                1005

TTG ACC TAC CTG AAT GTT TAC CTG CAG TGG AAG AAC AAT AAT TAC TCC      3072
Leu Thr Tyr Leu Asn Val Tyr Leu Gln Trp Lys Asn Asn Asn Tyr Ser
1010                1015                1020

ACC ATC TGG TGT AAC GAT CAT TTC ATC CAT GCT AAG GCC ATG CGG AAG      3120
Thr Ile Trp Cys Asn Asp His Phe Ile His Ala Lys Ala Met Arg Lys
1025                1030                1035                1040

GTC CGG GAG GTG CGA GCT CAA CTC AAG GAC ATC ATG GTG CAG CAG CGG      3168
Val Arg Glu Val Arg Ala Gln Leu Lys Asp Ile Met Val Gln Gln Arg
                1045                1050                1055

ATG AGC CTG GCC TCG TGT GGC ACT GAC TGG GAC ATC GTC AGG AAG TGC      3216
Met Ser Leu Ala Ser Cys Gly Thr Asp Trp Asp Ile Val Arg Lys Cys
            1060                1065                1070
```

```
ATC TGT GCT GCC TAT TTC CAC CAA GCA GCC AAG CTC AAG GGA ATC GGG        3264
Ile Cys Ala Ala Tyr Phe His Gln Ala Ala Lys Leu Lys Gly Ile Gly
    1075                1080                1085

GAG TAC GTG AAC ATC CGC ACA GGG ATG CCC TGC CAC TTG CAC CCC ACC        3312
Glu Tyr Val Asn Ile Arg Thr Gly Met Pro Cys His Leu His Pro Thr
        1090                1095                1100

AGC TCC CTT TTT GGA ATG GGC TAC ACC CCA GAT TAC ATA GTG TAT CAC        3360
Ser Ser Leu Phe Gly Met Gly Tyr Thr Pro Asp Tyr Ile Val Tyr His
1105                1110                1115                1120

GAG TTG GTC ATG ACC ACC AAG GAG TAT ATG CAG TGT GTG ACC GCT GTG        3408
Glu Leu Val Met Thr Thr Lys Glu Tyr Met Gln Cys Val Thr Ala Val
            1125                1130                1135

GAC GGG GAG TGG CTG GCG GAG CTG GGC CCC ATG TTC TAT AGC GTG AAA        3456
Asp Gly Glu Trp Leu Ala Glu Leu Gly Pro Met Phe Tyr Ser Val Lys
                1140                1145                1150

CAG GCG GGC AAG TCA CGG CAG GAG AAC CGT CGT CGG GCC AAA GAG GAA        3504
Gln Ala Gly Lys Ser Arg Gln Glu Asn Arg Arg Arg Ala Lys Glu Glu
                    1155                1160                1165

GCC TCT GCC ATG GAG GAG GAG ATG GCG CTG GCC GAG GAG CAG CTG CGA        3552
Ala Ser Ala Met Glu Glu Glu Met Ala Leu Ala Glu Glu Gln Leu Arg
1170                1175                1180

GCC CGG CGG CAG GAG CAG GAG AAG CGC AGC CCC CTG GGC AGT GTC AGG        3600
Ala Arg Arg Gln Glu Gln Glu Lys Arg Ser Pro Leu Gly Ser Val Arg
1185                1190                1195                1200

TCT ACG AAG ATC TAC ACT CCA GGC CGG AAA GAG CAA GGG GAG CCC ATG        3648
Ser Thr Lys Ile Tyr Thr Pro Gly Arg Lys Glu Gln Gly Glu Pro Met
        1205                1210                1215

ACC CCT CGC CGC ACG CCA GCC CGC TTT GGT CTG TGA                        3684
Thr Pro Arg Arg Thr Pro Ala Arg Phe Gly Leu
            1220                1225

(2) INFORMATION FOR SEQ ID NO:18:

(i) SEQUENCE CHARACTERISTICS:
        (A) LENGTH: 1227 amino acids
        (B) TYPE: amino acid
        (D) TOPOLOGY: linear (ii) MOLECULE TYPE: protein (xi) SEQUENCE DESCRIPTION: SEQ ID NO:18:

Met Gly Asp Thr Ser Glu Asp Ala Ser Ile His Arg Leu Glu Gly Thr
1               5                   10                  15

Asp Leu Asp Cys Gln Val Gly Gly Leu Ile Cys Lys Ser Lys Ser Ala
            20                  25                  30

Ala Ser Glu Gln His Val Phe Lys Ala Pro Ala Pro Arg Pro Ser Leu
        35                  40                  45

Leu Gly Leu Asp Leu Leu Ala Ser Leu Lys Arg Arg Glu Arg Glu Glu
    50                  55                  60

Lys Asp Asp Gly Glu Asp Lys Lys Ser Lys Val Ser Ser Tyr Lys
65                  70                  75                  80

Asp Trp Glu Glu Ser Lys Asp Gln Lys Asp Ala Glu Glu Gly
                85                  90                  95

Gly Asp Gln Ala Gly Gln Asn Ile Arg Lys Asp Arg His Tyr Arg Ser
            100                 105                 110

Ala Arg Val Glu Thr Pro Ser His Pro Gly Gly Val Ser Glu Glu Phe
        115                 120                 125

Trp Glu Arg Ser Arg Gln Arg Gly Arg Glu Arg Glu His Gly Val
    130                 135                 140

Tyr Ala Ser Ser Lys Glu Glu Lys Asp Trp Lys Lys Glu Lys Ser Arg
```

```
                145                 150                 155                 160
Asp Arg Asp Tyr Asp Arg Lys Arg Asp Arg Asp Glu Arg Asp Arg Ser
                    165                 170                 175
Arg His Ser Ser Arg Ser Glu Arg Asp Gly Gly Ser Glu Arg Ser Ser
                    180                 185                 190
Arg Arg Asn Glu Pro Glu Ser Pro Arg His Arg Pro Lys Asp Ala Ala
                    195                 200                 205
Thr Pro Ser Arg Ser Thr Trp Glu Glu Asp Ser Gly Tyr Gly Ser
    210                 215                 220
Ser Arg Arg Ser Gln Trp Glu Ser Pro Ser Pro Thr Pro Ser Tyr Arg
225                 230                 235                 240
Asp Ser Glu Arg Ser His Arg Leu Ser Thr Arg Asp Arg Asp Arg Ser
                    245                 250                 255
Val Arg Gly Lys Tyr Ser Asp Asp Thr Pro Leu Pro Thr Pro Ser Tyr
                    260                 265                 270
Lys Tyr Asn Glu Trp Ala Asp Asp Arg Arg His Leu Gly Ser Thr Pro
                    275                 280                 285
Arg Leu Ser Arg Gly Arg Gly Arg Arg Glu Glu Gly Glu Gly Ile
    290                 295                 300
Ser Phe Asp Thr Glu Glu Glu Arg Gln Gln Trp Glu Asp Asp Gln Arg
305                 310                 315                 320
Gln Ala Asp Arg Asp Trp Tyr Met Met Asp Glu Gly Tyr Asp Glu Phe
                    325                 330                 335
His Asn Pro Leu Ala Tyr Ser Ser Glu Asp Tyr Val Arg Arg Arg Glu
                    340                 345                 350
Gln His Leu His Lys Gln Lys Gln Lys Arg Ile Ser Ala Gln Arg Arg
                    355                 360                 365
Gln Ile Asn Glu Asp Asn Glu Arg Trp Glu Thr Asn Arg Met Leu Thr
                    370                 375                 380
Ser Gly Val Val His Arg Leu Glu Val Asp Glu Asp Phe Glu Glu Asp
385                 390                 395                 400
Asn Ala Ala Lys Val His Leu Met Val His Asn Leu Val Pro Pro Phe
                    405                 410                 415
Leu Asp Gly Arg Ile Val Phe Thr Lys Gln Pro Glu Pro Val Ile Pro
                    420                 425                 430
Val Lys Asp Ala Thr Ser Asp Leu Ala Ile Ile Ala Arg Lys Gly Ser
                    435                 440                 445
Gln Thr Val Arg Lys His Arg Glu Gln Lys Glu Arg Lys Lys Ala Gln
                    450                 455                 460
His Lys His Trp Glu Leu Ala Gly Thr Lys Leu Gly Asp Ile Met Gly
465                 470                 475                 480
Val Lys Lys Glu Glu Glu Pro Asp Lys Ala Val Thr Glu Asp Gly Lys
                    485                 490                 495
Val Asp Tyr Arg Thr Glu Gln Lys Phe Ala Asp His Met Lys Arg Lys
                    500                 505                 510
Ser Glu Ala Ser Ser Glu Phe Ala Lys Lys Ser Ile Leu Glu Gln
                    515                 520                 525
Arg Gln Tyr Leu Pro Ile Phe Ala Val Gln Gln Glu Leu Leu Thr Ile
                    530                 535                 540
Ile Arg Asp Asn Ser Ile Val Ile Val Val Gly Glu Thr Gly Ser Gly
545                 550                 555                 560
Lys Thr Thr Gln Leu Thr Gln Tyr Leu His Glu Asp Gly Tyr Thr Asp
                    565                 570                 575
```

```
Tyr Gly Met Ile Gly Cys Thr Gln Pro Arg Val Ala Ala Met Ser
            580                 585                 590

Val Ala Lys Arg Val Ser Glu Glu Met Gly Gly Asn Leu Gly Glu Glu
        595                 600                 605

Val Gly Tyr Ala Ile Arg Phe Glu Asp Cys Thr Ser Glu Asn Thr Leu
610                 615                 620

Ile Lys Tyr Met Thr Asp Gly Ile Leu Leu Arg Glu Ser Leu Arg Glu
625                 630                 635                 640

Ala Asp Leu Asp His Tyr Ser Ala Ile Ile Met Asp Glu Ala His Glu
                645                 650                 655

Arg Ser Leu Asn Thr Asp Val Leu Phe Gly Leu Leu Arg Glu Val Val
                660                 665                 670

Ala Arg Arg Ser Asp Leu Lys Leu Ile Val Thr Ser Ala Thr Met Asp
            675                 680                 685

Ala Glu Lys Phe Ala Ala Phe Phe Gly Asn Val Pro Ile Phe His Ile
690                 695                 700

Pro Gly Arg Thr Phe Pro Val Asp Ile Leu Phe Ser Lys Thr Pro Gln
705                 710                 715                 720

Glu Asp Tyr Val Glu Ala Val Lys Gln Ser Leu Gln Val His Leu
                725                 730                 735

Ser Gly Ala Pro Gly Asp Ile Leu Ile Phe Met Pro Gly Gln Glu Asp
            740                 745                 750

Ile Glu Val Thr Ser Asp Gln Ile Val Glu His Leu Glu Glu Leu Glu
                755                 760                 765

Asn Ala Pro Ala Leu Ala Val Leu Pro Ile Tyr Ser Gln Leu Pro Ser
770                 775                 780

Asp Leu Gln Ala Lys Ile Phe Gln Lys Ala Pro Asp Gly Val Arg Lys
785                 790                 795                 800

Cys Ile Val Ala Thr Asn Ile Ala Glu Thr Ser Leu Thr Val Asp Gly
                805                 810                 815

Ile Met Phe Val Ile Asp Ser Gly Tyr Cys Lys Leu Lys Val Phe Asn
            820                 825                 830

Pro Arg Ile Gly Met Asp Ala Leu Gln Ile Tyr Pro Ile Ser Gln Ala
            835                 840                 845

Asn Ala Asn Gln Arg Ser Gly Arg Ala Gly Arg Thr Gly Pro Gly Gln
850                 855                 860

Cys Phe Arg Leu Tyr Thr Gln Ser Ala Tyr Lys Asn Glu Leu Leu Thr
865                 870                 875                 880

Thr Thr Val Pro Glu Ile Gln Arg Thr Asn Leu Ala Asn Val Val Leu
                885                 890                 895

Leu Leu Lys Ser Leu Gly Val Gln Asp Leu Leu Gln Phe His Phe Met
            900                 905                 910

Asp Pro Pro Pro Glu Asp Asn Met Leu Asn Ser Met Tyr Gln Leu Trp
            915                 920                 925

Ile Leu Gly Ala Leu Asp Asn Thr Gly Gly Leu Thr Ser Thr Gly Arg
930                 935                 940

Leu Met Val Glu Phe Pro Leu Asp Pro Ala Leu Ser Lys Met Leu Ile
945                 950                 955                 960

Val Ser Cys Asp Met Gly Cys Ser Ser Glu Ile Leu Leu Ile Val Ser
                965                 970                 975

Met Leu Ser Val Pro Ala Ile Phe Tyr Arg Pro Lys Gly Arg Glu Glu
            980                 985                 990

Glu Ser Asp Gln Ile Arg Glu Lys Phe Ala Val Pro Glu Ser Asp His
            995                 1000                1005
```

```
Leu Thr Tyr Leu Asn Val Tyr Leu Gln Trp Lys Asn Asn Asn Tyr Ser
        1010                1015                1020

Thr Ile Trp Cys Asn Asp His Phe Ile His Ala Lys Ala Met Arg Lys
1025                1030                1035                1040

Val Arg Glu Val Arg Ala Gln Leu Lys Asp Ile Met Val Gln Gln Arg
                1045                1050                1055

Met Ser Leu Ala Ser Cys Gly Thr Asp Trp Asp Ile Val Arg Lys Cys
        1060                1065                1070

Ile Cys Ala Ala Tyr Phe His Gln Ala Ala Lys Leu Lys Gly Ile Gly
        1075                1080                1085

Glu Tyr Val Asn Ile Arg Thr Gly Met Pro Cys His Leu His Pro Thr
        1090                1095                1100

Ser Ser Leu Phe Gly Met Gly Tyr Thr Pro Asp Tyr Ile Val Tyr His
1105                1110                1115                1120

Glu Leu Val Met Thr Thr Lys Glu Tyr Met Gln Cys Val Thr Ala Val
                1125                1130                1135

Asp Gly Glu Trp Leu Ala Glu Leu Gly Pro Met Phe Tyr Ser Val Lys
        1140                1145                1150

Gln Ala Gly Lys Ser Arg Gln Glu Asn Arg Arg Ala Lys Glu Glu
        1155                1160                1165

Ala Ser Ala Met Glu Glu Met Ala Leu Ala Glu Glu Gln Leu Arg
        1170                1175                1180

Ala Arg Arg Gln Glu Gln Glu Lys Arg Ser Pro Leu Gly Ser Val Arg
1185                1190                1195                1200

Ser Thr Lys Ile Tyr Thr Pro Gly Arg Lys Glu Gln Gly Glu Pro Met
                1205                1210                1215

Thr Pro Arg Arg Thr Pro Ala Arg Phe Gly Leu
        1220                1225

(2) INFORMATION FOR SEQ ID NO:19:

(i) SEQUENCE CHARACTERISTICS:
        (A) LENGTH: 43 amino acids
        (B) TYPE: amino acid
        (C) STRANDEDNESS: single
        (D) TOPOLOGY: linear (xi) SEQUENCE DESCRIPTION: SEQ ID NO:19:

Ala Xaa Xaa Xaa Gly Lys Thr Pro Thr Arg Glu Leu Ala Gly Gly Thr
1               5                   10                  15

Pro Gly Arg Asp Glu Ala Asp Ser Ala Thr Phe Xaa Xaa Xaa Thr Arg
                20                  25                  30

Gly Xaa Asp His Arg Ile Gly Arg Xaa Xaa Arg
        35                  40

(2) INFORMATION FOR SEQ ID NO:20:

(i) SEQUENCE CHARACTERISTICS:
        (A) LENGTH: 43 amino acids
        (B) TYPE: amino acid
        (C) STRANDEDNESS: single
        (D) TOPOLOGY: linear (xi) SEQUENCE DESCRIPTION: SEQ ID NO:20:

Ala Xaa Xaa Xaa Xaa Gly Lys Thr Pro Thr Arg Glu Leu Ala Gly Gly
1               5                   10                  15

Thr Pro Gly Arg Asp Glu Ala Asp Ser Ala Thr Phe Ile Asn Thr Arg
                20                  25                  30
```

```
Gly Ile Asp His Arg Ile Gly Arg Xaa Xaa Arg
        35                  40
```

(2) INFORMATION FOR SEQ ID NO:21:

(i) SEQUENCE CHARACTERISTICS:
        (A) LENGTH: 40 amino acids
        (B) TYPE: amino acid
        (C) STRANDEDNESS: single
        (D) TOPOLOGY: linear (xi) SEQUENCE DESCRIPTION: SEQ ID NO:21:

```
Gly Xaa Xaa Xaa Xaa Gly Lys Thr Arg Val Ala Ala Xaa Xaa Thr Asp
1               5                   10                  15

Gly Xaa Asp Glu Ala His Ser Ala Thr Phe Xaa Thr Xaa Gly Xaa Xaa
            20                  25                  30

Gln Arg Ile Gly Arg Xaa Gly Arg
        35                  40
```

(2) INFORMATION FOR SEQ ID NO:22:

(i) SEQUENCE CHARACTERISTICS:
        (A) LENGTH: 37 amino acids
        (B) TYPE: amino acid
        (C) STRANDEDNESS: single
        (D) TOPOLOGY: linear (xi) SEQUENCE DESCRIPTION: SEQ ID NO:22:

```
Xaa Xaa Xaa Xaa Xaa Gly Lys Thr Pro Thr Arg Xaa Xaa Xaa Asp Glu
1               5                   10                  15

Xaa His Thr Ala Thr Phe Xaa Xaa Ser Xaa Gly Xaa Xaa Gln Arg Xaa
            20                  25                  30

Gly Arg Xaa Gly Arg
        35
```

(2) INFORMATION FOR SEQ ID NO:23:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:23:

```
Ala Xaa Xaa Xaa Xaa Gly Lys Thr
1               5
```

(2) INFORMATION FOR SEQ ID NO:24:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:24:

```
His Arg Ile Gly Arg Xaa Xaa Arg
1               5
```

(2) INFORMATION FOR SEQ ID NO:25:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:25:

Gln Arg Ser Gly Arg Xaa Gly Arg
1               5

(2) INFORMATION FOR SEQ ID NO:26:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:26:

Gln Arg Ile Gly Arg Xaa Gly Arg
1               5

(2) INFORMATION FOR SEQ ID NO:27:

(i) SEQUENCE CHARACTERISTICS:
        (A) LENGTH: 51 amino acids
        (B) TYPE: amino acid
        (C) STRANDEDNESS: single
        (D) TOPOLOGY: linear (xi) SEQUENCE DESCRIPTION: SEQ ID NO:27:

Glu Asp Lys Lys Lys Ser Lys Val Ser Gly Glu Thr Gly Ser Gly Lys
1               5                   10                  15

Thr Pro Arg Arg Val Ala Ala Ser Glu Thr Asp Gly Ile Asp Glu Ala
                20                  25                  30

His Ser Ala Thr Phe Met Pro Ser Gly Tyr Cys Gln Arg Ser Gly Arg
                35                  40                  45

Ala Gly Arg
    50

(2) INFORMATION FOR SEQ ID NO:28:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:28:

Met Gly Val Lys Lys
1               5

(2) INFORMATION FOR SEQ ID NO:29:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:29:

Asp Ile Met Gly Val
1               5

(2) INFORMATION FOR SEQ ID NO:30:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:30:

```
Met Gly Val Lys Lys Glu
1               5
```

(2) INFORMATION FOR SEQ ID NO:31:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:31:

```
Lys Glu Thr Glu Pro Asp
1               5
```

(2) INFORMATION FOR SEQ ID NO:32:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:32:

```
Thr Ser Ala Thr Met Asp
1               5
```

(2) INFORMATION FOR SEQ ID NO:33:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:33:

```
Ile Val Thr Ser Ala Thr
1               5
```

(2) INFORMATION FOR SEQ ID NO:34:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:34:

```
Lys Leu Gly Asp Ile Met Gly Val Lys Lys
1               5                   10
```

(2) INFORMATION FOR SEQ ID NO:35:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:35:

```
Asp Glu Ala Asp
1
```

(2) INFORMATION FOR SEQ ID NO:36:

(i) SEQUENCE CHARACTERISTICS:

```
            (A) LENGTH: 4 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:36:

Asp Glu Ala His
1

(2) INFORMATION FOR SEQ ID NO:37:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:37:

Asp Glu Xaa His
1

(2) INFORMATION FOR SEQ ID NO:38:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:38:

Asp Glu Xaa Xaa
```

DEAH-BOX PROTEINS

BACKGROUND OF THE INVENTION

The modulation of RNA structure is an essential regulatory process in many cellular events, such as, for example, pre-mRNA splicing, assembly of spliceosomes, assembly of ribosomes, protein translation, which can be summarized under the generic term "regulation of gene expression at the RNA level". The so-called "DEAD box" protein family of putative RNA helicases, named after the characteristic amino acid motif Asp-Glu-Ala-Asp (in the single-letter code DEAD) (SEQ ID NO:35), in this context plays a key part (in particular for the modulation of the secondary and tertiary structure of mRNA). DEAD box proteins are also involved in processing of DNA. The members of this family and some subfamilies have differences in their specific function and cellular localization. However, in addition to characteristic sequence homologies certain members also show similar biochemical properties (F. V. Fuller-Pace, Trends in Cell Biology, Vol 4, 1994, 271–274). The characteristic protein sequences of the DEAD proteins are highly conserved in evolution (S. R. Schmid and P. Lindner, Molecular and Cellular Biology, Vol 11, 1991, 3463–3471). Members of this protein family are found in various viruses, bacteria, yeasts, insects, molluscs and lower vertebrates up to mammals and are responsible for a large number of cellular functions. The fact that even relatively simple organisms such as, for example, the yeast *Saccharomyces cerevisiae* express numerous proteins of the DEAD box protein family and their subfamilies, suggests that each of these proteins contributes to the specific interaction with certain RNAs or RNA families (I. Iost and M. Dreyfus, Nature Vol 372, 1994, 193–196). It has been shown that translation factors, such as eIF-4A and the proteins involved in the pre-mRNA splicing process, recognize specific RNA target sequences or structures. Nevertheless, to date there is little information about the structure and the synthesis of characteristic RNA sequences which require the DEAD proteins for recognition and for ATPase/RNA helicase reaction (A. Pause and N. Sonenberg, Current Opinion in Structural Biology Vol 3, 1993, 953–959).

The DEAD box protein family is an enzyme class which is growing and which is involved in the various reactions in post transcriptional regulation of gene expression. Because of the high number of different cellular DEAD box proteins, it is to be expected that specific RNA helicases are assigned to certain classes of gene products, e.g. viral proteins, heat shock proteins, antibody and MHC proteins, receptors, RNAs etc. This specificity indicates that members of this protein family are attractive pharmacological targets for active compound development.

Two of the subclasses of the DEAD (SEQ ID NO:35) box protein family are the DEAH (SEQ ID NO:36) proteins (having one specific amino acid replacement) and the DEXH (SEQ ID NO:37) protein (having two amino acid replacements in the main motif, X being any desired amino acid) families, which also play a part in the replication, recombination, repair and expression of DNA and RNA genomes (Gorbalenya, A. E., Koonin, E. V., Dochenko, A. P., Blinov, V. M., 1989: Nucleic Acids Res. 17, 4713–4729). The DEAD box proteins and their subfamilies are often designated "helicase superfamily II" (Koonin, E. V., Gorbalenya, A. E., 1992: FEBS 298, 6–8). This superfamily has seven highly conserved regions. Altogether, up to now over 70 members belong to this superfamily II.

The following schematic representation of the DEAD family and the DEAH and DEXH families subfamilies (Schmid, S. R., Lindner P., 1991: Molecular and Cellular Biology 11, 3463–3471) shows the similarity between the families. The structure of eIF-4A, a member of a DEAD box protein, is also shown. The numbers between these regions show the distances in amino acids (AA). X is any desired AA. Where known, functions have been assigned to the ranges.

```
DEAD (SEQ ID NO:35) FAMILY

ATPase A motif                      ATPase B motif
NH2-----AXXXGKT----PTRELA-----GG---TPGR---DEAD---SAT---FXXXT---
    21-299        24-42       22-28 19-27  19-22  27-51  59-70      52-53

RGXD-----HRIGRXXR---COOH (SEQ ID NO:19)
    20         24-236 eIF-4A

NH2-----AXXXXGKT---PTRELA-----GG---TPGR---DEAD---SAT---FINT---
     75           24           22    20     20    27    62    52

RGID------HRIGRXXR---COOH (SEQ ID NO:20)
     20             41

DEAH (SEQ ID NO:36) SUBFAMILY

NH2-----GXXXXGKT---RVAA-----XX---TDGX---DEAH---SAT---FXT---
    245-505       22-24     29   7-8    19     28    58-61    75-84

XGXX------QRIGRXGR---COOH (SEQ ID NO:21)
     25             315-373

DEXH (SEQ-ID NO:37) SUBFAMILY

NH2-----XXXXXGKT---PTRXXX---------------DEXH---TAT---FXXS---
    81-1904         19-27    55-60              24-30  44-72
    46-55
XGXX------QRXGRXGR---COOH (SEQ ID NO:22)
     38-44          155-1799
```

The ATPase motif (AXXXXGKT, SEQ ID NO:23) is an amino-terminal conserved region and occurs in most proteins which bind nucleotides, i.e. also in other proteins which interact with DNA and RNA, such as DNAB (part of the primosome), UvrD (endonuclease), elongation factor 1 and transcription termination factor Rho (Ford M. J., Anton, I. A., Lane, D. P., 1988: Nature 332, 736–738). As used in this specification "ATPase activity" is used to mean the ability to catalyze hydrolysis of ATP. The ATPase A and ATPase B motifs function together in the enzymatic process of ATP hydrolysis.

The second conserved region is the so-called DEAD (SEQ ID NO:35) box, or DEAH (SEQ ID NO:36), DEXH (SEQ ID NO:37) or DEXX (SEQ ID NO:38) box in other families of the helicases and nucleic acid-dependent ATPases. This region represents the ATPase B motif. In the reaction mechanism, the N-terminal aspartic acid in the DEAD box binds $Mg^{2+}$ via a water molecule (Pai, E. F., Krengel, U., Petsko, G. A., Gody, R. S., Katsch, W., Wittinghofer, A., 1990: EMBO J. 9, 2351–2359). $Mg^{2+}$ in turn forms a complex with the β- and gamma-phosphate of the nucleotide and is essential for the ATPase activity. Substitutions of the first two amino acids of the DEAD region in eIF-4A prevent ATP hydrolysis and RNA helicase activity, but not ATP binding (Pause, A., Sonenberg, N., 1992: EMBO J. 11, 2643–2654). The DEAD region additionally couples RNA helicase activity to ATPase activity. The hydrolysis of ATP provides the energy needed for RNA unwinding during helicase activity.

The third region investigated is the SAT region (sometimes also TAT). As a result of mutation in this region, RNA helicase activity is suppressed, but other biochemical properties are retained (Pause A. & Sonenberg N., 1992). As used in this specification "helicase activity" is used to mean the ability to directly or indirectly catalyze the unwinding of RNA.

The farthest carboxy-terminal region is the HRIGRXXR (SEQ ID NO:24) region, which is necessary for RNA binding and ATP hydrolysis.

As stated above, members of the DEAD box protein family bind ATP and nucleic acid. As used in this specification a protein that "binds nucleic acid" is defined as a protein that forms complexes with nucleic acid. The binding can be measured by standard methods like Electrophoretic Mobility Shift Assay (EMSA) or ELISA, which are well known in the art. The following assays may also be used: Scintillation Proximity Assay (SPA, Amersham International, Little Chalfont, Buckinghamshire, England) and BIAcore (Biomolecule Interaction Analysis, Pharmacia, Upsala Sweden).

As used in this specification, a protein that "binds ATP" is defined as a protein that will bind ATP as measured using an assay that measures ability of labeled ATP to bind to protein. The ATP may be labeled using radioactive or fluorescent label. One example of an ATP binding assay is described in Pause, et al. EMBO J. 11:2643 (1992), which is hereby incorporated by reference. Briefly, a protein according to the invention is incubated in a crosslinking reaction mixture containing Tris-HCl (pH 7.5), Mg acetate, $^{32}$P-ATP, glycerol and DTT in the presence or absence of poly(u) (Pharmacia) under a 15 watt germicidal lamp at 4° C. Unlabelled ATP is then added, followed by addition of RNase A at 37° C. Samples are boiled in SDS-PAGE sample buffer and electrophoresed.

It follows from the above-mentioned relationships that specific RNA helicases are attractive targets for pharmaceutically active substances. For example, it is also known that certain pathogenic viruses, which can cause diseases in humans, animals or plants, carry in their genome a gene encoding an RNA helicase, which is needed for accurate replication (E. V. Koonin, 1991). Thus, specific substances that interfere with, or modulate, the activity of such virus-specific helicases could be used to treat virally-mediated diseases. Because helicases are also found in plants, substances that modulate plant helicases may be used to protect plants against pathogenic viruses. (F. V. Fuller-Pace, Trends in Cell Biology, Vol. 4, 1994, 271–274). Helicases also make attractive targets for development of therapeutic treatments for various types of diseases. For example, hereditary diseases such as Werner's syndrome and Bloom's syndrome have been linked to the production of proteins with helicase structure. See Yu, et al. Science 272: 258 (1996) and Research News, Science 272: 193 (1 996)(Werner's); Ellis, et al. Cell 83:655 (1995), and D. Bassett "Genes of Medical Interest" In http://www.ncbi.nih.gov/xREFdb/(Bloom's). A nucleolar RNA helicase is recognized by the autoimmune antibodies from a patient with watermelon stomach. Valdez, et al., Nucl. Acid. Res., 24:1220 (1996). In retinoblastoma cancer cells, expression of a DEAD box protein is amplified. Godbout, et al. Proc. Natl. Acad. Sci. USA 90:7578 (1993). In addition, RNA processing plays a role in a number of processes that are implicated in other disease states. For example, in diabetic mice, the leptin receptor is abnormally spliced. Lee, et al. Nature 379:632 (1996). In addition, post-transcriptional regulation of human interleukin-2 gene expression occurs at the level of processing of precursor transcripts, which may be linked to the presence of a protein. Gerez, et al. J. Biol Chem. 270:19569 (1995).

Thus, therapeutic agents can be designed that interfere with helicase activity or RNA processing that is associated with the disease state.

The isoxazole derivative leflunomide shows anti-inflammatory and immunosuppressive properties without causing damage to the existing functions of the immune system (HWA486 (leflunomide); R. R. Bartlett, G. Campion, P. Musikic, T. Zielinski, H. U. Schorlemmer In: A. L. Lewis and D. E. Furst (editors), Nonsteroidal Anti-inflammatory Drugs, Mechanisms and Clinical Uses (Dekker: New York, 1994); C. C. A. Küchle, G. H. Thoenes, K. H. Langer, H. U. Schorlemmer, R. R. Bartlett, R. Schleyerbach, Transplant Proc. 1991, 23:1083–6; T. Zielinski, H. J. Müller, R. R. Bartlett, Agents Action 1993, 38: C80-2). Many activities, such as the modification of cell activation, proliferation, differentiation and cell cooperation, which can be observed in autoimmune diseases, are modulated by leflunomide or its active metabolite, A77 1726.

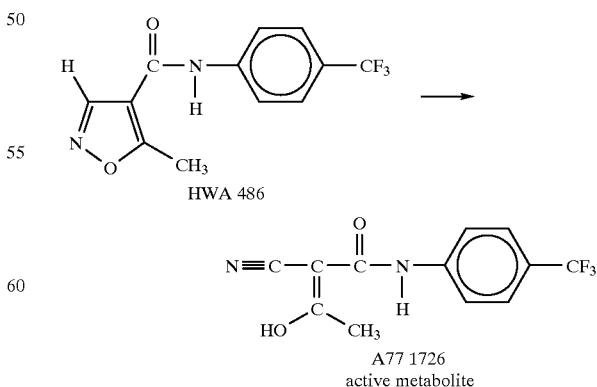

Studies on the molecular mechanism of action of this active compound point to an influence on the pyrimidine metabolism. Because leflunomide is very rapidly converted in the body into A77 1726, in this specification, leflunomide and A77 1726 are used interchangeably. Thus, both "leflunomide resistance" and "A77 1726 resistance" are used to designate the same condition.

Pyrimidine and purine nucleotides play a key part in biological processes. As structural units of DNA and RNA, they are thus carriers of genetic information. The biosynthesis of the pyrimidines comprises the oxidation of dihydroorotate to orotate, which is catalyzed by the enzyme dihydroorotate dehydrogenase (DHODH). Altogether, six enzymes are needed for the de novo synthesis of uridine monophosphate (UMP). UMP plays a key part in the synthesis of the other pyrimidines, cytidine and thymidine. The inhibition of DHODH thus leads to an inhibition of pyrimidine de novo synthesis. Particularly affected are immune cells, which have a very high need for nucleotides, but can only cover a little of this by side routes (salvage pathway). Binding studies with radiolabeled leflunomide analogs identified the enzyme DHODH as a possible site of action of A77 1726 and thus the inhibition of DHODH by leflunomide is an important starting point for the elucidation of the observed immunomodulating activities. Williamson, et al. *J. Biol. Chem.* 270:22467–22472 (1995).

SUMMARY OF THE INVENTION

In one embodiment, the invention provides an isolated DNA sequence encoding a DEAH-box leflunomide-resistant protein. The invention also provides such a DNA sequence wherein said protein has a molecular weight of 135 kilodaltons. The invention also provides such a DNA sequence, wherein said protein has a molecular weight of about 135 kilodaltons.

In another embodiment, the invention provides an isolated DNA sequence as set forth in SEQUENCE ID NO. 15 (FIG. 8) and an isolated DNA sequence as set forth in SEQUENCE ID NO. 17 (FIG. 9). In other embodiments, the invention provides a homolog of the DNA sequence of SEQ. ID. NO. 15 and a homolog of the DNA sequence of SEQ. ID NO. 17.

In another embodiment, the invention provides isolated DNA sequences encoding the amino acid sequence of SEQUENCE ID NO. 16 (FIG. 8) and encoding the amino acid sequence of SEQUENCE ID NO. 18 (FIG. 9).

In yet another embodiment, the invention provides an isolated DNA sequence that encodes a DEAH-box protein having one or more of the following characteristics:

(a) the first homology domain (ATPase A, Domain I) is located more than 650 amino acids from the N-terminus of said protein; (b) the N-terminus of said protein contains serine/arginine domains; (c) domain IV of said protein has the sequence FMP; (d) the distance between domains IV and V of said protein is 74 amino acids or less; and (e) domain VI of said protein has the sequence QRSGRXGR (SEQ ID NO:25).

The invention also provides an expression vector comprising a DNA sequence according to the invention. The invention further provides a host comprising such an expression vector. The invention also provides an antisense expression vector comprising a DNA according to the invention, wherein said DNA sequence is inserted in reverse orientation into said vector.

In another embodiment, the invention provides an isolated leflunomide-resistant DEAH-box protein. The invention also provides such a protein wherein said protein has a molecular weight of 135 kilodaltons. The invention further provides such a protein wherein said protein has a molecular weight of about 135 kilodaltons. The invention also provides a mammalian protein, a protein isolated from a cell line derived from the murine cell line A20.2J and a human protein.

In yet other embodiments of the invention there is provided a protein comprising the amino acid sequence of SEQUENCE ID NO. 16 (FIG. 8), or a fragment thereof, or the amino acid sequence of SEQUENCE ID NO. 18 (FIG. 9), or a fragment thereof.

In yet another embodiment, the invention provides an isolated DEAH-box protein having one or more of the following characteristics: (a) the first homology domain (ATPase A, Domain I) is located more than 650 amino acids from the N-terminus of said protein; (b) the N-terminus of said protein contains serine/arginine domains; (c) domain IV of said protein has the sequence FMP; (d) the distance between domains IV and V of said protein is 74 amino acids or less; and (e) domain VI of said protein has the sequence QRSGRXGR (SEQ ID NO:25).

In another embodiment, the invention provides a process for the preparation of a DEAH-box leflunomide-resistant protein, wherein said process comprises:

(a) culturing a host cell comprising a vector encoding a DEAH-box leflunomide-resistant protein and
(b) isolating said protein from the cell of step (a).

In yet another embodiment, the invention provides an "identifying" method for identifying a substance having one or more of the following properties: anticarcinogenic, antiatherosclerotic, immunosuppressive, antiinflammatory, antiviral, antifungal or antibacterial, comprising:

(a) crystallizing a protein according to the invention;
(b) determining the three-dimensional structure said protein; and
(c) identifying said substance using molecular modeling techniques, wherein said substance affects the ability of said protein to bind ATP or nucleic acid.

The invention further provides such an identifying method wherein the method comprises the additional step of determining the ability of the identified substance to modulate the helicase activity of said DEAH-box leflunomide-resistant protein. The invention also provides such an identifying method comprising the additional step of determining the ability of the identified substance to modulate the ATPase activity of said protein. Finally the invention provides such an identifying method comprising the additional step of determining the ability of the identified substance to modulate the splicing activity of said protein. In another embodiment, the invention provides a substance identified using any of the foregoing methods.

In yet another embodiment, the invention provides a therapeutic method for the treatment of a disorder selected from the group consisting of Alzheimer's disease, cancer, rheumatism, arthrosis, atherosclerosis, osteoporosis, acute and chronic infectious diseases, autoimmune disorders, diabetes or organ transplant rejection, comprising administration of a pharmaceutically effective amount of a substance identified using the above-mentioned method to a patient in need of such treatment.

The invention further provides an "identifying" method for identifying a substance that will modulate the helicase activity of a protein according to the invention, comprising the additional steps of: (a) transforming a non-leflunomide-resistant cell with a DNA sequence encoding a DEAH-box protein which binds nucleic acid and ATP, and which has helicase activity and ATPase activity, wherein the level of expression of said protein is significantly higher in a leflunomide-resistant cell than in a non-leflunomide-resistant cell, wherein said transformed cell is rendered resistant to leflunomide;

(b) culturing the cells in the presence of a high level of leflunomide;

(c) determining the ability of said substance to make the cells of step (b) non-leflunomide-resistant, wherein a substance that makes said cells non-leflunomide-resistant modulates the helicase activity of said protein.

In another embodiment, the invention provides a method for isolation of RNA that binds specifically to a protein according to the invention, comprising:

(a) binding said protein or a fragment thereof to an affinity matrix;

(b) mixing an RNA sample to the matrix of step (a); and (c) determining which RNA is specifically bound to said matrix. The invention also provides such a method comprising the additional step of amplifying the RNA bound to said matrix by using the PCR technique. The invention also provides such a method, wherein said RNA of step (c) is subjected to sequence analysis.

Finally, in another embodiment, the invention provides a method for selecting a cell that contain heterologous DNA comprising:

(a) transforming cells with a vector comprising a DNA sequence encoding a DEAH-box leflunomide-resistant protein;

(b) growing said cells in the presence of a high level of leflunomide; and (c) selecting a cell that will grow in the presence of said high level of leflunomide; wherein said cell of step (c) contains said heterologous DNA.

BRIEF DESCRIPTION OF THE DRAWINGS

FIG. 6(A): Results of the initial sequencing and restriction mapping of the isolated positive clones. Clones 1 and 3 are nearly identical. Clones 1/3 to 4 overlap and have the hs1/hs2 sequence in the insert. Clones 1/3 and 2 have a common Sph I cutting site. cDNA 4 lies completely in cDNA 2. Clone 5 differs from the other clones by the size (6.5 kb), the restriction cutting sites and the missing hs1/hs2 cDNA.

FIG. 6(B): Homology domains in the sequence of the cDNA. The homology domains are framed and the distance in amino acids between the domains is indicated. Nine DEAH box homology domains are shown. The domain NLS has homology to the "nuclear localization site" from the T antigen (SEQ ID NO:2 is shown in this figure.)

FIG. 7: (A) Primer construction (SEQ ID NOS 7–14, respectively) of a subregion of the 135 kDa protein from A20R, which is expressed to an increased extent. The series of letters in each case characterize the amino acids in the single letter code (SEQ ID NOS 28–33, respectively; under this the nucleotide sequence is indicated. The amino acid sequences written in brackets are listed beginning with their C-terminal end and are derived from DNA sequences which are complementary to the primer sequences given here. In each case the degenerate genetic code is given. As the third base of the codon is often not clear, in order in each case to obtain the appropriate base for the corresponding amino acid, a mixture of all possible bases is synthesized. N is the abbreviation for all four bases (G, A, T, C). I is the abbreviation for inosine, which enters into base pairing with purine and pyrimidine bases. R=A, G; Y=T, C; S=G, C. A20-2, A20-3, A20-4 and A20-5 are degenerate primers situated upstream. A20-6a and A20-6b are primers situated downstream. The average distance of the primers situated upstream and downstream to one another is approximately 600 nucleotides. In the case of the primer A-20-6b indicated under 6, the 16th nucleotide was inadvertently set equal to N, so that here in the corresponding complementary strand the coding is both for isoleucine (ATT, ATC, ATA) and for methionine (ATG). This fact did not affect the success of the PCR carried out, but in this way a methionine appears falsely as the sixth-last amino acid in the sequence as in FIG. 8 and not the correct isoleucine. (B) Primer derived from the human cDNA clone B 185; 7=downstream primer; 8=upstream primer.

FIGS. 8a and 8b: Sequencing of the subregion of the 135 kD DEAH-box protein from leflunomide-resistant A20R cells. Below the base sequence (SEQ ID NO:15) (1-612) the corresponding amino acid sequence (SEQ ID NO:16) is given in the single letter code. Isoleucine and not methionine is correct as the sixth to last amino acid; for explanation see legend to the figure for FIG. 7. The DNA fragment shown was used as an A20-5/-6b probe for the hybridization experiments.

FIG. 9a–9i: Sequence of the coding region of the entire human cDNA (4272 bp total length). From the position of the homologies to the mouse sequence, it followed that the first reading frame was correct. The coding sequences lie between positions 148 and 3831 (SEQ ID NO:17) and yield a sequence of 1227 amino acids (SEQ ID NO:18). (*=stop)

FIG. 10: Similarities of the gene for the human 135 kD DEAH-box protein with other DEAH-box proteins.

DETAILED DESCRIPTION OF THE INVENTION

Figure 1:
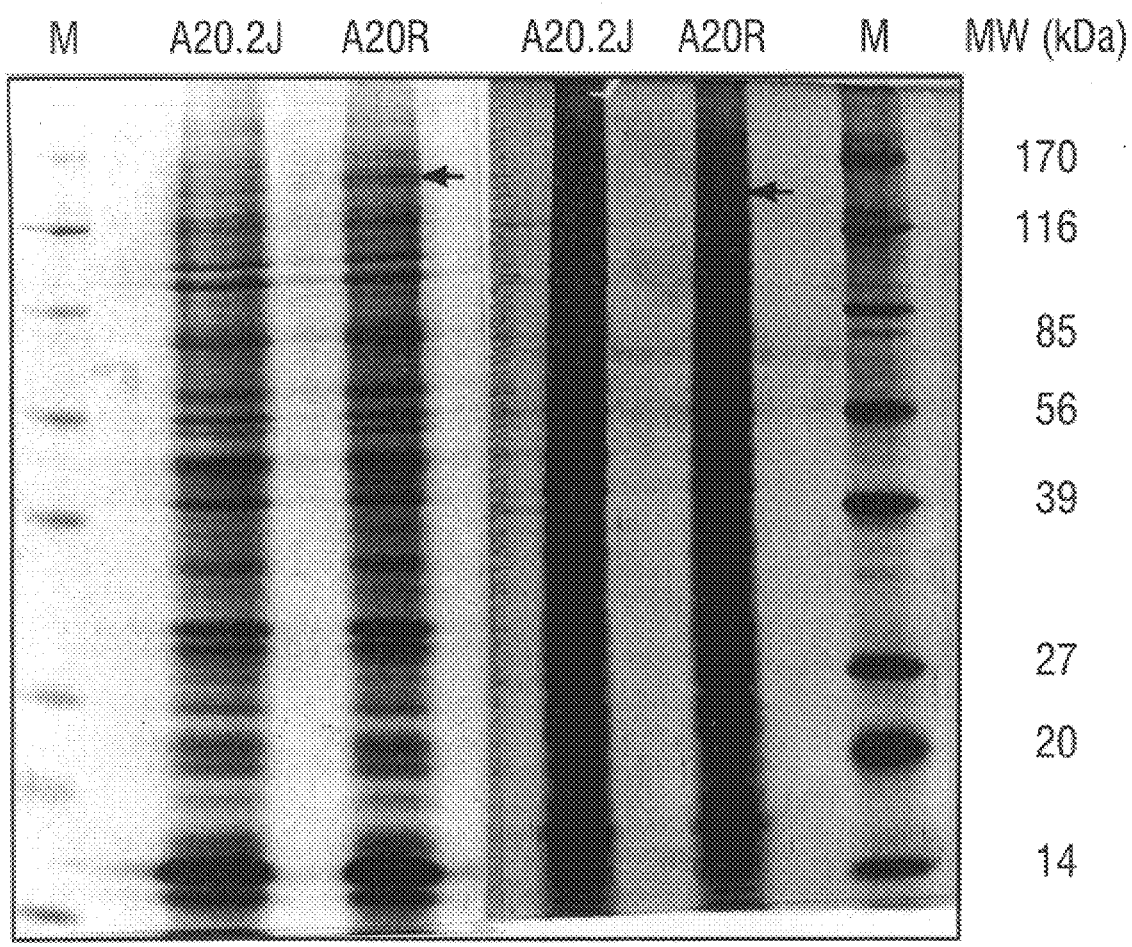
FIG. 1: SDS-PAGE (12% acrylamide). The left three gel traces are from a Coomassie Blue-stained gel, the three right gel traces from a silver-stained gel. M: Marker (Combithek from Boehringer Mannheim); A20.2J: normal A20 cells; A20R: A20 cells which are resistant to 100 μM leflunomide. In the Coomassie Blue-stained gel, 100 μg of protein in each case were applied per gel pocket, in the silver-stained gel 5 μg of protein in each case. The arrow marks the protein which is expressed to an increased extent in resistant A20 cells.

The present invention relates to the identification and molecular-biological and biochemical characterization of novel proteins which show structural similarity with other known helicases. It is demonstrated that such proteins bind ATP and nucleic acid and possess helicase and ATPase activities. This invention further relates to processes for preparation of such proteins and their use in pharmacologically relevant test systems and therapeutic applications.

In order to identify potential intracellular sites of action of leflunomide, a leflunomide-resistant cell line was developed (see also Example 1). This resistance was induced against A77 1726 in the highly proliferative cell line A20.2J (murine B-cell lymphoma). The concentration of A77 1726 was increased stepwise in a serum-free culture system, which finally led to the establishment of a stable subline named A20R. The A20R cell line tolerates 30-40 times higher leflunomide concentrations than the original cell line A20.2J ($ED_{50}$ 130 $\mu$M compared with 4 $\mu$M).

Surprisingly, it has now been found that by means of such a treatment of a leucocyte cell line with rising, but nontoxic, doses of the antiproliferative active compound leflunomide, the expression of a hitherto unknown 135 kD DEAH-box protein is induced. This protein is a "DEAH-box leflunomide-resistant protein" (defined below). The helicase and ATPase activities of this protein are assessed using techniques that are well known to the skilled artisan. The ability of this protein to bind RNA or otherwise affect RNA homeostasis is also assessed using methods well known to the skilled artisan. Stimulation of RNA helicase activity in leflunomide-resistant cells would enable the cells to proliferate, probably by means of more efficient utilization of existing transcripts.

As used in this specification a "DEAH-box leflunomide-resistant protein" is used to mean a protein that has the ability to bind nucleic acid and ATP, and has ATPase and helicase activities, wherein the level of expression of said protein is significantly higher in a leflunomide-resistant cell than in a non-leflunomide-resistant cell, with the proviso that such a "DEAH-box leflunomide-resistant protein" is not a protein that was publicly known prior to Dec. 4, 1995.

As used in this specification, "publicly known" means known or used by others in the United States, or patented or described in a printed publication in the United States or a foreign country, or in public use, or on sale.

As stated above, a DEAH-box leflunomide-resistant cells is expressed at a significantly higher level in a cell that tolerates high levels of leflunomide (leflunomide-resistant cell), when compared with the protein expression level in a corresponding cell line that does not tolerate high levels of leflunomide. For example, the $ED_{50}$ for leflunomide in murine A20.2J cells is 4$\mu$, whereas the $ED_{50}$ for murine A20.2J cells that are resistant to high levels of leflunomide is 130$\mu$. (See Example 1 below.) As used in this specification, a "leflunomide resistant" cell is one that will tolerate a high level of leflunomide. Conversely, "non-leflunomide-resistant cells" will not tolerate these high levels of leflunomide. Tolerance to leflunomide is indicated by the ability to proliferate in the presence of high levels of leflunomide. As used in this specification, a "high level of leflunomide" is used to mean concentrations in the range of about 100 $\mu$M to about 150 $\mu$M. As used in this specification, a first cell that expresses a "significantly higher level" of a particular protein than a second cell expresses about 20 times to about 100 times as much of the particular protein as the second cell, as expressed per milligram of total cell protein.

The invention also includes a protein comprising the amino acid sequence shown in FIG. 8 (SEQUENCE ID NO. 16) and the amino acid sequence shown in FIG. 9 (SEQUENCE ID NO. 18). Other embodiments of the invention include a "fragment" of an amino acid sequence as set forth in FIG. 8 (SEQ. ID NO. 1 6) and a "fragment" of an amino acid sequence as set forth in FIG. 9 (SEQ. ID NO. 18). As used in this specification, a "fragment" of the FIG. 8 or FIG. 9 sequence is all or part of the FIG. 8 or FIG. 9 sequence, with the proviso that such a fragment is not a fragment that was publicly known prior to Dec. 4, 1995.

The invention also encompasses DEAH proteins with the ability to bind nucleic acid and with helicase and ATPase activities that have been isolated from mammalian cell lines, including a human cell line or a derivative of the murine cell line A20.2J.

In another embodiment, the invention provides a protein that has a molecular weight of 135 Kd and that retains the "essential identifying characteristics" of a protein according to the invention—having the ability to bind nucleic acid and ATP, and having ATPase and helicase activities. In yet another embodiment, the invention provides such a protein having a molecular weight of about 135 Kd. The skilled artisan will recognize that proteins having other molecular weights are also encompassed by the invention.

In yet another embodiment, the invention relates to an isolated DEAH-box protein having or more of the following characteristics: (1) the first homology domain (ATPase A, Domain I) is located more than 650 amino acids from the N-terminus; (2) there are Serine/Arginine (SR) domains in the N-terminus (3) domain IV has the sequence FMP; (4) the distance between domains IV and V is 74 amino acids or less; (5) domain VI has the sequence QRSGRXGR (SEQ ID NO:25). Homology domains are shown in FIG. 6B.

The present invention also relates to preparing in a manner which is conventional and known from the literature monoclonal and polyclonal antibodies against the entire protein, parts of the protein and peptide sequences obtained by proteolytic degradation or peptide synthesis. See, for example, Coligan, et al. (eds.) CURRENT PROTOCOLS IN IMMUNOLOGY, pp. 2.0.3-2.11.8 (John Wiley & Sons, 1992). The present invention also relates to purification processes for the functional protein. The invention further relates to the structural and functional characterization of the protein according to the invention. Such characterization may be carried out using both molecular biological and biochemical techniques that are well known to the skilled artisan.

The present invention also relates to methods for identifying, isolating and cloning a gene or gene subsequences encoding such proteins according to methods which are conventional and known from the literature. The invention also relates to methods for expressing such genes or gene subsequences in suitable expression systems.

A further embodiment of the invention is an isolated DNA sequence which encodes a protein according to the invention. The invention includes the DNA sequence shown in FIG. 8 (SEQUENCE ID NO. 15) and the DNA sequence shown in FIG. 9 (SEQUENCE ID NO. 17).

A further embodiment of the invention is a "homolog" of the DNA sequence in FIG. 8 (SEQ. ID NO. 15) and a homolog of the DNA sequence shown in FIG. 9 (SEQUENCE ID NO. 17). As used in this specification, a "homolog" of the sequence of FIG. 8 (SEQ. ID NO. 15) is a nucleotide sequence which under stringent conditions, hybridizes to the DNA sequence as in FIG. 8 or to a subsequence of the sequence in FIG. 8 (SEQ. ID NO. 17), with the proviso that said sequence is not a DNA sequence encoding a member of the DEAD-box protein family that was publicly known prior to Dec. 4, 1995. Similarly, a "homolog" of the sequence of FIG. 9 is a DNA sequence that hybridizes under stringent conditions to the DNA sequence as in FIG. 9 or to a subsequence of the sequence in FIG. 9, with the proviso that said sequence is not a DNA sequence encoding a member of the DEAD-box protein family that was publicly known prior to Dec. 4, 1995.

Stringency, as used in this specification, means the condition with regard to temperature, ionic strength and the presence of certain organic solvents, under which nucleic acid hybridizations are carried out. As used in this specification, "stringent conditions" for hybridization is used to designate the following types of stringent washes: (1) 68° C., or about 68° C. using ExpressHyb solution (Clontech, Heidelberg, Germany)(radioactive label): (2) 40–600° C. in DigEasyHyb solution (Boehringer Manheim) (nonradioactive label). In alternative embodiments, "stringent conditions" means hybridization at about 43° C. in DigEasyHyb solution for identification of DNA/DNA hybrids or hybridization at about 50° C. in DigEasyHyb solution for identification of DNA/RNA (including mRNA) hybrids. In another alternative embodiment, "stringent conditions" includes hybridization in 0.1×SSC and 0.1% SDS at 40–60° C. The skilled artisan will recognize that the precise stringent hybridization parameters may be optimized, depending on experimental conditions.

Thus, in another embodiment, the present invention relates to DNA sequences that will hybridize to the DNA sequence of FIG. 8, FIG. 9, or a subsequence of either sequence under the following stringent conditions: ExpressHyb solution (Clontech, Heidelberg, Germany) at 68° C. or at about 68° C. Further washing techniques are set forth in Example 6.

A further embodiment of the invention is a DNA which, on account of the degeneracy of the genetic code, is different from the DNA sequences of the invention (as illustrated in FIGS. 8 and 9), but which expresses a DEAH box protein that binds nucleic acid and ATP, and which has helicase and ATPase activities. The skilled artisan will recognize that conservative nucleotide changes may be made that will encode the same amino acid sequence of the 135 kD DEAH-box proteins described herein. In addition, the skilled artisan will also recognize that the nucleotide changes in a DNA sequence according to the invention can be made to effect conservative amino acid substitutions. These changes may be made so that such proteins made will retain the "essential identifying characteristics" of a protein according to the invention—having the ability to bind nucleic acid and ATP, and having ATPase and helicase activities.

One of skill in the art will recognize that such DNA sequences may be made using many techniques that are well-known in the art, such as synthetic oligonucleotide synthesis, site-directed mutagenesis. In addition, DNA sequences according to the invention can be identified by using all or part of a nucleotide sequence disclosed in this specification as a probe to screen genomic or cDNA libraries. Such techniques are well-known to the skilled artisan. For example, a suitable subregion of the human gene is nucleotide 1594 to nucleotide 2205. In addition, the entire sequence of a human or murine DEAH-box protein according to the invention can also be used as a probe.

The invention includes a DNA sequence that encodes a protein that has the ability to bind nucleic acid and ATP, and has ATPase and helicase activities, wherein the level of expression of said protein is significantly higher in a leflunomide-resistant cell than in a non-leflunomide-resistant cell.

In another embodiment, the invention provides a DNA sequence that encodes a protein that has a molecular weight of 135 kD and that retains the "essential identifying characteristics" of a protein according to the invention—having the ability to bind nucleic acid and ATP, and having ATPase and helicase activities. In yet another embodiment, the invention provides such a protein having a molecular weight of about 135 kD. The skilled artisan will recognize that proteins having other molecular weights are also encompassed by the invention.

In yet another embodiment, the invention relates to a DNA sequence that encodes a protein having or more of the following characteristics: (1) the first homology domain (ATPase A, Domain I) is located more than 650 amino acids from the N-terminus; (2) there are Serine/Arginine (SR) domains in the N-terminus (3) domain IV has the sequence FMP; (4) the distance between domains IV and V is 74 amino acids or less; (5) domain VI has the sequence QRS-GRXGR (SEQ ID NO:25). Homology domains are shown in FIG. 6B.

In addition, the invention relates to a vector which comprises a DNA sequence encoding a protein according to the invention and which is suitable for the expression of said protein in a suitable host cell. An expression vector for a suitable host cell is a vector which in the appropriate host cell is capable of heterologous gene expression and of replication, constitutively or after induction by means of customary methods. Suitable vectors include, but are not limited to, PSEAP, PCMV, pSV, pTK, pcDNAI (Clontech, Heidelberg, Germany). In one embodiment, those vectors that carry out gene expression and replication with high efficiency are used.

Another embodiment of the invention is such a host cell containing a vector according to the invention. Suitable host cells include, but are not limited to, Jurkat T-cells, Raji B-cells, A20 cells, Hela cells, insect cells for Bacculo virus expression systems.

In addition, the invention relates to an "antisense" expression vector. Such an expression vector contains a DNA sequence according to the invention, which is inserted in reverse orientation in the expression vector. Thus, the skilled artisan will recognize that the mRNA corresponding to the DNA in the antisense vector will hybridize with an mRNA corresponding to the DNA in the "sense" orientation vector. An antisense expression vector is a vector which expresses a desired antisense RNA in an appropriate host cell, either constitutively or after induction by means of customary methods.

In another embodiment, the invention provides processes for the preparation of the a protein according to the invention by expression of the protein by means of the vectors and host cells mentioned and subsequent isolation of the protein using customary methods that are well known to the skilled artisan. For example, affinity purification, HPLC, and FPLC can be used.

By making available this protein and related RNA helicases, novel anticarcinogenic, anti-atherosclerotic, immunosuppressive, antiinflammatory, antiviral, antifungal and antibacterial active substances are identified. These are urgently needed for the efficient therapy of a whole host of diseases, such as, for example, Alzheimer's disease, cancer, rheumatism, arthrosis, atherosclerosis, osteoporosis, acute and chronic infectious diseases, autoimmune disorders, diabetes and organ transplant rejection. The skilled artisan will recognize that preparation of pharmaceutical preparations of such substances are well known in the art.

Thus, the invention furthermore relates to the use of a protein according to the invention in a test or assay system for finding novel or identifying already known substances which have anticarcinogenic, anti-atherosclerotic, immunosuppressive, antiinflammatory, antiviral, antifungal or antibacterial action. In one embodiment, a protein according to the invention is prepared using genetic engineering, or recombinant DNA, methods. Such an assay system can be designed such that a protein according to the invention is crystallized and its three-dimensional structure is elucidated using customary methods. See, for example, A. McPherson, PREPARATION AND ANALYSIS OF PROTEIN CRYSTALS (John Wiley & Sons, 1982) and Ducruix, et al., eds. CRYSTALLIZATION OF NUCLEIC ACIDS AND PROTEINS (Oxford University Press, Oxford, 1992).

Using customary methods of "molecular modeling," substances are identified or developed which react with a protein according to the invention. Thus, a substance is identified that affects the ability of such a protein to bind ATP or other substrates, such as DNA, RNA and RNA/protein complexes. Substances which interfere with the protein substrate binding site(s) or at a site which affects such functional epitopes are identified. Molecular modeling techniques are known in the art. See, for example, Fruehbeis, et al., *Int. Ed. Engl.* 26:403 (1987); Perun, etal., eds. COMPUTER-AIDED DRUG DESIGN (Marcel Dekker, Inc.: New York, 1989)); van de Waterbeemd, ADVANCED COMPUTER-ASSISTED TECHNIQUES IN DRUG DISCOVERY (Verlagsgesellschaft, Weinheim, 1994); and Blundell, *Nature*, 384:23 (1996), all of which are hereby incorporated by reference.

Substances are also tested for their ability to modulate the enzymatic activities of a protein according to the invention. As used in this specification, a substance that "modulates" an enzyme activity causes a change in the enzyme activity when compared to the enzyme activity as measured in the absence of the test substance. For example, a substance may partially or totally inhibit the enzyme activity. The test for RNA helicase activity is carried out by methods known to the person skilled in the art. For example, synthetic oligoribonucleotides can be immobilized on a matrix and hybridized with complementary, labeled oligoribonucleotides. The hybridized oligos are then contacted with a protein according to the invention, which releases a certain, measurable amount of the labeled, non-matrix-immobilized oligoribonucleotides, due to the helicase activity of the protein. The effect of the presence or absence of potential modulators on the helicase is tested. Alternatively, the procedure described by Jaramillo, et al. *Mol. Cell. Biol.* 11:5992 (1991). Briefly, duplex RNA substrate (labeled with $^{32}$p) is mixed with helicase protein in a buffered solution and the reaction is terminated using glycerol/SDS/EDTA/bromphenol blue. This reaction mixture is applied to an SDS gel (8%) and the gel is run using standard procedures. Unwinding efficiency is defined as the ratio of unwound monomer RNA relative to duplex RNA. Other assay procedures are well known in the art. See, for example, Rozen, et al. *Mol. Cell. Biol.* 10:1134 (1990) and Pause, et al. *EBMO J.* 11:2643 (1992), which are hereby incorporated by reference. Such assays can also be carried out on microtiter plates, by which means a large number of modulators can be tested for their action with high efficiency.

Further assays for modulators of a protein according to the invention is ATPase or splicing tests in which the effect of modulators is tested on the ATPase or splicing properties of a protein according to the invention.

The test for ATPase activity is carried out using procedures that are well known in the art. For example, the procedure described by Pause, et al. *EBMO J.* 11:2643 (1992) is used. Briefly, a protein according to the invention is incubated at 37° C. in a buffered solution containing $^{32}$P-labeled ATP. The reaction is stopped by the consecutive addition of the following reagents at 4° C.: 20 mM silicotungstate, 1 mM potassium phosphate, 5% ammonium molybdate/4M sulphuric acid, 2.5% trichloroacetic acid/50% acetone, 50% isobutyl alcohol/50% benzene. The mixture is vortexed and centrifuged. The upper phase is assayed for radioactivity to determine ATP hydrolysis.

A protein according to the invention is also tested for its RNA splicing activity. A splicing assay is carried out using procedures that are well known in the art. For example, the procedure of Tarn, et al., *Cell* 84:801 (1996) or the procedure of Xu, et al. *Nature*, 381:709 (1996), which are hereby incorporated by reference, may be used.

In another embodiment of the invention, modulators of a protein according to the invention are identified using the following procedure. Cells that are not resistant to high levels of leflunomide are transformed with a vector containing a gene encoding a protein according to the invention. These transformed cells are grown in the presence of leflunomide. These cells tolerate leflunomide because they express a protein according to the invention. Various compounds are tested for their ability to inhibit the growth of the transformed cells. Those compounds that cause the cells to die or decrease cell proliferation are likely inhibiting the activity of the protein according to the invention. Thus, such substances are further characterized for their ability to modulate the activities of a protein according to the invention—ability to bind ATP and nucleic acid and having helicase and ATPase activities.

Accordingly, other embodiments of the invention include therapeutic methods for treatment of various disorders comprising administering a therapeutically effective amount of a substance (identified using the above-described methods) to a patient in need of such treatment.

In another embodiment of the invention, a protein according to the invention is used to isolate RNAs binding specifically to such a protein. The oligoribonucleotide sequence (s) of RNAs binding to a protein according to the invention can then be determined. To isolate such RNAs, a protein according to the invention (or a fragment thereof) is coupled to a matrix. The affinity matrix prepared in this way is used to concentrate RNAs, which specifically bind to the coupled protein or parts thereof, from RNA mixtures. Binding can be measured by standard methods like Electrophoretic Mobility Shift Assay (EMSA) or ELISA, which are well known in the art. The following assays may also be used: Scintillation Proximity Assay (SPA, Amersham International, Little Chalfont, Buckinghamshire, England) and BIAcore (Biomolecule Interaction Analysis, Pharmacia, Upsala Sweden).

The RNA fragments obtained from the affinity matrix are then amplified using various PCR primers (or linkers) and the amplified fragments are then sequenced using techniques well known to the skilled artisan. PCR primers are selected using an oligo dT primer (3' end) in combination with a degenerate primer (5' end). Alternatively, the Rapid Amplification of cDNA Ends protocol can be used. See Innis, et al., eds. PCR PROTOCOLS: A GUIDE TO METHODS AND APPLICATIONS. Academic Press: San Diego, 1990.

Yet another embodiment of the invention is the use of a DNA sequence according to the invention as a selection marker. Such a DNA sequence can be used as a marker when it is inserted into a vector. In this embodiment of the invention, use is made of the observation that in a Southern blot analysis of genomic DNA of the A20R cells in comparison with genomic DNA of the A20.2J cells the mRNA corresponding to the gene which encodes a 135 kD DEAH-box protein is increased, or amplified. Thus, a vector comprising a DNA sequence according to the invention can be inserted into cells that are not naturally resistant to leflunomide. Cells containing the foreign, or heterologous, DNA containing the gene encoding a protein according to the invention will grow in the presence of leflunomide, and hence be selected. In yet another embodiment of the invention, cells can be transformed with a vector comprising a gene encoding a protein that is amplified in cells that are resistant to leflunomide analogs.

The gene amplification by leflunomide or leflunomide analogs observed as exemplified by this gene is used in the selection of cells and in gene therapy. In some gene therapy applications, it may be advantageous to treat a patient with a vector encoding a protein that will substitute for a defective protein that is produced by the patient in need of gene therapy. As noted above, a variety of diseases are associated with overexpression of helicase activity. Thus, overexpression of a protein according to the invention is determined. The protein and mRNA levels for such a protein are compared in normal individuals and those individuals with a disease, such as a hereditary disease, an autoimmune disease, or cancer. In those diseases having amplified expression of a protein according to the invention, such amplification is used as a marker for the presence of disease. In some instances, the amplification is used as a marker for those individuals at risk for developing a particular disease.

The invention will now be illustrated in greater detail with the aid of the figures and examples, without being restricted thereto.

EXAMPLE 1

Preparation of the Leflunomide-Resistant Cells
Medium:
The culturing of the starting line, the breeding of the resistant subline A20R and the proliferation tests for checking the cross-resistance of the A20R cells were performed in a self-prepared, serum-free medium. Dry medium for 10 liters of Iscove medium (Biochrom, Berlin) was dissolved in 10 liters of double-distilled water.

18.95 9 of NaCl
11.43 g of $NaHCO_3$
700 mg of KCl
10 ml of 35% strength NaOH solution
0.5 ml of 1 molar mercaptoethanol solution were then added to the solution and the medium was sterile-filtered (all substances from Riedel de Häen).
Before use
32 mg of human holo-transferrin
1 g of bovine albumin
1.5 ml of lipids
(all substances from Sigma) were added to 1 liter of Iscove medium.

Description of the starting line A20.2J:
A20.2J is a subline of the mouse B-cell lymphoma A20 (ATCC TIB-208) and described as a fusion line in the ATCC for the cell line LS 102.9 (ATCC HB-97). The cells were distinguished by high proliferation (doubling time about 10 hours) and a high sensitivity (50% inhibition of the proliferation of the cells at 2 $\mu$M substance) to A77 1726 (the main metabolite of leflunomide). The cells were easy to culture as a nonadherent-growing cell line.

Description of resistance breeding:
A20.2J cells were initially cultured for 5 days in Iscove medium with 1 $\mu$M A77 1726 (concentration below the 50% inhibition of proliferation) and the cell growth and the vitality of the cells were checked. Every 2nd or 3rd day, the cells were passaged in fresh medium to which the same concentration of A77 1726 was added. After culturing for 5 days, growth of the cells and a low dying-off rate (maximum 30% dead cells) was detectable, so the concentration of A77 1726 was increased stepwise. If the proliferation of the cells stagnated, the concentration of the last passage was used. After culturing for one year, a stable, resistant subline A20R was established which, in the presence of 100 $\mu$M A77 1726, showed constant proliferation and no differences morphologically to the starting line A20.2J.

Detection of proliferation:
$5 \times 10^5$ cells were incubated in 5 ml of Iscove medium in 6-well plates (Greiner) for 48 hours at 37° C. and 10% $CO_2$. One well was set up as a positive reference value:
for A20.2J:cells in Iscove medium
for A20R:cells in Iscove medium+100 $\mu$M A77 1726
Test substances in various concentrations were pipetted into the cells in the remaining wells. After the incubation time, the cells were resuspended in the well, and 100 $\mu$l of cell suspension were taken and diluted in 1% strength Eosin solution (1 g of Eosin yellowish from Riedel de Häen dissolved in 100 ml of sterile isotonic saline solution). The cells were counted in a Neubauer counting chamber and the fraction of dead cells (stained by Eosin) determined. The substance-induced alteration of proliferation was calculated relative to the respective positive control.

Test 2:
$4 \times 10^3$ cells were pipetted into a volume of 100 $\mu$l of Iscove medium in 96-well round-bottom microtiter plates (Nunc). Test substances were applied in twice the concentration starting from the desired test concentration and 100 µl of this solution was pipetted into the cells. The plates were incubated for 48 hours at 37° C. and 10% $CO_2$. The proliferation was determined by radiolabeling the DNA of dividing cells. To do this, after the incubation time 25 µl of $^3$H-thymidine (10 µCi/ml; specific activity 29 Ci/mmol; Amersham) was added to each well and the mixture was incubated for a further 16 hours. To evaluate the test, the plates were harvested on glass fiber filters (Pharmacia) by means of a cell harvester (Skatron), unincorporated $^3$H-thymidine being collected in separate waste flasks, and only cellular, DNA-bound radioactivity being measured. The filters were heat-sealed in plastic bags and after addition of 10 ml of scintillator (Pharmacia) sealed in counting cassettes for measurement. Measurement was carried out in a beta-counter (beta-plate system 1206 from Wallac). As indicated under Test 1, the alteration in proliferation of the test substances was calculated against the respective positive controls.

EXAMPLE 2

Test for the Resistance of the A20R Cells

1. Cross-resistance to antiproliferative substances known from the literature:

Antiproliferative substances known from the literature were tested at different concentrations (as described in proliferation test 2) for their antiproliferative properties on A20R cells and A20.2J. In the following table, the calculated inhibition of a concentration of these substances on both cells lines is shown. The resistance of the A20R cells to antiproliferative substances is compared with the starting line A20.2J.

| Test substances | | % inhibition of A20.2J | % inhibition of A20R |
|---|---|---|---|
| Methotrexate | (0.15 µM) | 75.9 | 65.2 |
| Cisplatin | (10 µM) | 44.7 | 91.1 |
| Cyclosporin A | (0.25 µM) | 69.9 | 77.5 |
| Mycophenolic acid | (0.15 µM) | 89.8 | 76.8 |

2. Cross-resistance to structurally related substances similar to A77 1726.

As no general resistance of the A20R cells to antiproliferative substances was present (Example 2(1)), it was determined whether structurally related analogs of A77 1726 have the same proliferation-inhibiting properties on A20R cells as on A20.2J cells. The investigation was carried out by means of proliferation test 1. In the table which follows, comparative $IC_{50}$ values (the concentration of a substance which inhibits the proliferation of the cells by 50%) are shown.

| Test substances | $IC_{50}$ value of A20.2J | $IC_{50}$ value of A20R |
|---|---|---|
| A77 1726 | 2–3 µM | 130 µM |
| X92 0715 | 8 µM | 120 µM |
| X91 0279 | 10 µM | 120 µM |
| X91 0325 | 10 µM | 75 µM |

A20R cells show a gradually decreasing cross-resistance to structurally related A77 1726B analogs, which suggests a structure-specific resistance.

3. Cross-resistance of the A20R cells to brequinar:

Earlier investigations on the mechanism of action of leflunomide pointed to parallels with brequinar (Dupont-Merck). For this reason, brequinar was additionally included in the investigations on the cross-resistance of A20R. Brequinar is not a structural analog of leflunomide.

The $IC_{50}$ values of the A20.2J and A20R cells to the brequinar sodium salt were determined with the aid of proliferation test 1.

| | $IC_{50}$ value of A20.2J | $IC_{50}$ value of A20R |
|---|---|---|
| Brequinar Na$^+$ salt | 0.2 µM | 50–75 µM |

A20R cells show with respect to their growth behavior a cross-resistance to analogs of A77 1726 and brequinar, a substance which inhibits DHODH.

EXAMPLE 3

Investigation of A20R Cells for MDR Proteins

Gel electrophoresic separations of the cellular proteins of the A20.2J and A20R cells showed that a protein having a molecular weight of above 135 kDa (determined using protein calibration markers) was overexpressed in the resistant line (see also FIG. 1). This example evaluates whether the 135 kDa protein is a MDR (multi-drug resistance) protein.

MDR (multi-drug resistance) is defined as a resistance of the cells to structurally unrelated antineoplastic substances. Tumor cells react by overexpression of a plasma membrane glycoprotein which can pump out ATP-dependent cytotoxic substances from the cells. By overexpression of these MDR proteins (135–180 KD), the cells survive even in relatively high concentrations of antiproliferative substances.

The function of MDR proteins as secretory pumps can be inhibited by calcium channel blockers, which leads to an accumulation of the substance in the cell. Calcium channel blockers known from the literature and also MDR-associated substances were therefore added to both cell lines in order to check whether the resistant line overexpressed MDR proteins. The calcium channel blocker used was verapamil, the MDR substrates used were daunorubicin and doxorubicin. The results are shown below in tabular form as % inhibitlion of proliferation and were determined with the aid of Test 2.

| Verapamil(nM) | A.20.2J* | A20R* | A20.2.J** | A20R** |
|---|---|---|---|---|
| 0 | 10.7% | 6.8% | 2.7% | 9.1% |
| 100 | 33.4% | 20.7% | 19.9% | 24.9% |
| 200 | 49.6% | 31.7% | 30.4% | 48.7% |
| 400 | 54.0% | 42.4% | 40.4% | 47.3% |

*Addition of 300 nM daunorubicin
**Addition of 300 nM doxorubicin

Both cell lines are inhibited by the two substances to the same extent. Thus, the resistant A20R cells do not show a higher acceptance due to increased MDR expression. Thus, the higher tolerance of the A20R cels is not due to an induction of MDR proteins, but is due to some other factor. The same test mixture was chosen in order to check whether A77 1726 is an MDR-transported molecule. Numbers are % inhibition of proliferation.

| Verapamil (nM) | A20.2J + 1.6 μM A77 1726 | A20R + 62.5 μM A77 1726 |
|---|---|---|
| 0 | 16.4% | 10.3% |
| 100 | 14.3% | 6.4% |
| 200 | 12.5% | 9.9% |
| 400 | 7.9% | 13.9% |

In the case of these cell lines, it was determined that A77 1726 is not transported by MDR proteins. Thus, the leflunomide resistance of the A20.R cells is not caused by the action of MDR proteins, transporting the leflunomide out of the cells.

EXAMPLE 4

Micropreparative Purification of a 135 kD Protein a.) Sample preparation for protein determination a.1) Protein concentration was determination using the methods described by Popov, et al., Acta Biol. Med. Germ. 34, pp.1441–1461.

The principle of the method is that dilute protein solutions are precipitated as colored pellet using Napthol Blue/Black/methanol/acetic acid, washed, taken up in 0.1 M NaOH and the extinction is measured at 620 nm.

The protein content is calculated by means of a calibration curve using BSA solutions (BSA=bovine serum albumin).

This method for protein determination is not affected by detergents (SDS, Nonidet, etc.) and the presence of β-mercaptoethanol does not interfere with the method either. Original Eppendorf vessels should be used, as the adhesion of the pellets to the plastic surface is strong and protein losses due to dissolution of the pellets on pouring off the wash solutions are avoided.

The following solutions are needed:

"Popov 1 solution":

stir 0.65 g of Naphthol Blue/Black
+ 50 ml of Popov 2 for at least 1 h, can only be kept for one week.

"Popov 2 solution":

50 ml of glacial acetic acid
+ 450 ml of methanol

"Popov 3 solution":

4 ml of Popov 1
+ 36 ml of Popov 2, then filter

Plotting the calibration curve:

Preparation of the BSA solution: bovine albumin, from Sigma, 98 to 99% purity is prepared in a concentration of 1 mg/ml in 5% strength SDS solution. A relatively large amount of solution is prepared, which is stored in 1 ml portions at −25° C. A 1 ml portion is thawed and then vigorously shaken for 10 minutes at 95° C. in a thermomixer (Eppendorf thermomixer 5436).

| After cooling, the following dilutions are performed: | | |
|---|---|---|
| 10 μl of BSA solution | +990 μl of 5% strength SDS solution | 0.010 mg of BSA/ml |
| 25 μl of BSA solution | +975 μl of 5% strength SDS solution | 0.025 mg of BSA/ml |
| 50 μl of BSA solution | +950 μl of 5% strength SDS solution | 0.050 mg of BSA/ml |
| 75 μl of BSA solution | +925 μl of 5% strength SDS solution | 0.075 mg of BSA/ml |
| 100 μl of BSA solution | +900 μl of 5% strength SDS solution | 0.100 mg of BSA/ml |
| 150 μl of BSA solution | +850 μl of 5% strength SDS solution | 0.150 mg of BSA/ml |
| 200 μl of BSA solution | +800 μl of 5% strength SDS solution | 0.200 mg of BSA/ml |
| without μl of BSA solution | +1000 μl of 5% strength SDS solution | blank value |

200 μl of all 8 solutions are in each case taken twice (duplicate determination), mixed with 600 μl of "Popov 3", then mixed briefly vigorously (vortex).

Centrifuge for 5 minutes at 14000 rpm in a bench-top centrifuge (Eppendorf), the supernatant is discarded. The pellet is then washed 3 times with 750 μl of "Popov 2" each time and centrifuged off. After the last washing operation, the pellet is taken up in 1 ml of 0.1 M NaOH and the extinction is measured in a plastic cuvette (d=1 cm) against the blank value at 620 nm (spectrophotometer from Kontron).

| Example of a series of measurements: Concentration BSA (mg/ml) Extinction at 620 nm | |
|---|---|
| 0 | 0 |
| 0.010 | 0.0459 |
| 0.025 | 0.1154 |
| 0.050 | 0.2442 |
| 0.075 | 0.4025 |
| 0.100 | 0.4964 |
| 0.150 | 0.6856 |
| 0.200 | 0.9534 |

The correlation coefficient in the evaluation: protein concentration/extinction is, according to experience, 0.995–0.999 (in this example 0.998)

a.2) Sample preparation/protein determination of the A 20 cells:

$10^7$ A20 cells (the term A20 cells means both A20.2J and A20R cells), present in 1 ml of PBS buffer, are centrifuged for 5 to 10 seconds at $10^4$ rpm in the bench-top centrifuge (Eppendorf model 5415 C). The supernatant is discarded, the pellet is mixed with 1 ml of 5% SDS solution, and the mixture is sucked up with a pipette several times and thus homogenized and vigorously shaken for 10 minutes at about 95° C. in the thermomixer and then cooled. Of this solution: 20 μl are mixed with 980 μl of 5% SDS solution (50-fold dilution) and 50 μl are mixed with 950 μl of 5% SDS solution (20-fold dilution) and the mixture is vigorously shaken for 10 minutes at 95° C. in the thermomixer and cooled. 200 μl of each solution are then taken twice for duplicate determinations, mixed with 600 μl of "Popov 3" and thus additionally treated as described above for BSA. Evaluation is carried out with the aid of the calibration curve already described.

Measurements obtained:

| Dilution | Extinction at 620 nm | →Protein conc. × dilution factor (mg/ml) |
|---|---|---|
| 50-fold | 0.0972 | 0.915 |
| 20-fold | 0.1800 | 0.720 |

Result: A20 cells contain about 800 μg of protein/$10^7$ cells.

b.) Sample preparation for SDS-PAGE $10^7$ A20 cells, present in 1 ml of PBS buffer, are centrifuged for 5 to 10 seconds at $10^4$ rpm in the bench-top centrifuge (Eppendorf model 5415 C).

b. 1) Direct lysis

The supernatant is discarded, the pellet is mixed with 400 μl of sample buffer and homogenized by sucking up several times with the pipette, and the mixture is vigorously shaken (vortex shaker) and agitated for 5 to 10 minutes at 95° C. in the abovementioned thermoshaker or water bath. The protein concentration of this highly viscous solution is about 2 mg/ml. For a Coomassie-stained gel, 40 to 50 μl/sample bag of this solution, corresponding to 80 to 100 μg of protein, are needed. For Ag-stained gels, the solution described is then additionally diluted 1:20, 40 to 50 μl thus correspond to a protein concentration of 4 to 5 μg/sample pocket.

Composition of the sample buffer:

| | |
|---|---|
| Millipore $H_2O$ | 2.7 ml |
| Glycerol, 98% strength | 10.0 ml |
| 0.25M Tris/1M glycine | 9.0 ml |
| 25% SDS soln. | 6.8 ml |
| 0.1% Bromophenol Blue soln. | 2.5 ml |
| 2-mercaptoethanol | 4.0 ml | b.2) Freezing of the cells and subsequent lysis

The cell pellet was immediately immersed in liquid nitrogen for about 1 minute in the closed Eppendorf vessel and stored at −80° C. On lyzing the sample buffer is added directly to the intensely cooled cell pellet.

c.) SDS-PAGE

Various polyacrylamide gels were used (10%, 12%, 4 to 22.5% PAA). Best results with respect to band sharpnesses were obtained using gradient gels whose PAA content was 4 to 10%. The techniques/solutions needed for this are described below:

Separating gel

Composition of the gel solutions for gradient gel 4 to 10% AA for a gel (about 24 ml):

| Component | 4% AA soln. | 10% AA soln. |
|---|---|---|
| $H_2O$ | 7 ml | — |
| Glycerol | — | 6.1 g |
| Stock soln. 1 | 1.6 ml | 4 ml |
| 3M Tris, pH 8.8 | 3 ml | 3 ml |
| 10% APS | 80 μl | 40 μl |
| 10% SDS | 120 μl | 120 μl |
| TEMED | 10 μl | 10 μl |

Stock solution 1: 30% acrylamide/0.5% N,N'-methylenebisacrylamide
crosslinking: 1.7%
APS: ammonium persulfate Collecting gel Composition of the gel solution with 3.8% AA for two gels (about 10.5 ml)

| Component | |
|---|---|
| $H_2O$ | 3.7 ml |
| Stock soln. 2 | 4.0 ml |
| 0.5M Tris, pH 6.8 | 2.5 ml |
| 10% APS | 200 μl |
| 10% SDS | 100 μl |
| TEMED | 12 μl |

The gel was poured according to known standard methods and, after adequate polymerization, fixed in a vertical electrophoresis chamber. For a Coomassie/silver-stained gel, 40 μl each of the A20 sample described under b)=80 μg/4 μg of protein per sample pocket were applied.

The molecular weight standard used was the "Combithek" marker from Boehringer Mannheim, whose molecular weight range in the reducing sample buffer extended from 170 to 14 kD.

Composition of the electrophoresis running buffer: ready-to-use dilution with Milli Q $H_2O$

| | |
|---|---|
| SDS | 0.1% |
| Tris | 50 mM |
| Glycine | 200 mM |

Flow conditions: about 5 hours at 35 mA/gel (voltage 400 V) when using a gel having the measurements 17×18×0.1 cm.

Stains:

| Sequence | Time | Composition of the solution |
|---|---|---|
| 1. Coomassie stain | | |
| Fixing/staining | 20–30 min | 0.2% Coomassie Brilliant Blue R 250 in 50% methanol/10% acetic acid/40% $H_2O$ |
| Destaining | as desired, repeatedly change soln. | 20% i-propanol, 7% acetic acid, 3% glycerol, 70% $H_2O$ |
| 2. Silver stain (modified Heukeskoven stain) | | |
| Fixing | 30 min | 40% ethanol, 10% acetic acid, 50% $H_2O$ 0.40 g of sodium thiosulfate · 5 $H_2O$ + 5.00 g of sodium acetate |
| Incubation | 2–24 h | +60 ml of ethanol shortly before use: + 1.0 ml of glutaraldehyde (25% strength) make up to 200 ml with $H_2O$ |
| Washing | 3 × 5–10 min | $H_2O$ 200 mg of silver nitrate |
| Staining | 45 min | shortly before use: + 40 μl of formaldehyde soln., 35% strength make up to 200 ml with $H_2O$ |
| Washing | 10 sec | $H_2O$ 5 g of sodium carbonate |
| Developing | 2–10 min | shortly before use: + 20 μl of formaldehyde, about 35% strength make up to 200 ml with $H_2O$ |
| Stopping | 10 min | 1.5% strength $Na_2$EDTA · $2H_2O$ |

All the abovementioned steps were carried out while gently agitating (shaking table) in 200 ml/gel in each case.

Before photographing/scanning/drying or heat-sealing into plastic bags, the gel was incubated for several hours to overnight in double-distilled $H_2O$.

Storage: the heat-sealed gels were stored at room temperature or stacked one on the other in a refrigerator (T:>0° C.), if possible protected from light.

Evaluation/assessment of the gels

In the high-molecular weight range (between marker bands 170 and 116 kD), a protein band was detected which is expressed much more strongly in resistant A20 cells than in A20J.2 cells. This was observed both on Coomassie and on silver staining (see FIG. 1).

Molecular weight

Of the eight calibration standards, the running distance of the individual proteins in the 4 to 10% gel was plotted in relation to the logarithm of the molecular weight. It was thus possible to calculate the molecular weight of the abovementioned protein bands having a known running distance. The total running distance was 11.2 cm.

| Protein name of the Combithek marker | $M_r$ (D)/log $M_r$ | Running distance (cm) | $R_f$ |
|---|---|---|---|
| $\alpha_2$-macroglobulin (equine plasma) | 170000/5.230 | 4.37 | 0.39 |
| β-galactosidase (*E. coli*) | 116353/5.066 | 5.78 | 0.516 |
| Fructose-6-phosphate kinase (rabbit muscle) | 85204/4.930 | 7.20 | 0.643 |
| Glutamate dehydrogenase (bovine liver) | 55562/4.745 | 8.35 | 0.746 |
| Aldolase (rabbit muscle) | 39212/4.593 | 9.17 | 0.819 |
| Triose phosphate isomerase (rabbit muscle) | 26626/4.425 | 10.00 | 0.893 |
| Trypsin inhibitor (soybeans) | 20100/4.303 | 10.33 | 0.922 |
| Lysozyme (egg white) | 14307/4.156 | 10.63 | 0.949 |
| Unknown protein, 5 applications | ? | 5.58–5.65 (5.60) | 0.500 |

The mean value of the running distances of the 5 applications of the unknown protein is given in brackets. The correlation coefficient between the values was 0.977. The calculated molecular weight is $M_r$ 135 kDa.

Densitometric evaluation of the quantitative data

On a Bio Image(R) system (Millipore, Eschborn), a quantification of the bands of a Coomassie-stained PAA gel (4 to 10%) with resistant A20 cells (A20R) was performed in using the "whole band menu," as described in the manual for the Bio Image$^R$-System. Result in 5 evaluated tracks having different protein contents:

| Total amount of protein (μg) | IOD = integrated optical density, (%) of the 135 kD protein band |
|---|---|
| 80 | 1.07 |
| 80 | 1.03 |
| 60 | 1.05 |
| 60 | 1.04 |
| 40 | 1.32 |

Accordingly, the proportion of the 135 kD protein in resistant A20 cells is about 1% of total cell protein. In normal A20 cells (A20.2 J), it was not possible to quantitatively determine this band by applying 80 μg of protein, as it was expressed at nearly undetectable levels when compared to the resistant cells.

Other information was obtained using SDS-PAGE. In one sample work-up, the sample buffer described under a) was modified in that no mercaptoethanol was added. With this condition, the proteins which are formed by S—S bridges do not split up into subunits. Thus, there was no change in the molecular weight of the 135 kD protein and the protein does not likely contain S—S bonds.

d.) Micropreparative concentration of the 135 kDa protein

The amount of protein needed for sequencing is in general given as 100 pmol, which corresponds to about 14 μg of protein. On careful estimation (in comparison to the concentration of the marker), the concentration of the 135 kDa protein was estimated at 0.3 μg on an 80 μg total application. 16 gels were run (PAA 4 to 10%), which yielded 104 samples of the 135 kDa bands. These samples were forced through a 32μ sieve. The total amount of protein applied in a sequencing experiment was always 80 μg.

e.) Protein digestion in the polyacrylamide gel

After SDS-PAGE and Coomassie staining, the gel bands were excised and washed until neutral within one day by changing the $H_2O$ several times. The pieces of gel were then forced through a 32 μm sieve (in a syringe without a needle). The fine gel paste was then evaporated almost to dryness in a vacuum centrifuge.

The addition of enzyme/buffer was then carried out—endoproteinase LYS-C (Boehringer Mannheim) in a 10-fold excess was added. The mixture was incubated for 6 to 7 hours at 37° C., then eluted at 37° C. for several hours using 1 ml of 60% acetonitrile/0.1% TFA. The supernatant was pipetted off and the elution was repeated overnight at room temperature. The supernatant was then pipetted off, combined with the first supernatant, again filtered through a 0.02 μm filter (Anatop$^R$ from Merck) and evaporated in a vacuum centrifuge.

Before injection into the HPLC, the residue is diluted with 10–20% formic acid.

f.) Peptlide separation the HPLC

| Measuring conditions: | |
|---|---|
| Column: | Superspher ® 60 RP Select B |
| Eluent A: | 0.1% TFA (trifluoroacetic acid) in $H_2O$: |
| Eluent B: | 0.1% TFA in acetonitrile |
| Gradient: | t [min]    % B |
| | 0    0 |
| | 60    60 |
| | 65    70 |
| Flow rate: | 0.3 ml/min |
| Measurement wavelength: | 206 nm |

Figure 2:
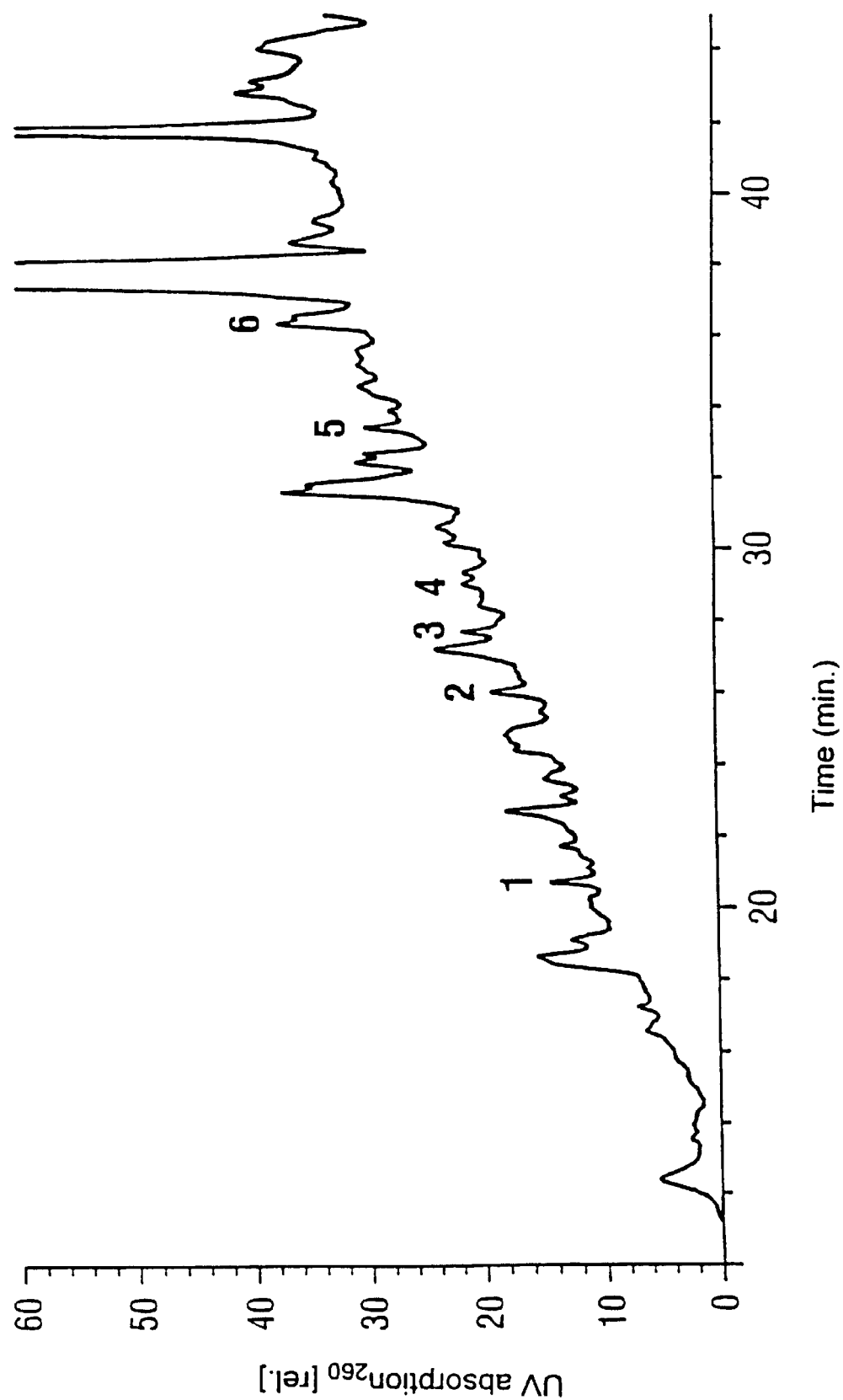
FIG. 2: Peptide separation by HPLC. The HPLC was carried out according to the conditions indicated under Example 1f. In the elution profile are the 6 peaks which correspond to the peptides 1–6 of Example 1 g, numbered continuously. Relative absorption units at a wavelength of 206 nm are indicated on the Y axis, the time in minutes is indicated on the X axis.

The result is shown in FIG. 2.

g.) Automatic N-terminal protein sequence analysis according to Edmann (Beckmann analyzer; Beckman, Dreieich/Buchschlag, Germany)

| Peptide 1 | KLG DI MGVK KE (SEQ ID NO: 1) |
| Peptide 2 | KLG DI MGVK KETEPDK (SEQ ID NO: 2) |
| Peptide 3 | KLIVTSATMDA E K (SEQ ID NO: 3) |
| Peptide 4 | DATSDLAIIARK (SEQ ID NO: 4) |
| Peptide 5 | KIFQ K (SEQ ID NO: 5) |
| Peptide 6 | TP Q EDYV E AAV (SEQ ID NO: 6) |

The peaks coresponding to peptides 1 bis 6 are marked in FIG. 2.

h.) Databank comparison with known protein sequences

The peptide sequences obtained in some cases showed a high homology to a protein derived from the gene sequence of *Caenorhabtitis elegans*, whose function is unknown. The amino acids not corresponding to this *C. elegans* sequence are underlined (see section g.). The extremely strong homology of peptide 3 with the *C. elegans* sequence and the missing or poor correspondence with peptide 4 or peptide 2 are a clear confirmation of the fact that the protein according to the invention is a novel representative of the DEAD box protein class. It is known from the literature that the SAT box (corresponding to peptide 3) is highly conserved in DEAD box proteins from bacteria to mammals.

The following examples describe molecular-biological experiments that were carried out. Fundamental molecular-biological standard methods, which are described, for example, in "Molecular Cloning—A Laboratory Manual", 2nd Edition by Sambrook et al., appearing in Cold Spring Harbor Laboratory Press, are well known to the skilled artisan. Such techniques include, for example, preparation of plasmid DNA, plasmid minipreparation, plasmid maxipreparation, elution of DNA fragments from agarose gels, elution by filtration, elution by adsorption, enzymatic modification of DNA, digestion of the DNA by restriction endonucleases, transformation of E. coli, preparation of RNA, RNA preparation using the single-step method (according to Chomzynski), mRNA preparation using Dynabeads$^R$, RNA gel electrophoresis, Northern blots, radiolabeling of DNA, "Random primed" DNA labeling using [α-$^{32}$P]dATP, sequencing of DNA by the dideoxymethod, cDNA preparation from total RNA, nonradioactive labeling of nucleic acid, "Random primed" DNA labeling using digoxigenin (DIG), detection of the DIG-labeled nucleic acids.

EXAMPLE 5

PCR Amplification of a cDNA Fragment Corresponding the Amino Acid Sequences from the Murine 135 kD Protein.

The reactions were carried out in a Perkin Elmer cycler. For a 50 µl PCR standard batch, the following components were pipetted together onto ice and coated with 50 µl of mineral oil:
1 µl of template DNA (0.5–2.5 ng) from A20R cells
1 µl of forward primer (30 pmol/µl)
1 µl of reverse primer (30 pmol/µl)
5 µl of dNTP mixture (2 mM per nucleotide)
5 µl of 10×PCR buffer
36.5 µl of H$_2$O
0.5 µl of Taq polymerase (2.5 units)
Amplification was carried out in 40 cycles under the following conditions:
  1st step: Denaturation of the DNA double strand at 94° C., 30 s.
  2nd step: Addition of the primer to the DNA single strand at 50° C., 2 min.
  3rd step: DNA synthesis at 72° C., 3 min.
In the last cycle, the DNA synthesis was carried out for 5 min and the batch was then cooled down to 4° C. For analysis, 10 µl of the batch were analyzed on a 1 to 2% strength agarose gel. the following primers were used:
  Forward primer: A20-2, A20-3, A20-4, A20-5 (see FIG. 7)
  Reserve primer: A20-6a, A20-6b (see FIG. 7)
  Matrices: A20R-total RNA
Forward and reverse primers were in each case combined in pairs in PCR reactions. The batch A20-3/A20-6b led to the amplification of a cDNA about 630 bp in size, which was reamplified with the primer A20-6b to check its specificity with combinations of the primers A20-3, A20-4 and A20-5. To increase the stringency, a temperature of 55° C. was selected for the reamplification and only 35 PCR cycles were carried out. After cloning and sequencing the fragment obtained (name: A20-5/-6b) using standard methods, the sequence data shown in FIG. 8 were obtained. The A20-5/-6b sequence was obtained by using the primers A20-5 and A20-6b, using A20R DNA as a template. This protein is classified as a DEAH-box protein based on the DEAH motif found at amino acids 170-173 of the sequence in FIG. 8 (residue 170–173 of SEQ ID NO:16) and based on the presence of the amino acid sequences GETGSGKT (residue 73–80 of SEQ ID NO:16) and PRRVAA (residue 103–108 of SEQ ID NO:16), which are also characteristic of DEAH-box proteins.

EXAMPLE 6A

Isolation and Sequencing of Full-length Sequence for Murine 135 kD DEAH-box Protein Using techniques that are well known to the skilled artisan, a probe is prepared from the nucleotide sequence in FIG. 8 (SEQ ID NO:15). For example, the entire sequence shown in FIG. 8 can be used as a probe. This probe is used to screen a genomic, of cDNA library prepared from murine A20.2J cells. The full-length clone is isolated a sequenced using techniques that are well known to the skilled artisan.

EXAMPLE 7

Northern Hybridization

Figure 3A:
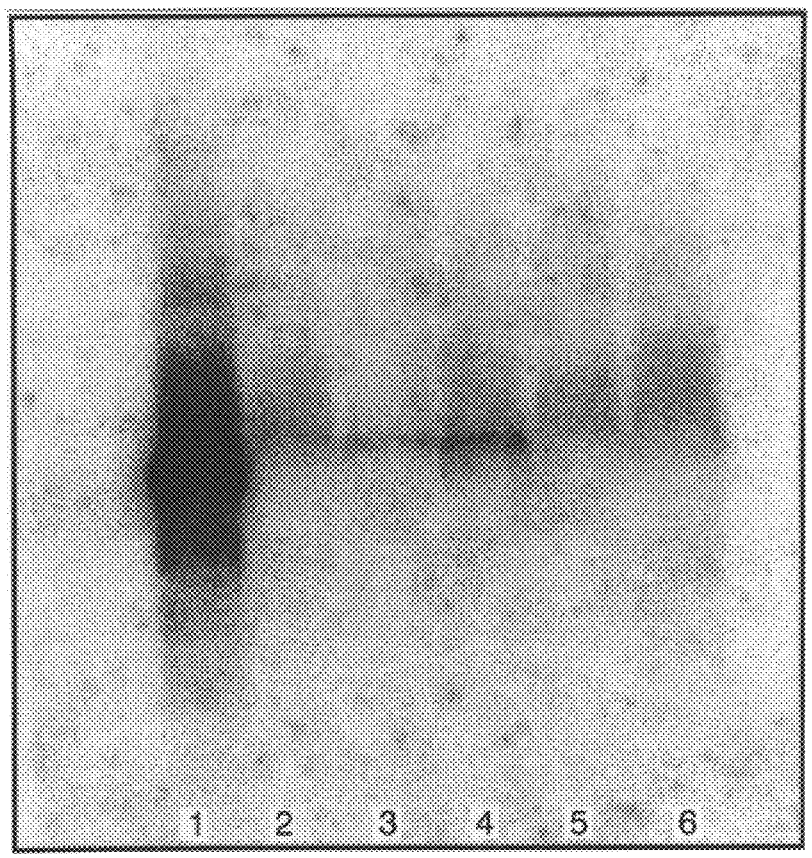
FIG. 3 (A): Time course of level of mRNA for 135 kD DEAH-box protein in normal A20.2J cells and leflunomide-resistant A20R cells treated with A77 1726. The hybridization was carried out using the radiolabeled DNA probe A20-5/6b, whose sequence contains the preserved regions of the DEAD box protein DEAH subfamily. Probe A20-5/6b was made by using the primers A20-5 and A20-6b and A20R DNA as template DNA. The molecular weight marker used was the RNA length standard I from Boehringer Mannheim. In the 1st track the A20R entire RNA is applied, in the 2nd track A20.2J entire RNA without treatment of the corresponding cells with A77 1726, in the 3rd–6th track A20.2J entire RNA in each case with incubation of varying length of the corresponding cells with 5 μM A77 1726 (1 hour, 8 hours, 16 hours, 24 hours). 20 μg of entire RNA of each batch were applied.
FIG. 3(B): the same blot as under (A) has been hybridized with a β-actin sample as control.
Figure 3B:
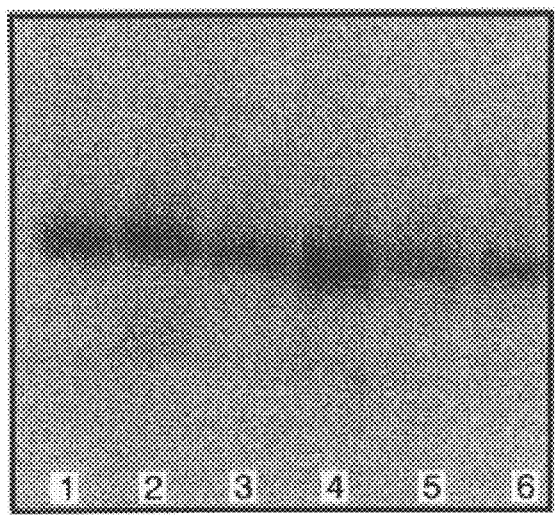

The hybridization solution used was a ready-to-use ExpressHyb$^R$ solution from Clontech, which binds the previously labeled gene probe (radioactive or nonradioactive) to the possibly present complementary DNA sequence on the carrier filter in a hybridization time of one hour. Reagents additionally needed:
  20×SSC: 3 M NaCl; 0.3 M sodium citrate (pH 7.0)
  Wash solution 1: 2×SSC; 0.05% SDS
  Wash solution 2: 0.1×SSC; 0.1% SDS
  Wash solution 3: 2×SSC; 0.1% SDS
1. Hybridization with nonradiolabeled gene probes using the ExpressHyb solution (Clontech)
  The ExpressHyb solution was heated to 68° C. and stirred at the same time, so that no precipitates remained. The membrane (10×10 cm) was then prehybridized in at least 5 ml of ExpressHyb solution by mixing continuously in a hybridization oven at 68° C. for half an hour. The non-radiolabeled DNA probe was mixed with 5 ml of fresh ExpressHyb solution. The prehybridization solution was then replaced by this ExpressHyb® solution and the blot was incubated at 68° C. in the hybridization oven for one hour. After incubation, washing at room temperature was carried out for 30 min using 20 ml of the wash solution 3 (per 100 cm$^2$ of membrane), the solution being replaced once. The second washing step was carried out at 50° C. for 30 min using wash solution 2. Here too, the solution was replaced once. The excess wash solution was then allowed to drip off the membrane and it was then possible to use the membrane directly for chemiluminescence detection.
2. Hybridization with radiolabeled gene probes using the ExpressHyb® solution (Clontech)
  Hybridization was carried out as in the case of the nonradiolabeled DNA probe. After incubation, however, washing was carried out with wash solution 1 for 30–40 min at room temperature with replacement of the solution several times. The second washing step was carried out with wash solution 2 for 40 min at 50° C. In this case, the solution was replaced once. After this, the excess wash solution was also allowed to drip off here and the blot was heat-sealed in a plastic film. The blot was exposed at −70° C. in an exposure cassette or analyzed in a phosphoimager (BIORAD).
  The RNA and hybridization probe used are each given in the legends to the figures.
3. Time course of the mRNA level of the 135 kD protein under the influence of leflunomide in A20. J and A20R cells
  The experiment is shown in FIGS. 3A and 3B and the associated legend to the figures. In all cells investigated (A20.2J and A20R) is seen a band of size 4.4 kilobases. The radiolabeled probe A20-5-6b was used. The A20R cells give a very strong signal, A20.2J cells only a very weak signal. However, after treatment of A20.2J cells for one or 8 hours with A77 1226 the band becomes somewhat stronger. A77 1226 does not significantly induce the formation of the mRNA investigated here over the 8 hour time period tested.

4. Time course of the mRNA level of the 135 kD protein with varying concentrations of A77 1226.

Figure 4A:
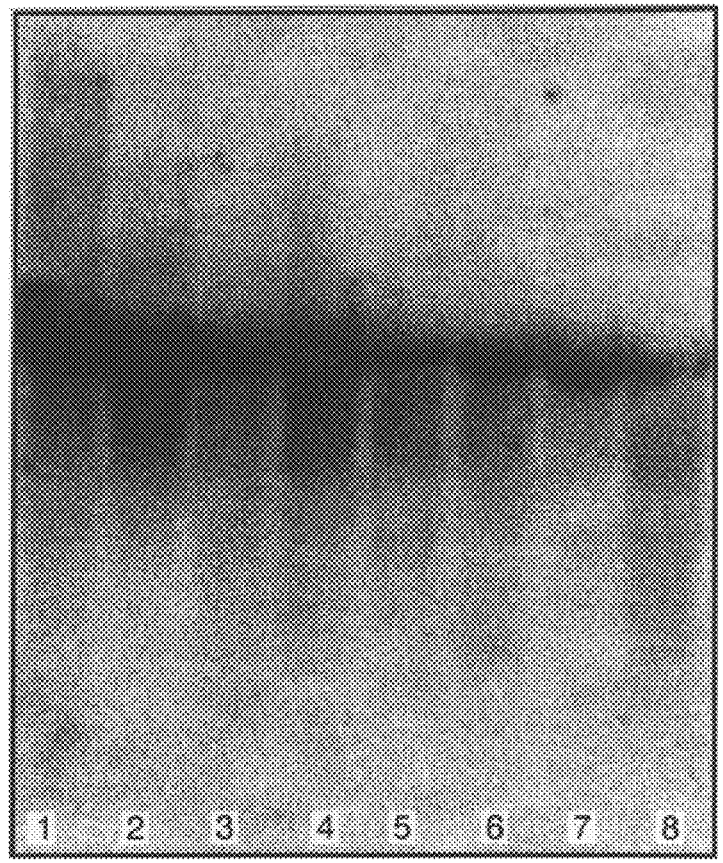
FIG. 4 (A) Northern experiment for the expression of the 135 kD DEAH-box protein after removal of leflunomide in leflunomide-resistant A20R cells. The control was the RNA of A20R cells which had been incubated with 100 μM leflunomide (track 1). Hybridization was carried out with the DNA probe A20-5/6b. The tracks 2, 3, 4, 5, 6, 7 and 8 each contained 15 μg of entire RNA from A20R cells which had been incubated without leflunomide over the periods 1, 2, 3, 4, 5, 14 days and 5 months.
FIG. 4(B): Control hybridization of the same blot with a β-actin sample. The blots are always shown with the appropriate quantitative assessment.
Figure 4B:
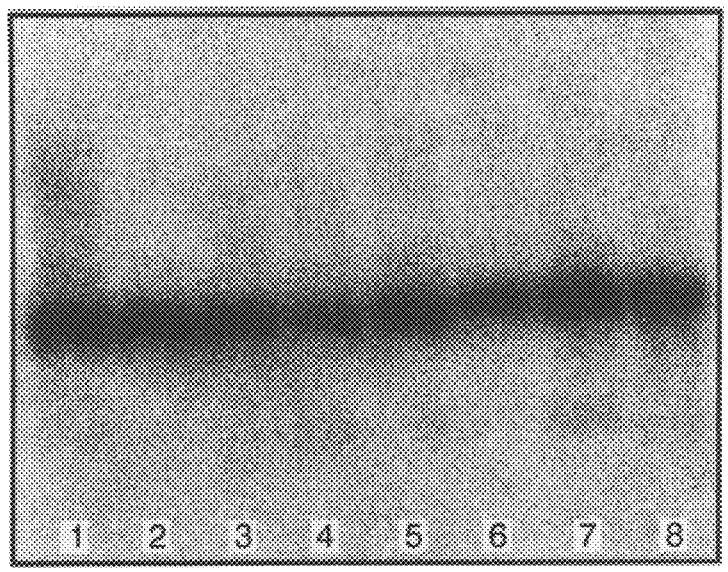

The experiment is shown in FIGS. 4A and 4B and the associated legend. A20R cells were cultured without A77 1226 in the medium for varying periods of time, up to five months. With depletion of A77 1226 over time, the level of the 4.4 kB mRNA gradually fell. The radiolabeled probe A20-5/-6b was used.

5. mRNA level of the 135 kD protein in eight different human tissues.

Figure 5:
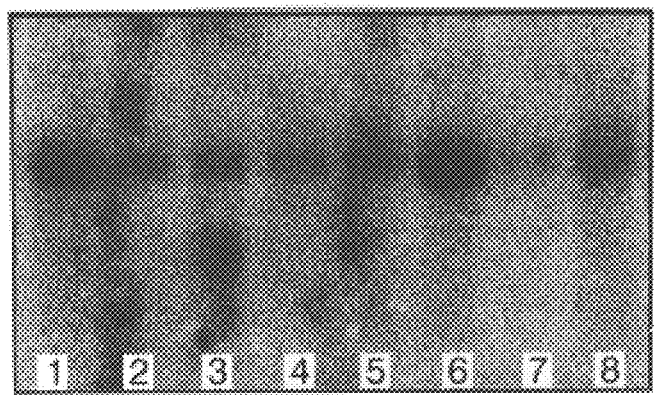
FIG. 5: Northern blot with about 2 μg of poly (A) RNA per track of eight different human tissues. The tracks 1-8 contain, from left to right, tissue from the heart, brain, placenta, lungs, liver, skeletal muscle, kidney and pancreas. The RNA was separated electrophoretically on a denaturing 1.2% strength agarose gel, and then blotted on a positively charged nylon membrane, then fixed by UV crosslinking. Hybridization was carried out with the A20-5/6b DNA probe. The appropriate quantitative assessment is shown under the blot.

This experiment is described in FIG. 5 and the corresponding legend. It is seen that the mRNA levels in the tissues investigated are different. The levels of mRNA for the 135 kD protein in heart and skeletal muscle were the highest among the tissues tested. As the mRNA expression correlates with the leflunomide resistance (see Example 3), muscular organs such as heart and skeletal muscle are possibly less sensitive to leflunomide.

EXAMPLE 8

Homologies of the Murine 135 kD DEAH-box Gene to a Human cDNA Clone

The amino acid sequence KLGDIMGVKK (SEQ ID NO:34) from a subregion of the differentially expressed 135 Kd DEAH-box protein from leflunomide-resistant A20R cells was found in an entry of the cDNA clone B 1 85 (Homo sapiens) in the EM NEW (EMBL-new entries) databank. See Liew, et al. *Proc. Natl. Acad. Sci. USA* 91:10645 (1994). By means of this, it was possible to prepare suitable primers for the PCR which were used in a PCR using a human cDNA bank as a matrix to amplify a cDNA corresponding to the murine 135 kD protein The novel upstream and downstream primers are presented in FIG. 7 as primer Nos. 7 and 8 (7=hs1, 8=hs2).

The conditions of the PCR were kept stringent, as the primers were complementary to the target sequence. The hybridization was carried out for 45 s at 55° C., the denaturation for 30 s at 94° C. and the synthesis for only 45 s at 72° C. The reason for the short denaturation and synthesis phase was the known length of the insert to be expected (246 bp). The concentration ratios of the PCR were selected according to standard as in Example 5. The matrices used were three different human cDNA banks (prepared from (1) peripheral T cells, (2) PMA-stimulated HI-60 myeloid precursor cells and (3) placenta). In each case a 246 bp-long PCR fragment was obtained whose sequence corresponds to the nucleotide 1431 to 1672 of FIG. 9 (bases 1451–1672 of SEQ ID NO:17).

EXAMPLE 9

Obtaining the Complete Human cDNA Clone by Colony Hybridization

On the basis of the results of the Northern blot experiments (Example 6), a cDNA bank prepared from human skeletal muscle was used for screening. The probe employed was the sequence hs1/hs2. This sequence was prepared using the hs1 and hs2 primers and the Liew, et al. sequence above as a template. For the synthesis of labeled probe DNA, hs1/hs2 DNA was amplified by means of PCR using the primers hs1 and hs2 and the hs1/hs2 clone (vector: pCR™II, Invitrogen, San Diego, USA) as a template and then purified by means of agarose gel electrophoresis and phenolic elution. For DIG labeling with the aid of random primers ("random primed labeling"), 1 ug of hs1/hs2 DNA was employed as a template and, after a reaction time of 20 h, about 2 μg of labeled probe DNA were obtained per 1 μg of template. In order to check the probe specificity, a dilution series of hs1/hs2 DNA from 0.1 pg to 10 ng was immobilized on nylon membrane and hybridized with the DIG-labeled hs1/hs2 probe. It was seen that 5–25 ng of probe per ml of hybridization solution were sufficient in order to detect 10 pg of hs1/hs2 DNA poorly and from 100 pg of hs1/hs2 DNA (Hybond N+) clearly.

For the first screening of the gene bank, about 40,000 colonies were plated out per 150 mm agar plate. Altogether, 20 master plates were prepared, so that about 800,000 individual colonies had been plated out. With this colony count, the probability appeared to be adequate that in a number of $1.1 \times 10^6$ independent clones given by the manufacturer the clone sort was among those plated out. 2 each, i.e. a total of 40 replica filters were prepared which were subjected to hybridization with DIG probe. For this hybridization, a probe concentration of 25 ng/ml was employed. For detection, the membranes were exposed to X-ray films for 2 hours. On 5 different plates a total of 19 positive clones were detected. Of the 19 positive clones from the primary screening, 5 clones were confirmed in the secondary screening. These clones were isolated and characterized. The following estimated insert sizes resulted for the clones:

| Clone 1 | 1.6 kb |
| Clone 2 | 3.5 kb |
| Clone 3 | 1.6 kb |
| Clone 4 | 0.9 kb |
| Clone 5 | 6.5 kb |

For the purpose of further characterization, the clones were initially sequenced and the subsequences and restriction maps obtained were compared with one another. The comparison of the sequences with one another confirmed that clone 1 and clone 3 were almost identical. It turned out that the clones 1, 2, 3 and 4 corresponded to a gene sequence which comprised the hs1/hs2 cDNA sequence and corresponded to an estimated length of 4.5 kb. The complete 5'-end and the poly-A tail of the mRNA additionally appeared to be contained in this sequence. From the total length, it was expected that this was the complete sequence which would be necessary for the expression of a 135 kD protein. A schematic representation shows the orientation of the human cDNAs to one another and the position of the sequence hs1/hs2 used for screening (FIG. 6A).

In comparison to the other clones, clone 5 appeared different. The initial sequencing of this clone yielded no overlaps at all with the other sequences and also no indication of the position of the hs1/hs2 sequence in the clone. Even in the course of restriction analysis, plasmid 5 showed peculiar features which gave rise to the suspicion that it did not originate from the same gene as the other clones. Also the unusual length of the inserts, estimated at 6.5 kb, suggested that this is an isolated cDNA. In other words, this sequence has no overlaps with the other four clones and is therefore unrelated to those clones. Using procedures well known to the skilled artisan, a full length clone is isolated using Clone 5 as a probe. This full-length clone is sequenced.

Clone 1 and clone 2 were completely sequenced. The sequencing data are shown in FIG. 9. The two sequences overlapped by 530 base pairs and when the two sequences were superimposed, there was on open reading frame of 4.3 kB in length. Clone 1 was exactly 1590 base pairs in length and clone 2 was 3210 base pairs in length. The previously known sequence hs1/hs2 was between positions 1430 and 1672.

The position of this sequence was an indication of the fact that the first (beginning with the first base) of the six possible reading frames was the correct one. In this reading frame were two stop codons: one in base position 58 (TGA) and one in position 3729 (TGA), after which a poly-A tail followed about 300 base pairs downstream. After the first stop, in position 148 followed a methionine codon which appeared to be a possible start codon for the translation, as it was not only the first ATG codon in the sequence, but also had characteristics of a Kozak start sequence, namely a purine residue (G) in position −3 and a G in position +4. Just under 1000 base pairs further appeared the next ATG codon, more accurately two methionine codons in sequence. On account of the environment—an A on −3 and a G on +4—the second codon could likewise be a start codon. As in 90–95% of the cases of known mammalian mRNA translation initiation the methionine codon appearing first in the reading frame is simultaneously the start codon, this was also assumed for the present case. Starting from this assumption, the sequence would code for a 1227 amino acid protein. With an average weight of 110 daltons per amino acid, such a protein would correspond to just under 135 kD. On account of the size of the protein, the uninterrupted reading frame, and the relatively distinct start codon, the sequence was judged to be the complete cDNA for the human 135 kD protein.

The similarity of the human sequence with the murine sequence A20-5/6b was also determined. The comparison of the sequence 05/6b from the murine cell line A20R with the human sequence found yielded a difference of 15 amino acids out of 245, which corresponded to a percentage difference of about 6%.

EXAMPLE 10

Homology Domains in the Human Sequence Found and Similarities to Other Proteins

Sequence comparison with the homology domains of the superfamily II of putative helicases showed that all conserved domains of the DEAH protein family were present in the human sequence (FIG. 6b). The following features distinguish the sequence 135 kD human DEAH-box from other DEAH-box proteins. First, the first homology domain (ATPase A, Domain I) is located more than 650 amino acids from the N-terminus. Second, there are Serine/Arginine (SR) domains in the N-terminus. Third, domain IV has the sequence FMP instead of FXT. Fourth, the distance between domains IV and V is only 74 amino acids, instead of the 75 to 84 amino acids which are typical of other DEAH-box proteins. Finally, domain VI has the sequence QRSGRXGR (SEQ ID NO:25) instead of the sequence QRIGRXGR(SEQ ID NO:26).

The first domain—the ATPase A motif, begins with the 655th amino acid. Among domains I through VI, only a two amino acids differ from the homology sequence for other members of the DEAH-box protein family: a proline instead of a threonine in domain IV and a serine instead of an isoleucine in domain VI. Furthermore, the 654 amino acid distance of the first homology domain (Domain I) from the N-terminus is 150 residues larger than in previously known DEAH box proteins. A further difference is the distance between domains IV and V: instead of 75 to 80 amino acids, here there were only 74 amino acid in between these domains in the gene encoding the human 135 kD DEAH-box protein gene of the invention.

Otherwise, the protein derived from the human cDNA could be clearly classified in the DEAH box proteins family on account of the homologies shown. In addition, at the N-terminus of the sequence was identified an amino acid sequence which has strong homologies with the "nuclear localization site" (NLS) of the SV 40 T antigen. This NLS homology begins with the 69th amino acid of the human 135 kD protein gene and is 10 residues long.

For further characterization of the human 135 kD protein sequence, a sequence comparison was carried out in the GCG program with "genembl", "swissprot" and "pir" on the DNA and on the protein level.

The gene bank analysis yielded homologies to some already-known proteins of the DEAH protein family (FIG. 10). The protein with the strongest homologies was identified as K03H1.2 from *C. elegans*. This protein was classified as a possible DEAH box protein on the basis of homology domains present (Wilson et al., 1994, Nature 368: 32-38). As indicated in Example 4(g), originally sequenced peptide fragments of the 135 kD protein from A20R cells likewise had similarities to the sequence from *C. elegans*. This data suggests that the overexpressed protein in A20R is a helicase.

In addition, a protein which was homologous at the DNA level to 60% was identified, which was cloned in 1994 from HeLa cells and designated as HRH1 (Ono et al., 1994, Molecular and Cellular Biology. 14: 7611–7620) - likewise a possible human RNA helicase. Further homologies of about 50% at the protein level were found to be the splice factors PRP 2, 16 and 22 from *S. cerevisiae*, likewise members of the DEAH family (Chen and Lin, Nucl. Acids Res. 18: 6447, 1990; Schwer und Guthrie, Nature 349: 494–499, 1991; Company et al., Nature 349: 487–493, 1991). Furthermore, significant homologies to the DEXH proteins MLE from *D. melanogaster* (Kuroda et al., 1991, Cell 66: 935-947) and the possible nuclear DNA helicase 11 - NDH II -from cattle (42 and 43% on the protein level) were found (Zhang et al., 1995, J. Biol. Chem. 270: 16422–16427).

EXAMPLE 11

In Vitro Expression of the Human 135 kD DEAH-box Protein

By means of rabbit reticulocyte lysate, an in vitro translation of the cDNA obtained was carried out. The full-length 135 kD DEAH-box protein human clone was used. To this end, various batches of linearized and circular DNA between 0.5 and 2.0 μg were employed. The positive control used was the luciferase DNA additionally supplied by Promega. The translation was carried out using T7 polymerase. The gene product was labeled by incorporation of $^{35}$S-methionine and could thus be rendered visible in an autoradiogram after separation on a denaturing SDS-PAA gel.

Independently of the amount of DNA employed, all batches afforded good results, the circular DNA being translated somewhat more efficiently than the linearized DNA. The positive control showed the expected luciferase band at 61 kD, the zero control without DNA as expected afforded no signal. In the gene products of the helicase cDNA, the most prominent band of synthesized protein with the greatest protein concentration was between the protein standards for 97.4 and 220 kD. There were also weaker bands of relatively small translation products which were probably formed by the premature termination of protein or mRNA synthesis.

A direct comparison between the native protein from A20R cells and the gene product of the in vivo translation was carried out. To this end, parallel cell lysates of A20.2J and A20R cells and also the in vivo translation product of the cloned cDNA sequence and the zero control were applied to an SDS-PAA gel. As in the 50 µl batch of the reticulocyte lysate, amounts of protein of between 150 and 500 ng are produced (data from Promega with respect to luciferase control) and 1/10th of the batch was applied to a gel pocket. Coomassie staining (bands can be stained from a protein content of 100 ng) was not sufficient to detect the gene product produced in a reticulocyte lysate system.

Therefore, in addition to Coomassie staining, an autoradiogram with an X-ray film was set up. It was then possible to apply the film to the dried gel, whereby a direct comparison of the protein bands was possible. 5 µl of reticulocyte lysate with and without the human 135 kD protein gene product, 20 µl of A20R lysate and 23 µl of A20.2J lysate were applied (volumes in each case made up to 30 µl with SDS sample buffer) to a 7.5% SDS gel (separating gel: 5%). The marker used was a "rainbow marker" and a Coomassie marker. It was seen that a band of approximately 135 kD in from the A20R cell lysates appeared in the Coomassie-stained gel. The same gel overlaid with the associated autoradiogram shows that the band of the full-length 135 kD human protein gene product (detected by autoradiography) is at the same height as the 135 kD protein in A20R.

EXAMPLE 12

Assay of Enzymatic Activity of Human 135 kD DEAH box Protein

The helicase activity of the human 135 kD DEAH box protein is assayed using a helicase assay technique that is well known in the art, as described in the "Detailed Description of the Invention."

The ATPase activity of the human 135 kD DEAH box protein is assayed using an ATPase assay technique that is well known in the art as described in the "Detailed Description of the Invention."

The RNA splicing activity of the human 135 kD DEAH box protein is assayed using an RNA splicing assay technique that is well known in the art as described in the "Detailed Description of the Invention."

Priority application 19545126.0, Federal Republic of Germany, filed Dec. 4, 1 995, including the specification, drawings, claims and abstract, is hereby incorporated by reference.

We claim:

1. An isolated DNA sequence encoding the amino acid sequence of SEQUENCE ID NO. 16.

2. An isolated DNA sequence encoding the amino acid sequence of SEQUENCE ID NO. 18.

3. An isolated DNA sequence as set forth in SEQUENCE ID NO. 15.

4. An isolated DNA sequence as set forth in SEQUENCE ID NO. 17.

5. A polynucleotide that encodes a DEAH-box leflunomide-resistant protein, and which hybridizes, under stringent conditions, to the polynucleotide of SEQ. ID NO15;
   wherein said stringent conditions are 60° C. in 0.1×SSC and 0.1% SDS.

6. A polynucleotide that encodes a DEAH-box leflunomide-resistant protein, and which hybridizes, under stringent conditions, to the polynucleotide of SEQ. ID NO:17;
   wherein said stringent conditions are 60° C. in 0.1×SSC and 0.1% SDS.

7. An expression vector comprising a DNA sequence as claimed in claim 5.

8. An expression vector comprising a DNA sequence as claimed in claim 6.

9. A process for the preparation of a DEAH-box leflunomide-resistant protein, wherein said process comprises:
   (a) culturing a host cell comprising an expression vector according to claim 7; and
   (b) isolating said protein from the cell of step (a).

10. A process for the preparation of a DEAH-box leflunomide-resistant protein, wherein said process comprises:
    (a) culturing a host cell comprising an expression vector according to claim 8; and
    (b) isolating said protein from the cell of step (a).

11. An antisense expression vector comprising a DNA polynucleotide as claimed in claim 5, wherein said polynucleotide is inserted in reverse orientation into said vector.

12. An antisense expression vector comprising a DNA polynucleotide as claimed in claim 6, wherein said polymucleotide is insercted in reverse orientation into said vector.

* * * * *